United States Patent [19]
Parker et al.

[11] Patent Number: 5,976,798
[45] Date of Patent: Nov. 2, 1999

[54] METHODS FOR DETECTING MITOCHONDRIAL MUTATIONS DIAGNOSTIC FOR ALZHEIMER'S DISEASE AND METHODS FOR DETERMINING HETEROPLASMY OF MITOCHONDRIAL NUCLEIC ACID

[75] Inventors: William Davis Parker, Charlottesville, Va.; Corinna Herrnstadt, San Diego, Calif.; Soumitra Ghosh, San Diego, Calif.; Eoin D. Fahy, San Diego, Calif.

[73] Assignee: Mitokor, San Diego, Calif.

[*] Notice: This patent is subject to a terminal disclaimer.

[21] Appl. No.: 08/810,599

[22] Filed: Feb. 28, 1997

Related U.S. Application Data

[63] Continuation-in-part of application No. 08/410,658, Mar. 24, 1995, abandoned, and a continuation-in-part of application No. 08/614,072, Mar. 12, 1996, abandoned, which is a continuation of application No. 08/219,842, Mar. 30, 1994, Pat. No. 5,565,323.

[51] Int. Cl.$^6$ .............................. C12Q 1/68; C12P 19/34; C07H 21/04
[52] U.S. Cl. .......................... 435/6; 435/91.2; 435/91.52; 536/23.5; 536/24.31; 536/24.33
[58] Field of Search .......................... 435/6, 91, 2, 173, 435/91.52; 536/23.5, 24.31, 26.6, 24.33; 935/77, 78, 8

[56] References Cited

U.S. PATENT DOCUMENTS

| | | | |
|---|---|---|---|
| 5,185,244 | 2/1993 | Wallace | 435/6 |
| 5,192,659 | 3/1993 | Simons | 435/6 |
| 5,494,794 | 2/1996 | Wallace | 435/6 |
| 5,506,101 | 4/1996 | Ghodsian et al. | 435/6 |
| 5,514,543 | 5/1996 | Grossman et al. | 435/6 |
| 5,565,323 | 10/1996 | Parker et al. | 435/6 |

FOREIGN PATENT DOCUMENTS

WO 90/09455  8/1990  WIPO.

OTHER PUBLICATIONS

Iqbal Prog. Clin Biol. Res. 317: 679–687, 1989.
Parker et al. Neurology 40: 1302–1303, 1990.
Cooper Lancet 3411: 969–970 cited in 08/614072, 1993.
Mazuki et al. (human Genetics 88: 139–145, 1991.
Hamblet FASEB 7: A1085 cited in 08/614,072, 1993.
Anderson et al. nature 290: 457–465, 1981.
Picketts et al. Human Genet 89: 155–157, 1992.
Livak et al. Human Mutation 3: 379–385, 1994.
Parker et al. Ann Neurol 26: 716–723, 1989.
Keller and Manak, In DNA Probes, Stockton Press, ch1 and 7, 1993.
Parker, et al. "Cytochrome Oxidase Deficiency in Alzheimer's Disease", *Neurology* 40:1302–1303 (1990).
Anderson, et al., "Sequence and Organization of the Human Mitochondrial Genome", *Nature* 290:457–465 (1981).
Bennett, et al., "Cytochrome Oxidase Inihibition A Novel Animal Model of Alzheimer's Disease", *J. of Geriatric Psychiatry and Neurology* 5:93–101 (1992).
Kish, et al., "Brain Cytochrome Oxidase in Alzheimer's Disease", *J. of Neurochemistry* 59(2):776–779 (1993).
Bowling, et al., "Age–Dependent Impairment of Mitochondrial Function in Primate Brain", *J. of Neurochemistry* 60(5):1964–1967 (1993).
Chandrasekaran, et al., "Localization of Cytochrome Oxidase (COX) Activity and COX mRNA in Perirhinal and Superior Temporal Sulci of The Monkey Brain", *Brain Research* 606:213–219 (1993).
Wallace, et al., "Mitochondrial DNA Mutations in Epilepsy and Neurological Disease", *Epilepsia* 35(1):S43–S50 (1994).
Shoffner, et al., "Mitochondrial DNA Variants Observed in Alzheimer Disease and Parkinson Disease Patients", *Genomics* 17:171–184 (1993).
Simonian, et al., "Functional Alterations in Alzheimer's Disease: Diminution of Cytochrome Oxidase in the Hippocampal Formation", *J. of Neuropathy and Experimental Neurology* 52(6):580–585 (1993).
Howell, et al., "Leber Hereditary Optic Neuropathy: Identification of The Same Mitochondrial ND1 Mutation in Six Pedigrees", *Am. J. Hum. Genet.* 49:939–950 (1991).

Chandrasekaran, et al., "Differential Expression of Cytochrome Oxidase (COX) Genes in Different Regions of Monkey Brain" *J. of Neuroscience Research* 32:415–423 (1992).

Suggs, et al., "Use of Synthetic Oligonucleotides as Hybridization Probes: Isolation of Cloned cDNA Sequences for Human $\beta_2$–microglobulin", *Proc. Natl. Acad. Sci. USA* 78(11):6613–6617 (1981).

Saiki, et al., "Genetic Analysis of Amplified DNA with Immobilized Sequence–Specific Oligonucleotide Probes", *Proc. Natl. Acad. USA* 86:6230–6234 (1989).

Kuppuswamy, et al., "Single Nucleotide Primer Extension to Detect Genetic Diseases: Experimental Application to Hemophilia B (Factor IX) and Cystic Fibrosis Genes", *Proc. Natl. Acad. Sci. USA* 88:1143–1147 (1991).

Syvanen, et al., "A Primer–guided Nucleotide Incorporation Assay in The Genotyping of Apolipoprotein E" *Genomics* 8:684–692 (1990).

Landegren, et al., "A Ligase–mediated Gene Detection Technique", *Science* 241:1077–1080 (1988).

Conner, et al., "Detection of Sickle Cell $\beta^s$–globin Allele by Hybridization with Synthetic Oligonucleotides", *Proc. Natl. Acad. Sci. USA* 80:278–282 (1983).

Nickerson, et al., "Automated DNA Diagnostics Using An ELISA–based Oligonucleotide Ligation Assay", *Proc. Natl. Acad. Sci. USA* 87:8923–8927 (1990).

Fodor, et al., "Multiplexed Biochemical Assays with Biological Chips", *Nature* 364:555–556.

Fodor, et al., "Light–directed, Spatially Addressable Parallel Chemical Synthesis" *Research Article* 767–773 (1991).

Matthews and Kricka, "Analytical Strategies for The Use of DNA Probes" *Analytical Biochemistry* 169:1–25 (1988).

Francis Barany, "Genetic Disease Detection and DNA Amplification Using Cloned Thermostable Ligase", *Proc. Natl. Acad. Sci. USA* 88:189–193 (1991).

Gibbs, et al., "Detection of Single DNA Base Differences by Competitive Oligonucleotide Priming", *Nucleic Acids Research* 17(7):2437–2448 (1989).

Ghosh, et al., "Use of Maleimide–thiol Coupling Chemistry for Efficient Syntheses of Oligonucleotide–enzyme Conjugate Hybridization Probes", *Bioconjugate Chem.* 1(1)71–76 (1990).

Ishii and Ghosh, "Bead–based Sandwich Hybridization Characteristics of Oligonucleotide–Alkaline Phosphatase Conjugates and Their Potential for Quantitating Target RNA Sequences", *Bioconjugate Chem.* 4(1):34–41 (1993).

Jablonski, et al., "Preparation of Oligodeoxynucleotide–alkaline Phosphatase Conjugates and Their Use as Hybridization Probes", *Nucleic Acids Research* 14(15):6115–6129 (1986).

Li, et al., "Enzyme–linked Synthetic Oligonucleotide Probes: Non–Radioactive Detection of Enterotoxigenic *Escherichia Coli* in Faecal Specimens", *Nucleic Acids Research* 15(13):5275–5287 (1987).

Newton, et al., "Analysis of Any Point Mutation in DNA. The Amplification Refractory Mutation System (ARMS)", *Nucleic Acids Research* 17(7):2503–2517 (1989).

Gingeras, et al., "Use of Self–sustained Sequence Replication Amplification Reaction to Analyze and Detect Mutations in Zidovudine–resistant Human Immunodeficiency Virus", *J. of Infectious Diseases* 164:1066–1074 (1991).

Erlich, et al., "Specific DNA Amplification", *Nature* 331:461–462 (1988).

Richman, et al., "Human Immunodeficiency Virus Type 1 Mutants Resistant to Nonnucleotide Inhibitors of Reverse Transcriptase Arise in Tissue Culture", *Proc. Natl. Acad. Sci. USA* 88:11241–11245 (1991).

Wu and Wallace, "The Ligation Amplification Reaction (LAR)–amplification of Specific DNA Sequences Using Sequential Rounds of Template–dependent Ligation", *Genomics* 4:560–569 (1989).

Barany, et al., *PCR Methods and App.* 1:5–16 (1991).

Marzuki, et al., *Hum. Genet.* 88:139–145 (1991).

Wallace, D.C., *Science* 256:628–632 (1992).

Partridge, et al., *Arch. Biochem. Biophys.* 310:210–217 (1994).

Parker, Davis *Ann. Neurol.* 26:719–723 (1989).

Jenner, P. *Acta Neurol. Scand.* 84:6–15 (1991).

Hutchin, et al., *Proc. Natl. Acad. Sci.* 92:6892–6895 (1995).

Picketts, D.J., et al., *Hum. Genet.* 89:155–157 (1992).

Livak, K.J., et al. *Hum. Mutation* 3:379–385 (1994).

*Primary Examiner*—Carla J. Myers
*Attorney, Agent, or Firm*—Seed & Berry LLP

[57] ABSTRACT

The present invention relates to methods of detecting genetic mutations in mitochondrial cytochrome oxidase c genes that segregate with Alzheimer's Disease and methods for determining the amount of heteroplasmy of mitochondrial nucleic acid. The invention provides methods for detecting such mutations, as a diagnostic for Alzheimer's Disease, either before or after the onset of clinical symptoms.

34 Claims, 16 Drawing Sheets

COX 1  5'-END NON-CODING REGION,
       CODING REGION 5904-7445,
       AND 3'-END NON-CODING REGION

AGAGGCCTAA CCCCTGTCTT TAGATTTTAC AGTCCAATGC TTCACTCAGC
CATTTTACCT CACCCCCACT G

ATG TTC GCC GAC CGT TGA CTA TTC TCT ACA AAC CAC AAA GAC ATT GGA ACA
CTA TAC CTA TTA TTC GGC GCA TGA GCT GGA GTC CTA GGC ACA GCT CTA AGC
CTC CTT ATT CGA GCC GAG CTG GGC CAG CCA GGC AAC CTT CTA GGT AAC GAC
CAC ATC TAC AAC GTT ATC GTC ACA GCC CAT GCA TTT GTA ATA ATC TTC TTC
ATA GTA ATA CCC ATC ATA ATC GGA GGC TTT GGC AAC TGA CTA GTT CCC CTA
ATA ATC GGT GCC CCC GAT ATG GCG TTT CCC CGC ATA AAC AAC ATA AGC TTC
TGA CTC TTA CCT CCC TCT CTC CTA CTC CTG CTC GCA TCT GCT ATA GTG GAG
GCC GGA GCA GGA ACA GGT TGA ACA GTC TAC CCT CCC TTA GCA GGG AAC TAC
TCC CAC CCT GGA GCC TCC GTA GAC CTA ACC ATC TTC TCC TTA CAC CTA GCA
GGT GTC TCC TCT ATC TTA GGG GCC ATC AAT TTC ATC ACA ACA ATT ATC AAT
ATA AAA CCC CCT GCC ATA ACC CAA TAC CAA ACG CCC CTC TTC GTC TGA TCC
GTC CTA ATC ACA GCA GTC CTA CTT CTC CTA TCT CTC CCA GTC CTA GCT GCT
GGC ATC ACT ATA CTA CTA ACA GAC CGC AAC CTC AAC ACC ACC TTC TTC GAC
CCC GCC GGA GGA GGA GAC CCC ATT CTA TAC CAA CAC CTA TTC TGA TTT TTC
GGT CAC CCT GAA GTT TAT ATT CTT ATC CTA CCA GGC TTC GGA ATA ATC TCC
CAT ATT GTA ACT TAC TAC TCC GGA AAA AAA GAA CCA TTT GGA TAC ATA GGT
ATG GTC TGA GCT ATG ATA TCA ATT GGA TTC CTA GGG TTT ATC GTG TGA GCA
CAC CAT ATA TTT ACA GTA GGA ATA GAC GTA GAC ACA CGA GCA TAT TTC ACC
TCC GCT ACC ATA ATC ATC GCT ATC CCC ACC GGC GTC AAA GTA TTT AGC TGA
CTC GCC ACA CTC CAC GGA AGC AAT ATG AAA TGA TCT GCT GCA GTG CTC TGA
GCC CTA GGA TTC ATC TTT CTT TTC ACC GTA GGT GGC CTG ACT GGC ATT GTA
TTA GCA AAC TCA TCA CTA GAC ATC GTA CTA CAC GAC ACG TAC TAC GTT GTA
GCC CAC TTC CAC TAT GTC CTA TCA ATA GGA GCT GTA TTT GCC ATC ATA GGA
GGC TTC ATT CAC TGA TTT CCC CTA TTC TCA GGC TAC ACC CTA GAC CAA ACC
TAC GCC AAA ATC CAT TTC ACT ATC ATA TTC ATC GGC GTA AAT CTA ACT TTC
TTC CCA CAA CAC TTT CTC GGC CTA TCC GGA ATG CCC CGA CGT TAC TCG GAC
TAC CCC GAT GCA TAC ACC ACA TGA AAC ATC CTA TCA TCT GTA GGC TCA TTC
ATT TCT CTA ACA GCA GTA ATA TTA ATA ATT TTC ATG ATT TGA GAA GCC TTC
GCT TCG AAG CGA AAA GTC CTA ATA GTA GAA GAA CCC TCC ATA AAC CTG GAG
TGA CTA TAT GGA TGC CCC CCA CCC TAC CAC ACA TTC GAA GAA CCC GTA TAC
ATA AAA TCT AGA

CAAAAAAGGA AGGAATCGAA CCCCCCAAAG CTGGTTTCAA GCCAACCCCA
TGGCCTCCAT GACTTTTTCA AAAGGTATT

*Fig. 1*

COX 2  5'-END NON-CODING REGION,
       CODING REGION 7586-8269,
       AND 3'-END NON-CODING REGION

AGGTATTAGA AAAACCATTT CATAACTTTG TCGTCAAAGT TAAATTATAG
GCTAAATCCT ATATATCTTA

ATG GCA CAT GCA GCG CAA GTA GGT CTA CAA GAC GCT ACT TCC CCT ATC ATA
GAA GAG CTT ATC ACC TTT CAT GAT CAC GCC CTC ATA ATC ATT TTC CTT ATC
TGC TTC CTA GTC CTG TAT GCC CTT TTC CTA ACA CTC ACA ACA AAA CTA ACT
AAT ACT AAC ATC TCA GAC GCT CAG GAA ATA GAA ACC GTC TGA ACT ATC CTG
CCC GCC ATC ATC CTA GTC CTC ATC GCC CTC CCA TCC CTA CGC ATC CTT TAC
ATA ACA GAC GAG GTC AAC GAT CCC TCC CTT ACC ATC AAA TCA ATT GGC CAC
CAA TGG TAC TGA ACC TAC GAG TAC ACC GAC TAC GGC GGA CTA ATC TTC AAC
TCC TAC ATA CTT CCC CCA TTA TTC CTA GAA CCA GGC GAC CTG CGA CTC CTT
GAC GTT GAC AAT CGA GTA GTA CTC CCG ATT GAA GCC CCC ATT CGT ATA ATA
ATT ACA TCA CAA GAC GTC TTG CAC TCA TGA GCT GTC CCC ACA TTA GGC TTA
AAA ACA GAT GCA ATT CCC GGA CGT CTA AAC CAA ACC ACT TTC ACC GCT ACA
CGA CCG GGG GTA TAC TAC GGT CAA TGC TCT GAA ATC TGT GGA GCA AAC CAC
AGT TTC ATG CCC ATC GTC CTA GAA TTA ATT CCC CTA AAA ATC TTT GAA ATA
GGG CCC GTA TTT ACC CTA TAG

CACCCCCTCT ACCCCCTCTA GAGCCCACTG TAAAGCTAAC TTAGCATTAA
CCTTTTAAGT TAAAGATTAA

*Fig. 2*

COX 3   5'-END NON-CODING REGION,
        CODING REGION 9207-9992,
        AND 3'-END NON-CODING REGION

TCGCTGTCGC CTTAATCCAA GCCTACGTTT TCACACTTCT AGTAAGCCTC
TACCTGCACG ACAACACATA

ATG ACC CAC CAA TCA CAT GCC TAT CAT ATA GTA AAA CCC AGC CCA TGA CCC
CTA ACA GGG GCC CTC TCA GCC CTC CTA ATG ACC TCC GGC CTA GCC ATG TGA
TTT CAC TTC CAC TCC ATA ACG CTC CTC ATA CTA GGC CTA CTA ACC AAC ACA
CTA ACC ATA TAC CAA TGA TGG CGC GAT GTA ACA CGA GAA AGC ACA TAC CAA
GGC CAC CAC ACA CCA CCT GTC CAA AAA GGC CTT CGA TAC GGG ATA ATC CTA
TTT ATT ACC TCA GAA GTT TTT TTC TTC GCA GGA TTT TTC TGA GCC TTT TAC
CAC TCC AGC CTA GCC CCT ACC CCC CAA TTA GGA GGG CAC TGG CCC CGA ACA
GGC ATC ACC CCG CTA AAT CCC CTA GAA GTC CCA CTC CTA AAC ACA TCC GTA
TTA CTC GCA TCA GGA GTA TCA ATC ACC TGA GCT CAC CAT AGT CTA ATA GAA
AAC AAC CGA AAC CAA ATA ATT CAA GCA CTG CTT ATT ACA ATT TTA CTG GGT
CTC TAT TTT ACC CTC CTA CAA GCC TCA GAG TAC TTC GAG TCT CCC TTC ACC
ATT TCC GAC GGC ATC TAC GGC TCA ACA TTT TTT GTA GCC ACA GGC TTC CAC
GGA CTT CAC GTC ATT ATT GGC TCA ACT TTC CTC ACT ATC TGC TTC ATC CGC
CAA CTA ATA TTT CAC TTT ACA TCC AAA CAT CAC TTT GGC TTC GAA GCC GCC
GCC TGA TAC TGG CAT TTT GTA GAT GTG GTT TGA CTA TTT CTG TAT GTC TCC
ATC TAT TGA TGA GGG TCT TAC

TCTTTTAGTA TAAATAGTAC CGTTAACTTC CAATTAACTA GTTTTGACAA
CATTCAAAAA AGAGTAATAA

*Fig. 3*

Multiplex OLA of Mutant DNA

*Fig. 8*

METHODS FOR DETECTING MITOCHONDRIAL MUTATIONS DIAGNOSTIC FOR ALZHEIMER'S DISEASE AND METHODS FOR DETERMINING HETEROPLASMY OF MITOCHONDRIAL NUCLEIC ACID

CROSS-REFERENCE TO RELATED APPLICATIONS

This application is a continuation-in-part of application Ser. No. 08/614,072 filed Mar. 12, 1996, now abandoned, which is a continuation of application Ser. No. 08/219,842 filed Mar. 30, 1994, now U.S. Pat. No. 5,565,323; and this application is a continuation-in-part of application Ser. No. 08/410,658 filed Mar. 24, 1995, now abandoned.

FIELD OF THE INVENTION

The present invention relates generally to the diagnosis and treatment of Alzheimer's disease. More specifically, the invention relates to detecting genetic mutations in mitochondrial cytochrome c oxidase genes as a means for diagnosing the presence or risk of Alzheimer's disease.

BACKGROUND OF THE INVENTION

Alzheimer's disease (AD) is a progressive, neurodegenerative disorder that is incurable and untreatable, except symptomatically. Alzheimer's disease affects over 13 million people world-wide. Persons suffering from Alzheimer's disease may have one of two forms of this disease, familial AD or sporadic AD.

Familial Alzheimer's disease is an early-onset disease, generally occurring before the age of fifty, and accounts for only about 5 to 10% of all Alzheimer's cases. Familial AD is inherited and follows conventional patterns of Mendelian inheritance. This form of AD has been linked to nuclear chromosomal abnormalities.

In contrast, the second form of Alzheimer's disease, sporadic AD, is a late-onset disease which is not inherited or caused by nuclear chromosomal abnormalities. This late-onset form of the disease is the more common type of Alzheimer's disease and is believed to account for approximately 90 to 95% of all Alzheimer's cases. The cause of sporadic AD is not known.

It has been recognized that some degenerative diseases, such as Leber's hereditary optic neuropathy (LHON), myoclonic epilepsy lactic acidosis and stroke (MELAS), and myoclonic epilepsy ragged red fiber syndrome (MERRF), are transmitted through mitochondrial DNA defects. Mitochondrial DNA defects have also been implicated in explaining the apparently "sporadic" (nonmendelian) occurrence of some degenerative neurologic disorders, such as Parkinson's and Alzheimer's disease. Since all proteins encoded by the mitochondrial genome are components of the electron transport chain, deficits in electron transport function have been reported in Parkinson's and Alzheimer's disease. Of particular interest, it has been reported that defects in cytochrome c oxidase, an important terminal component of the electron transport chain located in the mitochondria of eukaryotic cells, may be involved in Alzheimer's disease.

Recent findings show that the catalytic activity, but not the physical levels of cytochrome c oxidase (COX), are decreased in the blood of individuals meeting the clinical criteria of probable Alzheimer's disease, or in the brains of patients who died with autopsy-confirmed AD. This suggests that COX is functionally abnormal in AD patients.

One report suggesting a relationship between AD and cytochrome c oxidase is Parker et al., *Neurology* 40: 1302–1303 (1990), which finds that patients with Alzheimer's disease have reduced cytochrome c oxidase activity. It has also been shown by Bennett et al., *J. Geriatric Psychiatry and Neurology* 5: 93–101 (1992), that when sodium azide, a specific inhibitor of cytochrome c oxidase was infused into rats, the rats suffered impaired memory and learning (a form of dementia). The rats mimicked the effect of Alzheimer's disease in humans. In addition, the sodium azide-tested rats failed to display long term potentiation, demonstrating loss of neuronal plasticity.

Despite these findings, the exact mechanism producing the electron transport dysfunctions is not known for Alzheimer's disease, nor has a genetic or structural basis for these dysfunctions been identified. Without knowing what causes these electron transport dysfunctions and in particular the genetic or structural basis, it is difficult to diagnose or treat Alzheimer's disease, especially the predominant form, sporadic AD.

To date, the diagnosis of probable Alzheimer's disease is by clinical observation and is a diagnosis of exclusion. A structured clinical approach is used to reduce the diagnostic error rate, but the accuracy of clinical diagnosis is rarely better than 70% to 80% in the hands of the most skilled neurologist, and less accurate when conducted outside specialized centers. Current clinical diagnostic practice is, at best 70%–80% specific. Clinical criteria do not rule out senile dementia of the Lewy Body Variant (SDLDB) (approximately 25% of all AD), a dementia form closely related to sporadic AD. In addition, multi-infarct dementia is very often over-reported. Unfortunately, definitive diagnosis can only be accomplished by pathological examination at autopsy. While attempts have been made to diagnose Alzheimer's disease by identifying differences in certain biological markers, including protease nexin II and apolipoprotein E alleles, this approach has not been successful. Incomplete penetrance in AD patients or crossover into normal or other disease populations makes identification of biological markers an unreliable method of diagnosis. Clearly, a reliable diagnosis of Alzheimer's at its earliest stages is critical for efficient and effective intercession and treatment of this debilitating disease. There exists a definite need for an effective diagnostic of Alzheimer's disease, and especially for the more prevalent form, sporadic AD. There exists a need for a non-invasive diagnostic that is reliable at or before the earliest manifestations of AD symptoms.

Not only does the Alzheimer's field currently lack a reliable, early means of detection, there is at present no effective therapy for AD, other than certain palliative treatments. Current therapies in clinical evaluation are designed to treat the symptoms of the disease and not impact the underlying pathology of AD. These therapies include Cognex, Velnacrine, E2020, and other similar agents known in the field. However, since the primary etiologic events in AD are not yet known in the art, rational therapies have not been designed. There exists a need for effective therapies, particularly those that address the primary cause of AD.

The present invention satisfies these needs for a useful diagnostic test for the risk or presence of Alzheimer's disease and provides related advantages as well.

SUMMARY OF THE INVENTION

The present invention relates to the identification and quantification of genetic mutations in mitochondrial genes which segregate with Alzheimer's disease. The invention provides methods for detecting and quantifying such mutations as a diagnostic for Alzheimer's disease, either before or after the onset of clinical symptoms. More specifically, the present invention provides a method for detecting the presence or risk of Alzheimer's disease by obtaining a biological sample containing mitochondria from a subject and determining the presence of at least one mutation in the sequence of a mitochondrial cytochrome c oxidase gene which correlates with the presence or risk of Alzheimer's disease. The present invention also encompasses a method of detecting the genetic mutations which cause a predisposition to Alzheimer's disease, by first determining the sequence of mitochondrial cytochrome c oxidase genes from subjects known to have Alzheimer's disease, second, comparing the sequence to that of the known wildtype mitochondrial genes, and lastly, identifying mutations in the patients or tissues collected at autopsy. The present invention also involves isolated nucleic acid sequences which are useful in the above mentioned diagnostics, namely those which correspond, or are complementary, to portions of mitochondrial genes, and where the sequences contain gene mutations which correlate with the presence or risk of Alzheimer's disease.

BRIEF DESCRIPTION OF THE FIGURES

FIG. 1 lists the 5' end upstream non-coding region and the complete nucleic acid sequence encoding mitochondrial cytochrome c oxidase subunit 1 (SEQ. ID NO. 1). The underlined sequences indicate the primers used for sequencing the nucleic acid sequence.

FIG. 2 lists the 5' end non-coding region and the complete nucleic acid sequence of the mitochondrial cytochrome c oxidase subunit 2 coding region (SEQ. ID NO. 2). The underlined sequences indicate the primers used for sequencing the nucleic acid sequence.

FIG. 3 lists the 5' end non-coding region and the complete nucleic acid sequence of the mitochondrial cytochrome c oxidase subunit 3 coding region (SEQ ID NO:82). The underlined sequences indicate the primers used for sequencing the nucleic acid sequence.

FIG. 8 is a chart showing the location of several missense point mutations and silent point mutations commonly found in the COX 2 gene of AD patients.

DETAILED DESCRIPTION OF THE INVENTION

Figure 4A:
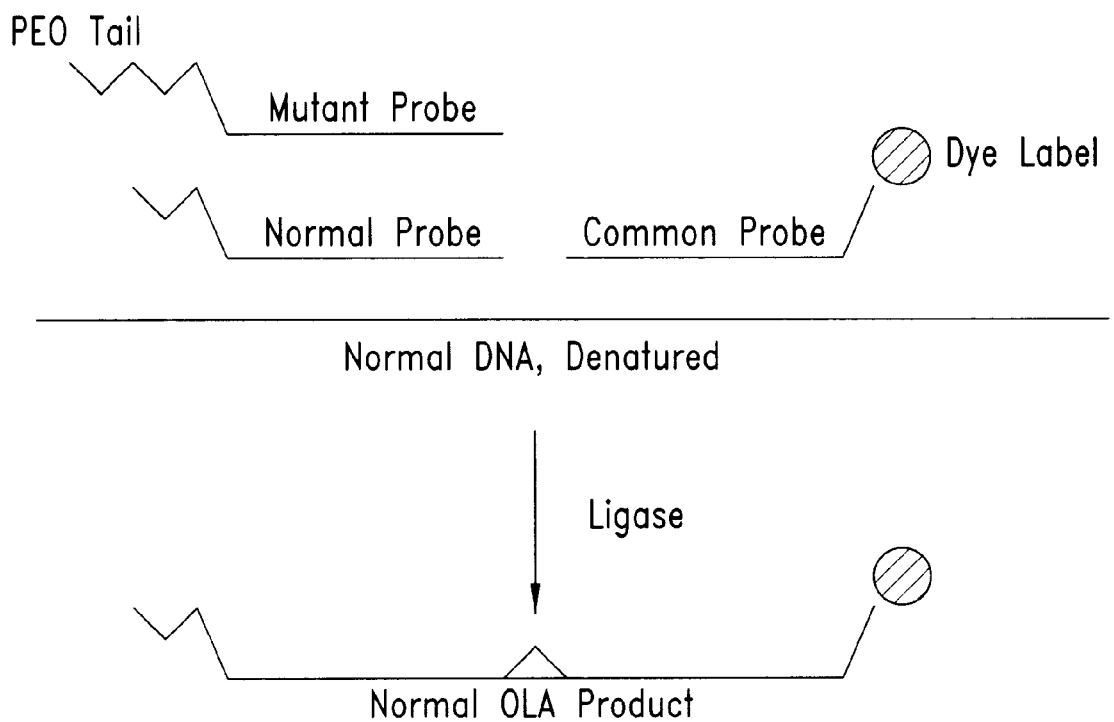
FIG. 4A is a schematic drawing of a multiplex analysis of normal DNA by oligonucleotide ligation assay (OLA).

The present invention relates to genetic mutations in mitochondrial genes which segregate with mitochondria-associated Alzheimer's disease. The invention provides methods for detecting and quantitating such mutations, as a diagnostic for Alzheimer's disease, either before or after the onset of clinical symptoms. Moreover, the invention also pertains to suppression of the undesired biological activity of the mutations and thus affords a therapeutic treatment for Alzheimer's disease. The invention provides the first effective diagnostic of Alzheimer's disease which is reliable at or before the earliest manifestations of AD symptoms.

Cytochrome c oxidase (COX) is an important terminal component of the electron transport chain located in the mitochondria of eukaryotic cells. Cytochrome c oxidase, also known as complex IV of the electron transport chain, is composed of at least thirteen subunits. At least ten of these subunits are encoded in nuclear genes; the remaining three subunits (1, 2, and 3) are encoded by mitochondrial genes. Mitochondrial DNA (mtDNA) is a small circular DNA that is approximately 17 Kb long in humans. The mtDNA encodes for two ribosomal RNAs (rRNA), a complete set of transfer RNAs (tRNA), and thirteen proteins, including the three cytochrome c oxidase subunits COX 1, COX 2, and COX 3.

Most of the mtDNA present in an individual is derived from the mtDNA contained within the ovum at the time of the individual's conception. Mutations in mtDNA sequence which affect all copies of mtDNA in an individual are known as homoplasmic. Mutations which affect only some copies of mtDNA are known as heteroplasmic and vary between different mitochondria in the same individual.

Each cell in an individual can contain hundreds of mitochondria and each mitochondria can contain multiple copies of the mitochondrial genome. Cells can harbor mixtures of mutant and normal mtDNA (heteroplasmy). During germ-line division (meiosis), mutant and normal mitochondria are randomly segregated into daughter cells. Random segregation of mitochondria during meiosis assures that the proportion of mutant to normal mitochondria within a daughter cell will vary. Because the severity of mitochondrial disease is a product of the nature of the mtDNA mutation, i.e., not all mutations will have a similar impact on function and the proportion of mutant mitochondria in a cell, random segregation of mtDNA causes mitochondrial diseases to appear sporadically in families with variable phenotypes. offspring derived from a daughter cell acquiring a predominance of normal mitochondria will not express the disease whereas offspring derived from a daughter cell acquiring a predominance of mutant mitochondria will be severely affected. Gradations between these two extremes are also observed.

In the present invention, mtDNA from both normal individuals and known Alzheimer's patients has been isolated, cloned and sequenced. As expected, some non-deleterious and apparently random mutations in each gene including some from normal (non-AD) individuals, were observed. However, in the AD patients, a small number of deleterious heteroplasmic mutations at common sites were noted to be routinely elevated, as well as a number of silent mutations at common sites. For the three mitochondrial COX subunits, the mutations occurred in one or more of the subunit clones for each individual. Such mutations were especially observed in the expressed regions of COX subunits 1 and 2 of the mtDNA.

The term "silent mutations" is used herein to mean point mutations that do not result in a change in the primary structure of the protein encoded by the DNA containing the point mutation. For example, a point mutation that alters the codon TG$\underline{T}$, which codes for the amino acid cysteine, to the codon TG$\underline{C}$, will still result in a cysteine residue due to the degeneracy of the genetic code. Hence, although the nucleotide sequence is altered, the mutation is silent because the encoded protein is unaltered.

The term "missense mutation" is used herein in its ordinary sense to mean a mutation that changes a codon coding for one amino acid to a codon corresponding to another amino acid.

According to the present invention, such missense and silent mutations in COX genes segregate with and, depending on the mutational burden, are possibly sufficient for, Alzheimer's disease. Sporadic AD, which accounts for at least 90% of all AD patients, is segregated with deleterious heteroplasmic mutation(s) in the mtDNA-encoded COX subunits. Detection of the deleterious mutations, therefore, is both predictive and diagnostic of Alzheimer's disease. Moreover, detection of the several silent mutations, which have been shown to segregate with Alzheimer's disease, is also predictive and diagnostic of the disease.

Suppressing the effects of the deleterious mutations through antisense technology provides an effective therapy of AD. Much is known about antisense therapies targeting messenger RNA (mRNA) or nuclear DNA. The diagnostic test of the present invention is useful to determine which of the specific AD mutations exist in a particular AD patient; this allows for "custom" treatment of the patient with antisense oligonucleotides only for the detected mutations. This patient-specific antisense therapy is also novel, and minimizes the exposure of the patient to any unnecessary antisense therapeutic treatment.

Blood and brain samples were harvested and DNA isolated from a number of clinically-classified or autopsy confirmed AD patients, and from a number of documented age-matched normal control individuals (elderly individuals with no history of AD or any sign of clinical symptoms of AD) or age-matched neurodegenerative disease controls (patients with Huntington's disease, supranuclear palsy, etc.). After cloning of cytochrome c oxidase (COX) gene fragments, the sequences of multiple clones from each patient were obtained. Compilation of the sequences were made, aligned, and compared with the published DNA sequence (Anderson et al., Nature 290: 457–465 (1981)) for known normal mitochondrial DNA (Cambridge sequence). The published COX coding sequences are numbered as follows: COX 1 is nucleotides 5904 to 7445, COX 2 is nucleotides 7586 to 8269, and COX 3 is nucleotides 9207 to 9992. All reference hereinbelow is made only to the published Cambridge sequence.

Any variation (mutation, insertion, or deletion) from published sequences was verified by replication and complementary strand sequencing. Comparison of the sequence data with the Cambridge sequence revealed sets of common mutations that appear linked together within distinct mtDNA alleles. Analysis of the variations in known AD patients indicated a significant number of mutations. Some of the mutations observed were silent mutations resulting in no amino acid changes in the expressed protein. However, a number of mutations present would result in amino acid changes in the corresponding protein. In many instances the corresponding amino acid change would also lead to conformational changes to the COX enzyme.

In cytochrome c oxidase subunit 2, for example, the sequence in AD patients varied from the normal sequence in at least one base per gene. The data are summarized in Table 1. Several of the recurrent mutations observed would result in conformational alteration of the COX enzyme. Mutation of the normal C at nucleotide number 7650 to T results in a change from the normal hydrophilic threonine (Thr) to a hydrophobic isoleucine (Ile) at codon 22 of COX subunit 2. Changes of this type in nucleic acid structure, particularly when occurring in highly conserved areas, are known to disrupt or modify enzymatic activity.

Missense Mutations Observed in COX 1 Gene of Alzheimer's Patients

Table 2 below provides examples of some mutations of mitochondrial cytochrome c oxidase subunit 1 (COX 1) gene is for each Alzheimer's patient. The mutations listed for the AD patients are relative to the published Cambridge sequence for normal human COX 1. The nucleotide number indicated is determined in a conventional manner from the open reading frame at the 5'-end of the gene.

TABLE 1

| NUCLEOTIDE # | | | 7650 | 7705 | 7810 | 7868 | 7891 | 7912 | 8021 |
|---|---|---|---|---|---|---|---|---|---|
| AMINO ACID WT | | | Thr | Tyr | Leu | Leu | His | Glu | Ile |
| AMINO ACID MT | | | Ile | Tyr | Leu | Phe | His | Glu | Val |
| NUCLEOTIDE WT | | | C | T | C | C | C | G | A |
| NUCLEOTIDE MT | | | T | C | T | T | T | A | G |
| PATIENT | AG# | Diagnosis | Clone # | | | | | | |
| 3A6_KE | 8 | AD | Clone 1 | − | − | − | − | − | − | − |
| | | | Clone 2 | − | − | − | − | − | − | − |
| | | | Clone 3 | − | − | − | − | − | − | − |
| | | | Clone 4 | − | − | − | + | − | − | − |
| | | | Clone 5 | + | − | − | + | − | − | + |
| | | | Clone 6 | − | − | − | − | − | − | − |
| | | | Clone 7 | + | + | + | + | + | + | + |
| | | | Clone 8 | − | − | − | − | − | − | − |

TABLE 1-continued

| | | | | | | | | | | |
|---|---|---|---|---|---|---|---|---|---|---|
| | | | Clone 9 | − | − | − | − | − | − | − |
| | | | Clone 10 | − | − | − | − | − | − | − |
| 3B1_RI | 10 | AD | Clone 1 | − | − | − | − | − | − | − |
| | | | Clone 2 | + | − | − | + | − | − | + |
| | | | Clone 3 | + | + | + | + | + | + | + |
| | | | Clone 4 | + | + | + | + | + | + | + |
| | | | Clone 5 | − | − | − | − | − | − | − |
| | | | Clone 6 | − | − | − | − | − | − | − |
| | | | Clone 7 | − | − | − | − | − | − | − |
| | | | Clone 8 | − | − | − | − | − | − | − |
| | | | Clone 9 | − | − | − | − | − | − | − |
| | | | Clone 10 | − | − | − | − | − | − | − |

As evidenced by Table 2, point mutations in the COX 1 gene, which are associated with AD are at nucleotide positions 6221, 6242, 6266, 6299, 6366, 6383, 6410, 6452, 6483, 6512, 6542, 6569, 6641, 6935, 6938 and 7146.

Missense Mutations Observed in COX 2 Gene of Alzheimer's Patients

Table 1 above is an example of some mutations observed in ten clones of the mitochondrial cytochrome c oxidase subunit 2 (COX 2) gene of Alzheimer's patients. The mutations listed for the AD patients are relative to the published Cambridge sequence for normal human COX 2. The nucleotide number indicated is determined in a conventional manner from the open reading frame at the 5'-end of the gene.

TABLE 2

| Nucleotide # | 6221 | 6242 | 6266 | 6299 | 6366 | 6383 | 6410 | 6452 | 6483 | 6512 | 6542 | 6569 | 6641 | 6935 | 6938 | 7146 |
|---|---|---|---|---|---|---|---|---|---|---|---|---|---|---|---|---|
| Amino Acid WT | Pro | Leu | Gly | Phe | Val | Gly | Ile | Leu | Leu | Ala | Arg | Pro | Leu | Phe | Ile | Thr |
| Amino Acid MT | Pro | Leu | Gly | Phe | Ile | Gly | Ile | Leu | Phe | Ala | Arg | Pro | Leu | Phe | Ile | Ala |
| Nucleotide WT | T | C | A | A | G | G | C | C | C | T | C | C | T | C | C | A |
| Nucleotide MT | C | T | C | G | A | A | T | T | T | C | T | A | C | T | T | G |

| Patient | AG# | Diagnosis | | 6221 | 6242 | 6266 | 6299 | 6366 | 6383 | 6410 | 6452 | 6483 | 6512 | 6542 | 6569 | 6641 | 6935 | 6938 | 7146 |
|---|---|---|---|---|---|---|---|---|---|---|---|---|---|---|---|---|---|---|---|
| 3A6_KE | 8 | AD | Clone 1 | − | − | − | − | − | − | − | − | − | − | − | − | − | − | − | − |
| | | | Clone 2 | − | − | − | − | − | − | − | − | − | − | − | − | − | − | − | − |
| | | | Clone 3 | − | − | − | − | − | − | − | − | − | − | − | − | − | − | − | − |
| | | | Clone 4 | − | − | − | − | − | − | − | − | − | − | − | − | − | − | − | − |
| | | | Clone 5 | − | − | − | − | − | − | − | − | − | − | − | − | − | − | − | − |
| | | | Clone 6 | + | − | + | + | + | + | + | + | − | + | + | + | + | + | + | + |
| | | | Clone 7 | − | − | − | − | − | − | − | − | − | − | − | − | − | − | − | − |
| | | | Clone 8 | − | − | − | − | − | − | − | − | − | − | − | − | − | − | − | − |
| | | | Clone 9 | − | − | − | − | − | − | − | − | − | − | − | − | − | − | − | − |
| | | | Clone 10 | + | + | + | + | + | + | + | + | + | + | + | + | + | + | + | + |
| 3A6_KE | B | AD | Clone 1 | − | − | − | − | − | − | − | − | − | − | − | − | − | − | − | − |
| | | | Clone 2 | + | + | + | + | + | + | + | + | + | + | + | + | + | + | + | + |
| | | | Clone 3 | + | − | − | + | − | − | + | + | − | + | − | + | + | + | + | + |
| | | | Clone 4 | + | + | + | + | + | + | + | + | + | + | + | + | + | + | + | + |
| | | | Clone 5 | + | + | + | + | + | + | + | + | + | + | + | + | + | + | + | + |
| | | | Clone 6 | + | − | − | + | + | + | + | + | + | + | + | + | + | + | + | + |
| | | | Clone 7 | + | + | + | + | + | + | + | + | − | + | + | + | + | + | + | − |
| | | | Clone 8 | + | + | + | + | + | + | + | + | + | + | + | + | + | + | + | + |
| | | | Clone 9 | + | + | + | + | + | + | + | + | + | + | + | + | + | + | + | + |
| | | | Clone 10 | − | − | − | − | − | − | − | − | − | − | − | − | − | − | − | − |

As evidenced by Table 1, point mutations in the COX 2 gene which are associated with AD are located at nucleotide positions 7650, 7705, 7810, 7868, 7891, 7912 and 8021.

Figure 7:
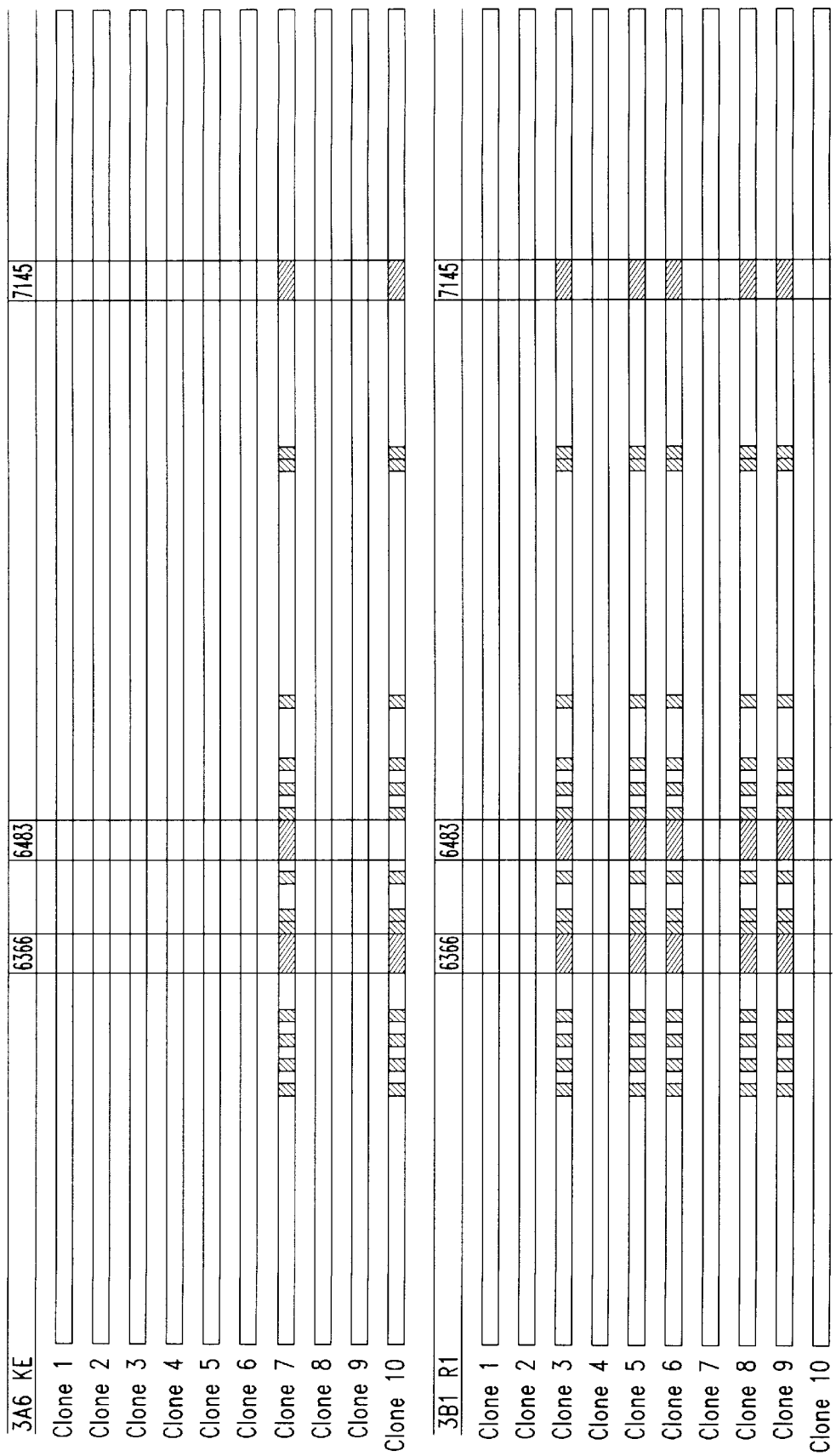
FIG. 7 is a chart showing the location of several missense point mutations and silent point mutations commonly found in the COX 1 genes of AD patients.
Figure 8:
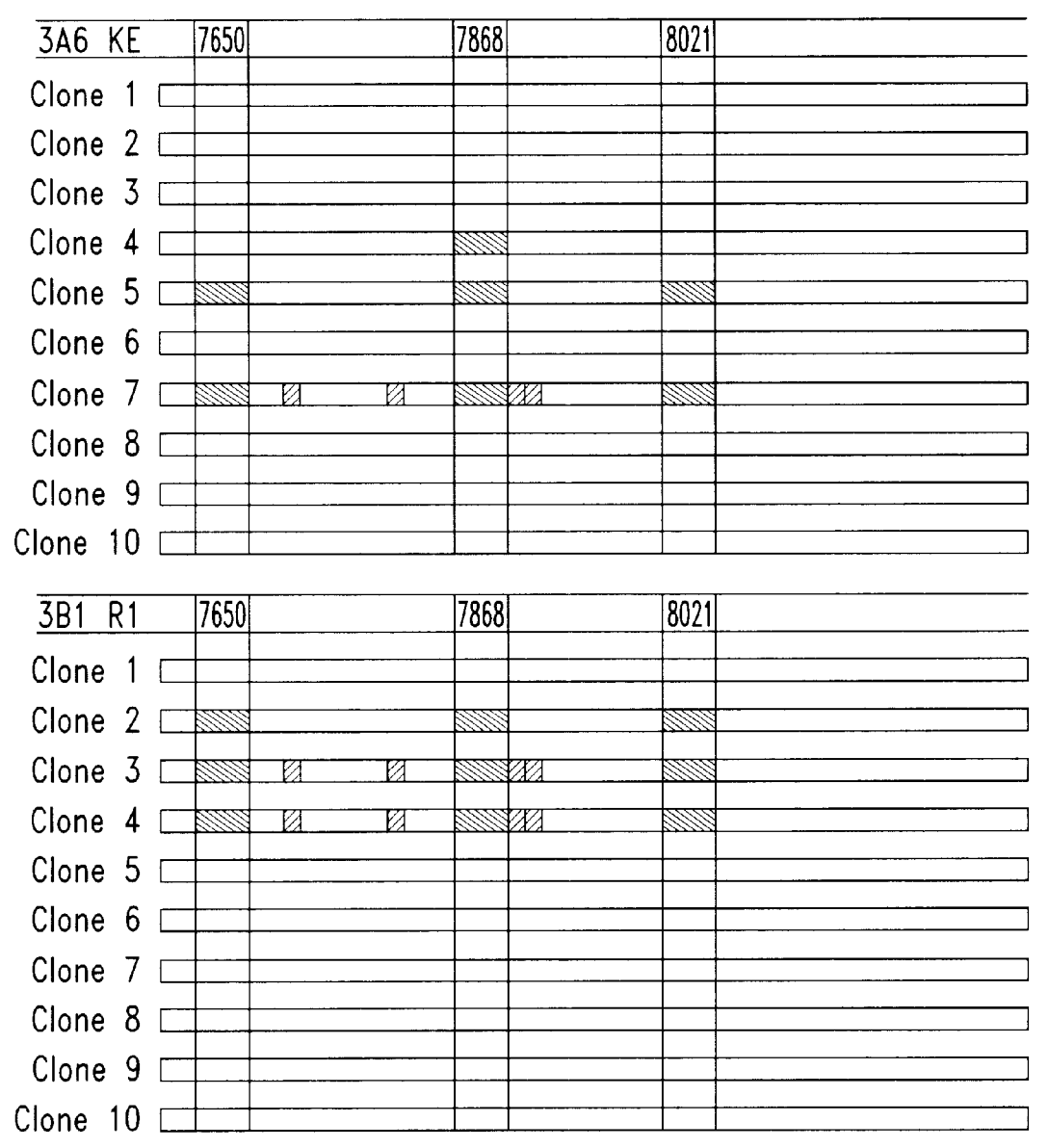
Figure 9:
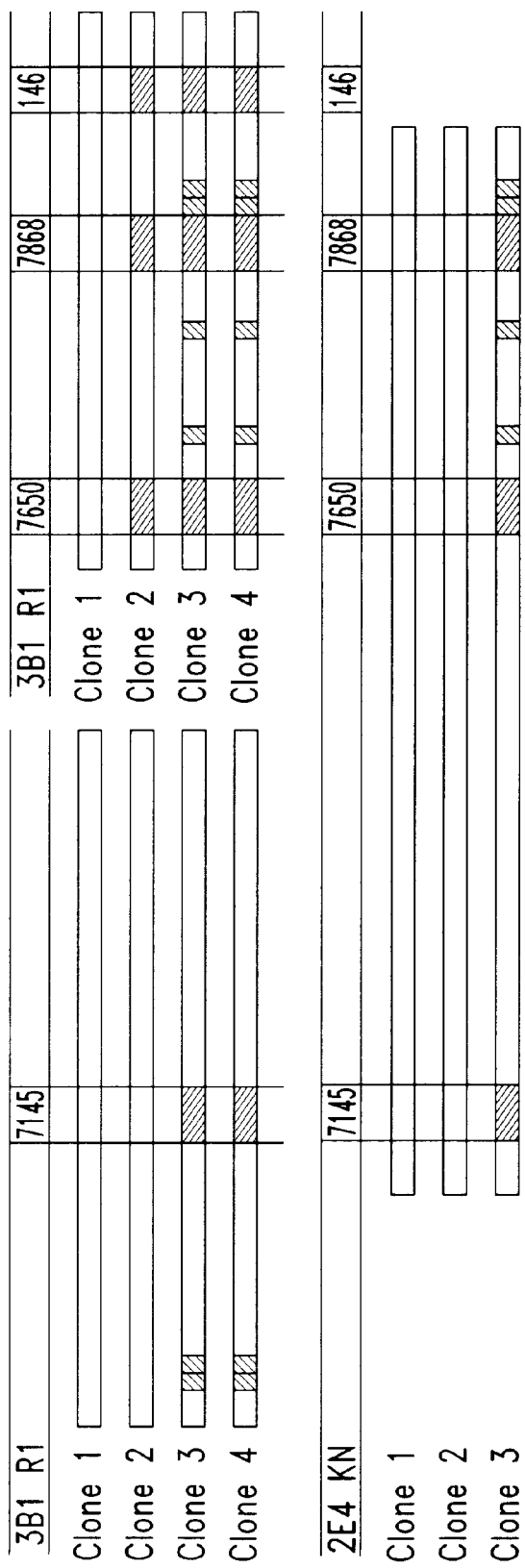
FIG. 9 is a chart showing the linkage of missense point mutations and silent point mutations in the COX 1 and COX 2 genes of AD patients.

Sequencing analyses of multiple clones of the COX 1, COX 2 and COX 3 genes reveal that these AD-associated mutations are linked, and appear on the same mitochondrial DNA molecule (see FIGS. 7 and 8). Data obtained from sequence analysis of full length genes and mutational linkage analysis suggest that the COX genes of an individual may exist as wild type and as distinct mutant DNA molecules that carry an array of point mutations. PCR-amplified fragments of DNA spanning a portion of both the COX 1 and COX 2 genes and the intervening tRNA genes reveal that the point mutations, both silent and missense, which were identified in COX 1 and 2 genes, are linked as well within the same mitochondrial DNA molecule (FIG. 9).

The above-discussed findings indicate that AD shares the hallmark of other mitochondrial diseases. Mitochondria are unique cytoplasmic organelles distributed in all cells whose principal function is to generate energy-rich ATP molecules necessary for driving cellular biochemical processes. Mitochondria contain their own DNA that is separate and distinct from chromosomal DNA. Mitochondrial DNA (mtDNA) encodes exclusively for a number of critical protein subunits of the electron transport chain and the structural rRNAs and tRNAs necessary for the expression of these proteins. Unlike chromosomal DNA, each cell contains 1 to 100,000 copies of mtDNA. Cells can harbor mixtures of wild-type and mutant mtDNA (heteroplasmy). Mitochondrial genes are dynamic and the mtDNA genotype can drift towards increased mtDNA mutational burden in heteroplasmic cellular populations. The metabolic phenotype can deteriorate with time under these conditions, and can result in disease manifestation once the mutational burden exceeds a critical threshold in effected tissue, leading to bioenergetic failure and eventually cell death.

The invention also includes the isolated nucleotide sequences which correspond to or are complementary to portions of mitochondrial cytochrome c oxidase genes which contain gene mutations that correlate with the presence of Alzheimer's disease. The isolated nucleotide sequences which contain missense gene mutations include COX 1 nucleotides 5903 to 7445, COX 2 nucleotides 7586 to 8269 and COX 3 nucleotides 9207 to 9992. The isolated nucleotide sequences which contain silent mutations that segregate with Alzheimer's disease have at least one silent mutation located at COX 1 nucleotides 6221, 6242, 6266, 6299, 6383, 6410, 6452, 6483, 6512, 6542, 6569, 6641, 6935, 6938, and combinations thereof, at least one silent mutation in COX 2 nucleotides 7650, 7705, 7810, 7891 or 7912, and combinations thereof or a combination of at least one silent mutation in COX 1 and COX 2 at the nucleotide site discussed above.

Diagnostic Detection of Alzheimer's Disease-Associated Mutations

According to the present invention, base changes in the mitochondrial COX genes can be detected and used as a diagnostic for Alzheimer's disease. A variety of techniques are available for isolating DNA and RNA and for detecting mutations in the isolated mitochondrial COX genes.

A number of sample preparation methods are available for isolating DNA and RNA from patient blood samples. For example, the DNA from a blood sample may be obtained by cell lysis following alkali treatment. Most preferably, total nucleic acid is obtained by lysis of white blood cells resuspended in water by incubation of cells in a boiling water bath for about 10 minutes. After cooling, cellular debris is removed, such as by centrifugation at about 14,000 g for about two minutes. The clear supernatant, which contains the DNA, may be stored frozen, e.g., about −80° C.

It has been found that the conventional proteinase K/phenol-chloroform method of isolating DNA is inadequate for the isolation of the mutant DNA, and yields lower amounts of DNA. Also, oxidation by reactive oxygen species generated by the electron transport chain in the mitochondria may lead to crosslinking of the DNA. Therefore, conventional methods are inappropriate for mutant mtDNA isolation.

As discussed more fully hereinbelow, hybridization with one or more labeled probes containing the variant sequences enables detection of the AD mutations. Since each AD patient can be heteroplasmic (possessing both the AD mutation and the normal sequence) a quantitative or semi-quantitative measure (depending on the detection method) of such heteroplasmy can be obtained by comparing the amount of signal from the AD probe to the amount from the AD (normal) probe.

Various techniques, as discussed more fully hereinbelow, are available for detecting the specific mutations in the mitochondrial COX genes. The detection methods include, for example, cloning and sequencing, ligation of oligonucleotides, use of the polymerase chain reaction and variations thereof, use of single nucleotide primer-guided extension assays, hybridization techniques using target-specific oligonucleotides and sandwich hybridization methods.

Cloning and sequencing of the COX genes can serve to detect AD mutations in patient samples. Sequencing can be carried out with commercially available automated sequencers utilizing fluorescently labeled primers. An alternate sequencing strategy is the "sequencing by hybridization" method using high density oligonucleotide arrays on silicon chips (Fodor et al., Nature 364: 555–556 (1993); Fodor et al., Science 251: 767–773 (1991)). Fluorescently-labeled target nucleic acid generated, for example from PCR amplification of the target genes using fluorescently labeled primers or nucleotides, can be hybridized with a chip containing a set of short oligonucleotides which probe regions of complementarity with the target sequence. The resulting hybridization patterns can be used to reassemble the original target DNA sequence.

Mutational analysis can also be carried out by methods based on ligation of oligonucleotide sequences which anneal immediately adjacent to each other on a target DNA or RNA molecule (Wu and Wallace, Genomics 4: 560–569 (1989); Landren et al., Science 241: 1077–1080 (1988); Nickerson et al., Proc. Natl. Acad. Sci. 87: 8923–8927 (1990); Barany, F., Proc. Natl. Acad. Sci. 88: 189–193 (1991)). Ligase-mediated covalent attachment occurs only when the oligonucleotides are correctly base-paired. The Ligase Chain Reaction (LCR) and the oligonucleotide ligation assay (OLA), which utilize the thermostable Tag ligase for target amplification, are particularly useful for interrogating AD mutation loci. The elevated reaction temperatures permit the ligation reaction to be conducted with high stringency (Barany, F., PCR Methods and Applications 1: 5–16 (1991)) (Grossman, P. D. et al., Nucl. Acids. Res. 22: 4527–4534, (1994)).

Analysis of point mutations in DNA can also be carried out by using the polymerase chain reaction (PCR) and variations thereof. Mismatches can be detected by competitive oligonucleotide priming under hybridization conditions where binding of the perfectly matched primer is favored (Gibbs et al., *Nucl. Acids. Res.* 17: 2437–2448 (1989)). In the amplification refractory mutation system technique (ARMS), primers can be designed to have perfect matches or mismatches with target sequences either internal or at the 3' residue (Newton et al., *Nucl. Acids. Res.* 17: 2503–2516 (1989)). Under appropriate conditions, only the perfectly annealed oligonucleotide can function as a primer for the PCR reaction, thus providing a method of discrimination between normal and mutant (AD) sequences.

Genotyping analysis of the COX genes can also be carried out using single nucleotide primer-guided extension assays, where the specific incorporation of the correct base is provided by the high fidelity of the DNA polymerase (Syvanen et al., *Genomics* 8: 684–692 (1990); Kuppuswamy et al., *Proc. Natl. Acad. Sci. U.S.A.* 88: 1143–1147 (1991)).

Detection of single base mutations in target nucleic acids can be conveniently accomplished by differential hybridization techniques using allele-specific oligonucleotides (Suggs et al., *Proc. Natl. Acad. Sci.* 78: 6613–6617 (1981); Conner et al., *Proc. Natl. Acad. Sci.* 80: 278–282 (1983); Saiki et al., *Proc. Natl. Acad. Sci.* 86: 6230–6234 (1989)). Mutations can be diagnosed on the basis of the higher thermal stability of the perfectly matched probes as compared to the mismatched probes. The hybridization reactions can be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection of the COX genes by sandwich hybridization methods. In this strategy, the mutant and wildtype (normal) target nucleic acids are separated from non-homologous DNA/RNA using a common capture oligonucleotide immobilized on a solid support and detected by specific oligonucleotide probes tagged with reporter labels. The capture oligonucleotides can be immobilized on microtitre plate wells or on beads (Gingeras et al., *J. Infect. Dis.* 164: 1066–1074 (1991); Richman et al., *Proc. Natl. Acad. Sci.* 88: 11241–11245 (1991)).

Another method for analysis of a biological sample for specific mutations in the COX genes is a multiplexed primer extension method. In this method primer is hybridized to nucleic acid suspected of containing a mutation such that the primer is hybridized 3' to the suspected mutation. The primer is extended in the presence of a mixture of one to three deoxynucleoside triphosphates and one of three chain terminating deoxynucleoside triphosphates selected such that the wild-type extension product, the mutant DNA-derived extension product and the primer each are of different lengths. These steps can be repeated, such as by PCR or RT-PCR, and the resulting primer extended products and primer are then separated on the basis of molecular weight to thereby enable identification of mutant DNA-derived extension product.

The multiplexed primer extension method may also be used to analyse the heteroplasmy of multiple genetic mutations relative to corresponding wild-type sequences within a sample. In this method, two or more differentiable primers to a nucleic acid suspected of having genetic mutations are hybridized 3' to the location of the suspected mutations. The primers are extended in the presence of a mixture of one to three deoxynucleoside triphosphates and one to three chain terminating deoxynucleoside triphosphates such that for each of the two or more differentiable primers, the corresponding wild-type extension product and the corresponding mutant DNA-derived product differ in length from each other and the primer. After several rounds of extension the products are separated on the basis of molecular weight and mutant DNA extension products identified. Preferably, a high fidelity DNA polymerae is used in the extension reactions.

While radio-isotopic labeled detection oligonucleotide probes are highly sensitive, non-isotopic labels are preferred due to concerns about handling and disposal of radioactivity. A number of strategies are available for detecting target nucleic acids by non-isotopic means (Matthews et al., *Anal. Biochem.*, 169: 1–25 (1988)). The non-isotopic detection method can be direct or indirect.

The indirect detection process generally involves the use of an oligonucleotide probe that is covalently labeled with a hapten or ligand, such as digoxigenin (DIG) or biotin, for example. Following the hybridization step, the target-probe duplex is detected by an antibody- or streptavidin-enzyme complex. Enzymes commonly used in DNA diagnostics are horseradish peroxidase and alkaline phosphatase. One particular indirect method, the Genius™ detection system (Boehringer Mannheim) is especially useful for mutational analysis of the mitochondrial COX genes. This indirect method uses digoxigenin as the tag for the oligonucleotide probe and is detected by an anti-digoxigenin-antibody-alkaline phosphatase conjugate.

Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes. Examples of lanthanide chelates include complexes of $Eu^{3+}$ and $Tb^{3+}$. Directly labeled oligonucleotide-enzyme conjugates are preferred for detecting point mutations when using target-specific oligonucleotides as they provide very high sensitivities of detection.

Oligonucleotide-enzyme conjugates can be prepared by a number of methods (Jablonski et al., *Nucl. Acids Res.*, 14: 6115–6128 (1986); Li et al., *Nucl. Acids. Res.*, 15: 5275–5287 (1987); Ghosh et al., *Bioconjugate Chem.* 1: 71–76 (1990)), and alkaline phosphatase is the enzyme of choice for obtaining high sensitivities of detection. The detection of target nucleic acids using these conjugates can be carried out by filter hybridization methods or by bead-based sandwich hybridization (Ishii et al., *Bioconjugate Chemistry* 4: 34–41 (1993)).

Detection of the probe label can be accomplished by the following approaches. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide-chelate labels, fluorescent signals can be measured with spectrofluorimeters with or without time-resolved mode or using automated microtitre plate readers. With enzyme labels, detection is by color or dye deposition (p-nitrophenyl phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g. 4-methyl umbelliferyl phosphate for alkaline phosphatase) or chemiluminescence (the alkaline phosphatase dioxetane substrates LumiPhos 530 from Lumigen Inc., Detroit, Mich. or AMPPD and CSPD from Tropix, Inc.). Chemiluminescent detection can be carried out with x-ray or polaroid film or by using single photon counting luminometers. This is the preferred detection format for alkaline phosphatase labeled probes.

The detection oligonucleotide probes generally range in size between about 15 to about 30 bases in length. In order to obtain the required target discrimination using the detection oligonucleotide probes, the hybridization reactions are generally run between 20–60° C., and most preferably between 30–50° C. As known to those skilled in the art, optimal discrimination between perfect and mismatched duplexes can be obtained by manipulating the temperature and/or salt concentrations or inclusion of formamide in the stringency washes.

The heteroplasmy associated with the mitochondrial genome poses a major challenge in designing a DNA-based diagnostic test. Sequencing of the COX 1 and 2 genes reveal the existence of a unique mitochondrial DNA molecule which contains a constellation of missense and silent mutations. In addition, sequencing studies suggest an elevated mutational burden in sporadic AD that is associated with impaired cellular energy metabolism and disease phenotype. Therefore, a critical requirement to improved genetic detection of AD is the quantitation of mitochondrial DNA (mtDNA) heteroplasmy. While a number of methods have been cited above for mutation analysis, several of these techniques are inadequate for quantitating the proportion of mutant alleles at a disease-associated locus. For instance, traditional hybridization-based methods, such as allele-specific oligonucleotide (ASO) hybridization and allele-specific polymerase chain reaction, are limited in scope for detecting subtle differences in mutant allele frequencies. Typically, the utility of these methods is sequence-dependent. When applicable, the methods often require tailored optimization conditions for interrogating each mutation site for efficient discrimination of wildtype and mutant alleles. Mutation analysis by restriction fragment length polymorphism (RFLP) is best applicable when mutations cause a gain or loss of a restriction site. However, the technique lacks sensitivity for detecting mutant alleles which appear at low frequencies.

Figure 4B:
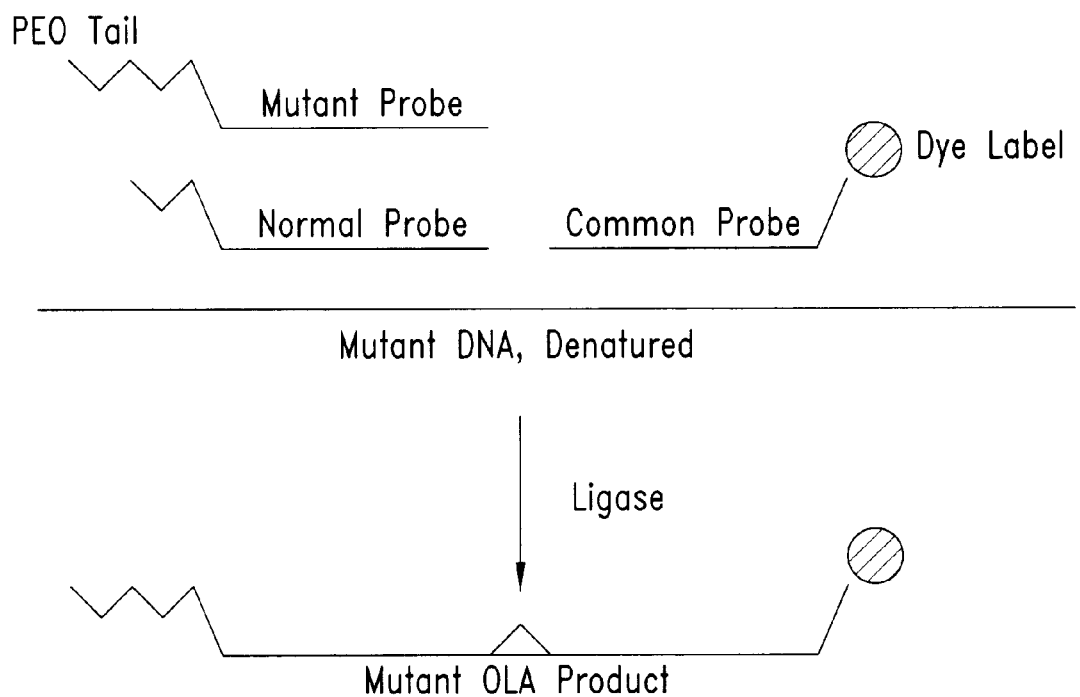
FIG. 4B is a schematic drawing of a multiplex analysis of a mutant DNA by oligonucleotide ligation assay.

In one aspect of the present invention, the oligonucleotide ligation assay (OLA) is applied for quantitative mutational analysis of mitochondrial DNA. In this embodiment of the invention, a thermostable ligase-catalyzed reaction is used to link a fluorescently labeled common probe with allele-specific probes. The latter probes are sequence-coded with non-nucleotide mobility modifiers which confer unique electrophoretic mobilities to the ligation products (FIGS. 4A and 4B). The oligonucleotide ligation assay is described in detail in Grossman, et al. (1994), Nuc. Acids Res. 22: 4527–4534, incorporated herein in its entirety by reference thereto.

Normal and mutant probes are synthesized with different oligomeric nucleotide or non-nucleotide modifier tails at their 5' termini. Examples of nucleotide modifiers are inosine or thymidine residues, whereas examples of non-nucleotide modifiers include pentaethyleneoxide (PEO) and hexaethyleneoxide (HEO) monomeric units. The non-nucleotide modifiers are preferred and most preferably, PEO is used to label the probes. When a DNA template is present, a thermostable DNA ligase catalyzes the ligation of normal and mutant probes to a common probe bearing a fluorescent label. The PEO tails modify the mobilities of the ligation products in electrophoretic gels. The combination of PEO tails and fluorophor labels (TET and FAM (5-carboxy-fluorescein derivatives)), HEX and JOE (6-carboxy-fluorescein derivatives), ROX (6-carboxy-x-rhodamine), or TAMRA (N, N, N', N'-tetramethyl-6-carboxy-rhodamine), for example, which are available from Perkin -Elmer, ABI Division, Foster City, Calif. permit multiplexing based on size and color by providing unique electrophoretic signatures to the ligation products. Since silent mutations appear together with the missense mutations, the silent mutations as well as the missense mutations can serve as AD-associated mucleotide sites. The products are separated by electrophoresis, and fluorescence intensities associated with wild-type and mutant products are used to quantitate heteroplasmy. Thus, wild-type and mutant sequences are detected and quantitated on the basis of size and fluorescence intensities of the ligation products. Importantly, this method may be configured for quantitative detection of multiple AD-associated mutations in a single ligation reaction.

For quantitative analysis of AD-associated mutations using OLA, oligonucleotide probes are preferably labeled with fluorophor labels that provide spectrally distinguishable characteristics. In a preferred embodiment, oligonucleotides are labeled with 5' oligomeric pentaethyleneoxide (PEO) tails. Synthesis of such 5' labeled oligonucleotides can be carried out, for example, using an automated synthesizer using standard phosphoramidite chemistry. Following cleavage from resin and deprotection with ammonium hydroxide, the $(PEO)_n$-oligonucleotides may be purified by reverse phase HPLC. Oligonucleotides with 3'-FAM or TET dyes (Perkin Elmer) and 5'-phosphates may be synthesized and purified by the procedure of Grossman, et al., (1994), *Nucl. Acids Res.*, 22: 4527–4534.

The 5'-PEO-labeled probes may be synthesized to have 5'-PEO-tails of differing lengths to facilitate distinguishing the ligated probe products both electrophoretically by size and by spectral characteristics of the fluorophor labels.

The oligonucleotide probes are used for interrogating AD-associated mutations, preferably at mtDNA nucleotide positions 6366, 6483, 7146, 7650, 7868 and 8021. The six oligonucleotide probe combinations for monitoring the mtDNA nucleotide positions are shown in Table 3. The oligonucleotide probes for the OLA assay are preferably designed to have calculated melting temperatures of about 40° C. to 50° C., most preferably about 48° C. by the nearest neighbor method (Breslaur, et al., (1986), *Proc. Natl. Acad. Sci. USA,* 83: 9373–9377) so that the ligation reaction may be performed at a temperature range of about 40° C. to 60° C., preferably from about 45° C. to about 55° C. The wild-type, mutant and common oligonucleotide probes are preferably synthesized with various combinations of pentaethyleneoxide (PEO) oligomeric tails and fluorescein dyes, such as TET and FAM. These combinations of mobility modifiers and fluorophor labels furnish electrophoretically unique ligation products that enable all six AD-associated nucleotide sites to be monitored in a single ligation reaction.

TABLE 3

OLA PRIMER COMBINATIONS FOR DETECTING AD-ASSOCIATED MUTATIONS

| GENE | BASE[a] | SUBSTITUTION[b] | SEQUENCE (5->3')[c] | STRAND/PROBE[d] | SEQUENCE NO. |
|---|---|---|---|---|---|
| COX 1 | 6366 | Val→Ile | (PEO)$_4$-CCTTACACCTAGCAGGTG | L/WT | Seq ID No. 3 |
| | | | (PEO)$_6$-TCCTTACACCTAGCAGGTA | L/MT | Seq ID No. 4 |
| | | | (PO$_4$)-TCTCCTCTATCTTAGGGGC-*TET* | L/COM | Seq ID No. 5 |
| COX 1 | 6483 | Leu→Phe | (PEO)$_4$-CCTAATCACAGCAGTCC | L/WT | Seq ID No. 6 |
| | | | (PEO)$_5$-TCCTAATCACAGCAGTCT | L/MT | Seq ID No. 7 |
| | | | (PO$_4$)-TACTTCTCCTATCTCTCCC-*FAM* | L/COM | Seq ID No. 8 |
| COX 1 | 7146 | Thr→Ala | (PEO)$_9$-CCAAAATCCATTTCA | L/WT | Seq ID No. 9 |
| | | | (PEO)$_{10}$-CCAAAATCCATTTCG | L/MT | Seq ID No. 10 |
| | | | (PO$_4$)-CTATCATATTCATCGGC-*FAM* | L/COM | Seq ID No. 11 |
| COX 2 | 7650 | Thr→Ile | (PEO)$_2$-ATCATAGAAGAGCTTATCAC | L/WT | Seq ID No. 12 |
| | | | (PEO)$_3$-ATCATAGAAGAGCTTATCAT | L/MT | Seq ID No. 13 |
| | | | (PO$_4$)-CTTTCATGATCACGC-*FAM* | L/COM | Seq ID No. 14 |
| COX 2 | 7868 | Leu→Phe | (PEO)$_2$-CAACGATCCCTCCC | L/WT | Seq ID No. 15 |
| | | | (PEO)$_3$-TCAACGATCCCTCCT | L/MT | Seq ID No. 16 |
| | | | (PO$_4$)-TTACCATCAAATCAATTG-*TET* | L/COM | Seq ID No. 17 |
| COX 2 | 8021 | Ile→Val | (PEO)$_4$-AATCGAGTACTCCCGA | L/WT | Seq ID No. 18 |
| | | | (PEO)$_6$-ATCGAGTAGTACTCCCGG | L/MT | Seq ID No. 19 |
| | | | (PO$_4$)-TTGAAGCCCCCATTC-*TET* | L/COM | Seq ID No. 20 |

[a,b]The AD-associated nucleotide positions and the amino acid substitutions arising from the missense mutations at these positions.
[c,d]Wild-type (WT) and mutant (MT) oligonucleotide probes were derivatized with 5'-oligomeric PEO tails. The common (COM) probes were phosphorylated at their 5'-termini and functionalized at their 3'-ends with TET or FAM fluorescein derivatives. All the probes were designed to have the light (L) strand sequences.

OLA templates spanning the nucleotide site of interest may be prepared by PCR amplification of the COX 1 and 2 genes, for example, using the primer pairs shown in Table 4. mtDNA is highly susceptible to oxidative damage due to its proximity to the electron transport chain machinery (Ames, et al., (1993), *Proc. Natl. Acad. Sci. USA*, 90: 7915–7922) and can easily fragment during the isolation process (Higuchi, et al., (1995), *J. Biol. Chem.*, 270: 7950–7956). Therefore, PCR products are preferably about 200 to about 900 base pairs, and most preferably about 200 to about 550 base pairs in size.

The mitochondrially encoded COX 1 and 2 genes were amplified by PCR using the primer pairs shown in Table 4. Two separate amplification reactions were performed for the COX 1 gene.

(a) The primers are designated as light (L) or heavy (H) strand, based on mtDNA terminology.

(b) The AD-associated nucleotide positions (6366, 6483, 7146, 7650, 7868 and 8021) are within the PCR fragments shown alongside.

(c) The four PCR products were pooled and analyzed by the multiplex OLA, wherein the six AD-associated sites were interrogated in the same reaction.

TABLE 4

PCR PRIMERS FOR OLA ANALYSIS

| GENE | SEQ ID NO. | SEQUENCE (5'->3') | STRAND[a] | PCR LENGTH | BASE ANALYSIS[b] |
|---|---|---|---|---|---|
| COX 1 | 21 | GAGCCTCCGTAGACCTAACCATCT | L | 246 | 6366, 6483 |
| COX 1 | 22 | GGTCGAAGAAGGTGGTGTTGAG | H | | |
| COX 1 | 23 | CCATCATAGGAGGCTTCATTCACTG | L | 200 | 7146 |
| COX 1 | 24 | TGATAGGATGTTTCATGTGGTGTATGC | H | | |
| COX 2 | 25 | CATGCAGCGCAAGTAGGTCTACAAGAC | L | 502 | 7650 |
| COX 2 | 26 | AGCCTAATGTGGGGACAGCTCATG | H | | 7868, 8021 |

(d) The OLA products were resolved by electrophoresis, and the fluorescent intensities associated with the product bands were used to estimate the degree of heteroplasmy.

Figure 5:
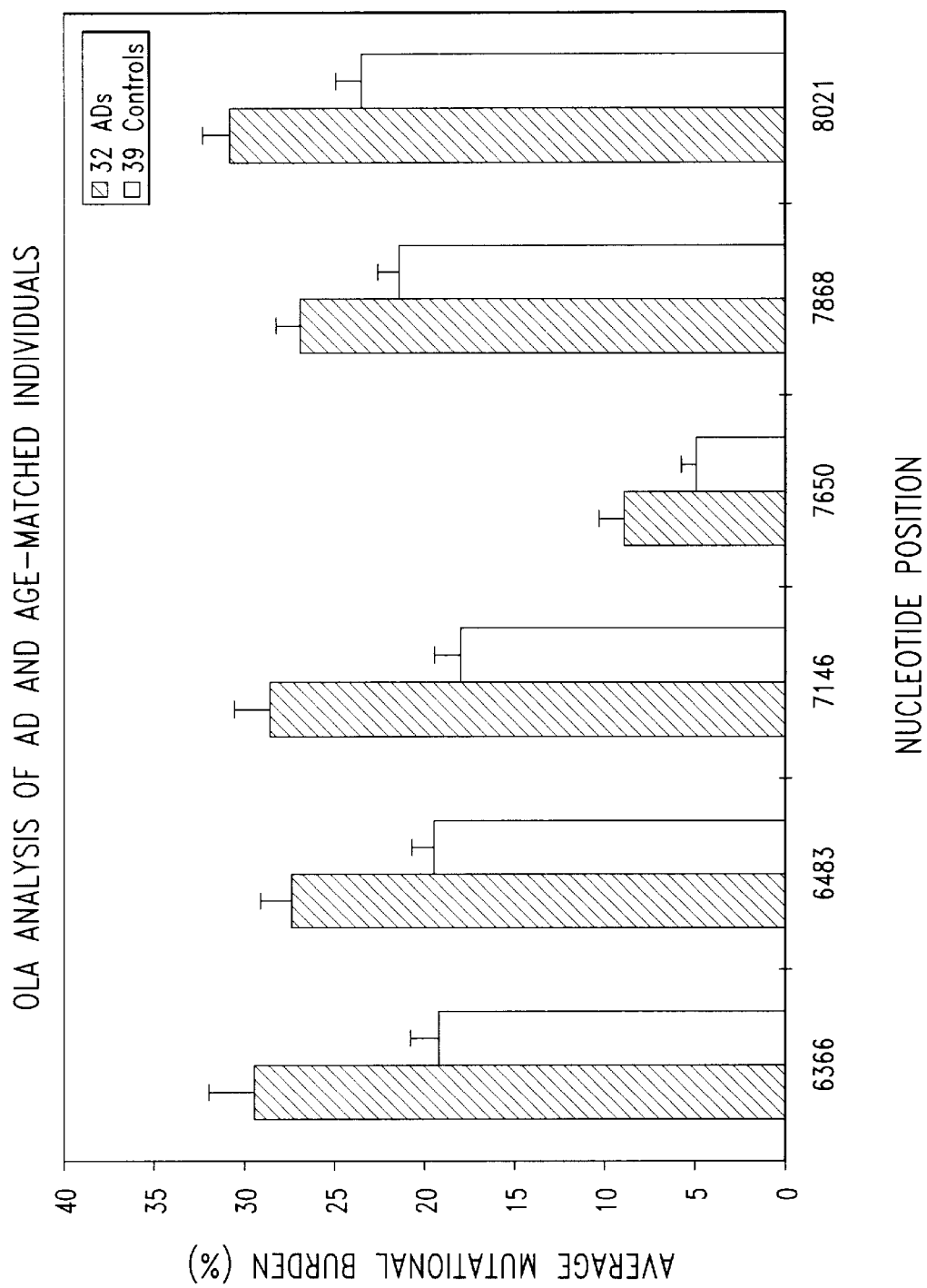
FIG. 5 is a bar graph showing the results of OLA of AD and age-matched controls for six AD-associated mtDNA loci for AD (n=32) and age-matched controls (n=39). Data is presented as mean±standard error of mean (S.E.M.).
Figure 6:
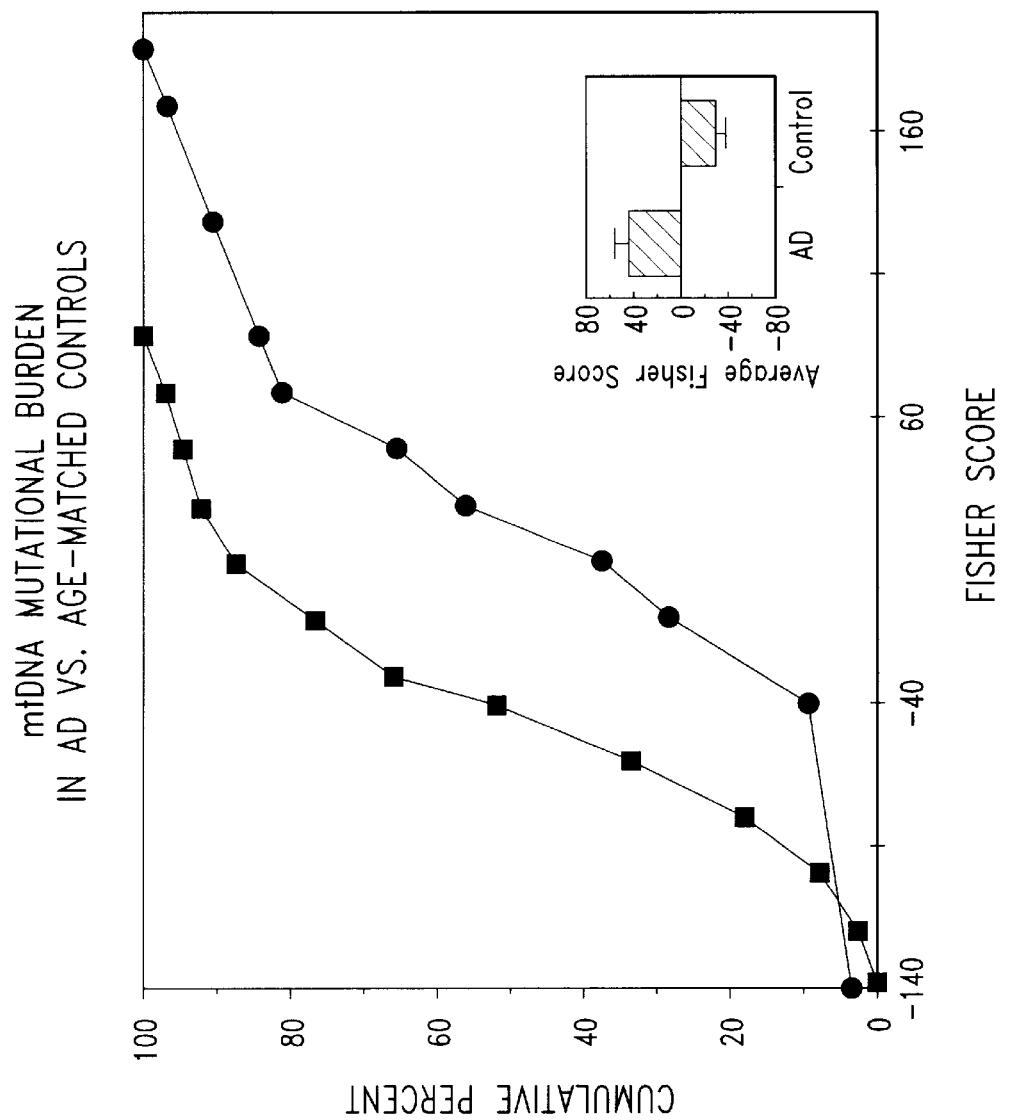
FIG. 6 is a graph of the mutational burden in AD versus age-matched controls.

Thirty-two patients with clinical diagnosis of probable/possible AD and 39 age-matched controls were examined. mtDNA was extracted from blood obtained from these individuals by isolating the platelet-rich white blood cell fraction followed by cell lysis by the boiling procedure. The percentage of mutant to normal mtDNA was determined for each of the six AD-associated loci by multiplex OLA. Analysis reveals statistically significant differences ($p<0.001$) in the mean mutational burden at the six AD-associated sites between the AD and control groups, and the mutations are elevated in a significant number of AD cases (FIG. 5). In a preferred embodiment of the present invention, the mutant allele frequency data may be, further analyzed by, for example, the Fisher multivariate discriminant analysis technique (see Johnson, R. and Wichern, D. (1988) In Applied Multivariate Statistical Analysis, Prentice Hall, pp 461–471, Englewood Cliffs, N.J., incorporated herein by reference thereto). The multivariate discriminant analysis technique separates and classifies individuals into distinct populations based on differences in mutational burden. The method yields a univariate observation (Fisher score) that represents the overall mutational burden across these six nucleotide positions. The higher the Fisher score, the greater the mutational burden, and the higher the Fisher score, the better these six mutations taken together discriminate AD from controls. Taken together, the AD cases have significantly higher Fisher scores than controls (FIG. 6 inset). To illustrate the representation of individuals within the population, Fisher scores were used to create a cumulative frequency distribution. As seen in FIG. 6, the control and AD populations are distinctly separated on the basis of the overall mutational burden at the AD-associated nucleotide sites. It is rare for AD cases to have low Fisher scores while it is common for controls to have low scores. Low Fisher scores, therefore, represent a negative risk factor for AD. In contrast, it is common for AD cases to have high Fisher scores and hence, higher mutational burdens. It is very rare for controls to have high Fisher scores. High Fisher scores, therefore, represent a strong positive risk factor for AD.

Multivariate discriminant analysis of mutant mitochondrial allele frequencies serves two purposes. First, it is used to separate two distinct populations (AD and controls) based on differences in mutational burden. Second, the technique is a tool for allocating new subjects to previously defined populations based on rules of classification established by discriminant analysis. As exemplified by the cumulative frequency distribution curves, the Fischer score threshold is an important parameter for classification. Since the sample size determines the absolute value of the Fisher score, it should be obvious to those skilled in the art that a large database is necessary for classification. Thus, OLA analysis followed by multivariate discriminant analysis can be used for confirmation of clinical diagnosis of AD.

The AD-associated mutations are present in peripheral blood, and detection of these mutations provides a sensitive and specific test for the confirmation of the clinical diagnosis of AD. These mutations are elevated in approximately 60% of clinically diagnosed AD patients, and only 10% of cognitively normal controls. The AD cases that do not have elevated levels of these mutations may represent the genetic heterogeneity of AD and cases mis-diagnosed with AD. One sub-group is senile dementia of the Lewy body variant (SDLBV). SDLBV is clinically indistinguishable from AD but is pathologically distinct and accounts for between 20–30% of cases of autopsy-confirmed AD cases. In autopsied brains of SDLBV cases, the activity of cytochrome c oxidase is normal and these patients are, therefore, unlikely to carry elevated levels of these mutations. The neuropathology of SDLBV includes senile plaque formation, Lewy bodies (proteinaceous structures) and few or sparse neurofibrillary tangles (NFT). The brains from SDLBV patients have fewer NFTs in the hippocampus, parahippocampal gyrus and frontal cortex compared to AD brains. SDLBV cases also have lower cortical acetyltransferase (ChAT) activity than AD cases. ChAT catalyses the synthesis of the neurotransmitter acetylcholine from acetyl CoA and choline, and CHAT deficiencies lead to decreases in levels of acetylcholine. SDLBV is also associated with an increase in the numbers of muscarinic receptors in the neocortex while AD is not. Therefore, SDLBV brains have decreased cholinergic function but increased capacity to respond to acetylcholine because of increased receptor numbers in the neocortex. SDLBV, and not AD patients, are most likely to respond to cholinergic therapies, e.g., treatment with the drug Cognex. The diagnostic test based on AD-associated mutations in mitochondrial cytochrome c oxidase subunit 1 and 2 genes may be useful in selecting patients for cholinergic replacement therapies by exclusion. By excluding AD patients with high mutational burden from clinical trials with cholinomimetics, the population of responders can be enriched. This would exclude AD patients not likely to respond from the trials and thus limit their exposure to possible toxic side-effects of the compounds.

Administration of the present blood-based genetic test for AD is convenient and is significantly less intrusive to the AD patient than other tests requiring, for example, cerebrospinal fluid-based analysis for AD biochemical markers.

The present invention thus provides a genetic test for Alzheimer's disease that employs a non-isotopic detection assay in an extremely accurate quantitation of heteroplasmy associated with Alzheimer's disease. The test may be automated to enable high throughput multiplexing for the simultaneous detection of multiple mutations.

The present invention also relates to the identification and quantification of silent genetic mutations in mitochondrial genes that segregate with Alzheimer's disease. The invention provides methods and probes for detecting and quantifying linked silent mutations as a diagnostic for Alzheimer's disease.

According to the present invention, several silent mutations that are linked on the COX genes segregate with Alzheimer's disease. Detection of these silent mutations is predictive of the disease.

The present invention is illustrated by, but not limited to, the following Examples.

EXAMPLES

Definitions of Abbreviations

1×SSC=150 mM sodium chloride, 15 mM sodium citrate, pH 6.5–8

SDS=sodium dodecyl sulfate

BSA=bovine serum albumin, fraction IV probe=a labeled nucleic acid, generally a single-stranded oligonucleotide, which is complementary to the DNA or RNA target, which may be immobilized on a membrane, for example. The probe may be labeled with radioisotopes (such as $^{32}P$), haptens (such as digoxigenin), biotin, enzymes (such as alkaline phosphatase or horseradish peroxidase), fluorophores (such as fluorescein or Texas Red), FAM or TET dyes, or chemilumiphores (such as acridine).

PCR=polymerase chain reaction, as described by Erlich et al., *Nature* 331: 461–462 (1988) hereby incorporated by reference.

ASO=allele-specific oligonucleotide hybridization

OLA=oligonucleotide ligation assay

Example I

Isolation and Cloning of Cytochrome c Oxidase Genes

DNA was obtained from AD patients and from nonAlzheimer's (normal) individuals. Normal individuals and AD patients were age-matched and classified as probable AD by NINCDS criteria (McKann et al., *Neurology* 34: 939–944 (1984)).

For blood samples, 6 ml samples were drawn, added to 18 ml of dextrane solution (3% dextrane, average MW=250,000 kiloDaltons (kDa), 0.9% sodium chloride, 1 mM ethylenedinitrilo tetraacetate), mixed and maintained at room temperature for 40 minutes without agitation to allow erythrocytes to sediment.

The plasma and leukocyte fraction was transferred to a centrifuge tube and leukocytes were collected by centrifugation at 14,000×g for 5 minutes. The leukocyte pellet was resuspended in 3.8 ml of water and vortexed for 10 seconds to lyse remaining erythrocytes. 1.2 ml of 0.6M sodium chloride was added and the sample was again centrifuged at 14,000×g for 5 minutes to collect the leukocytes. The leukocyte pellet was resuspended in 0.4 ml of a solution containing 0.9% sodium chloride/1 mM ethylenedinitrilo tetraacetate and stored at −80° C.

In another method of preparing white blood cells, 5–7 mL samples of blood were drawn into EDTA-coated vacutainers. The blood was transferred into Accuspin® tubes (Sigma) containing 3 ml of the tisue culture medium HISTOPAQUE® (Sigma). Blood cells were sedimented according to manufacturer's instructions by centrifugation at 1000 g for 10 minutes at room temperature using a swinging-bucket rotor. The plasma and the opaque layer, containing mononuclear cells (lymphocytes and monocytes) and platelets, were transferred to a 15 mL sterile conical centrifuge tube and centrifuged at 12,000 g for 10 minutes at 20° C. using a fixed angle rotor. The leukocyte pellet was resuspended in 0.4 mL of a solution containing 0.9% sodium chloride/1 mM ethylenedinitrilo tetraacetate and stored at −80° C.

Total cellular DNA was isolated from 0.2 ml of the frozen leukocyte sample. The frozen leukocytes were thawed, then collected by centrifugation at 14,000×g in a microcentrifuge for 5 minutes. The cell pellet was washed three times with 0.8 ml of Dulbecco's Phosphate Buffered Saline (PSB; Gibco Laboratories, Life Technologies, Inc., Grand Island, N.Y.; catalog #3104040AJ) and resuspended in 0.3 ml water. The leukocytes were lysed by incubating the samples for 10 minutes in a boiling water bath. After the samples had to come to room temperature, cellular debris was pelleted by centrifugation at 14,000×g for 5 minutes. The supernatant was transferred to a clean microcentrifuge tube. DNA concentration was determined by UV absorption at 260 nm.

The target cytochrome c oxidase gene sequences were amplified in full gene lengths and as approximately 280–350 base pair fragments by Polymerase Chain Reaction (PCR) (Erlich et al., *Nature* 331: 461–462 (1988)). Primers were designed using the published Cambridge sequence for normal human COX genes. For full gene length amplification, primers were specific for COX gene sequences located approximately 100 nucleotides upstream and downstream of the mitochondrial COX genes encoding subunits 1, 2, and 3. The sequences of the primers are shown in Table 5. For gene fragment amplification, twelve primer pairs were synthesized, and the sequences are presented in Table 5.

TABLE 5

| PCR PRIMER TARGET | PRIMER NO | STRAND | PRIMER SEQUENCE (5'->3') | SEQ ID NO. |
|---|---|---|---|---|
| FOR FULL GENE LENGTH AMPLIFICATION | | | | |
| COX 1 | #1 | L | 5'-CAATATGAAAATCACCTCGGAGC-3' | 27 |
| COX 1 | #2 | H | 5'-TTAGCCTATAATTTAACTTTGAC-3' | 28 |
| COX 2 | #1 | L | 5'-CAAGCCAACCCCATGGCCTCC-3' | 29 |
| COX 2 | #2 | H | 5'-AGTATTTAGTTGGGGCATTTCAC-3' | 30 |
| COX 3 | #1 | L | 5'-ACAATTCTAATTCTACTGACTATCC-3' | 31 |
| COX 3 | #2 | H | 5'-TTAGTAGTAAGGCTAGGAGGGTG-3' | 32 |
| FOR GENE FRAGMENT AMPLIFICATION | | | | |
| COX 1 | #3 | L | 5'-TTACAGTCCAATGCTTCACTC-3' | 33 |
| COX 1 | #4 | H | 5'-TGTTTATGCGGGGAAACGC-3' | 34 |
| COX 1 | #5 | L | 5'-AATCGGAGGCTTTGGCAACTG-3' | 35 |
| COX 1 | #6 | H | 5'-TGGTATTGGGTTATGGCAGGG-3' | 36 |
| COX 1 | #7 | L | 5'-TAGCAGGTGTCTCCTCTATCTT-3' | 37 |
| COX 1 | #8 | H | 5'-CCATACCTATGTATCCAAATGGTTC-3' | 38 |
| COX 1 | #9 | L | 5'-GGAATAATCTCCCATATTGTAACTT-3' | 39 |

TABLE 5-continued

| PCR PRIMER TARGET | PRIMER NO | STRAND | PRIMER SEQUENCE (5'->3') | SEQ ID NO. |
|---|---|---|---|---|
| COX 1 | #10 | H | 5'-GTCAGGCCACCTACGGTG-3' | 40 |
| COX 1 | #11 | L | 5'-ATGATCTGCTGCAGTGCTCT-3' | 41 |
| COX 1 | #12 | H | 5'-ATTCCGGATAGGCCGAGA-3' | 42 |
| COX 1 | #13 | L | 5'-TCGGCGTAAATCTAAGTTTCTT-3' | 43 |
| COX 1 | #14 | H | 5'-TTGGCTTGAAACCAGCTTT-3' | 44 |
| COX 2 | #3 | L | 5'-GTCAAAGTTAAATTATAGGCTAA-3' | 45 |
| COX 2 | #4 | H | 5'-TGACCTCGTCTGTTATGTAAAGG-3' | 46 |
| COX 2 | #5 | L | 5'-CGCCATCATCCTAGTCCTCA-3' | 47 |
| COX 2 | #6 | H | 5'-ATGAGTGCAAGACGTCTTGTGAT-3' | 48 |
| COX 2 | #7 | L | 5'-GAGTAGTACTCCCGATTGAAGCC-3' | 49 |
| COX 2 | #8 | H | 5'-AGTTAGCTTTACAGTGGGCTCTAG-3' | 50 |
| COX 3 | #3 | L | 5'-TTCTAGTAAGCCTCTACCTGCACG-3' | 51 |
| COX 3 | #4 | H | 5'-AATAAATAGGATTATCCCGTATCGA-3' | 52 |
| COX 3 | #5 | L | 5'-ACCACACACCACCTGTCCA-3' | 53 |
| COX 3 | #6 | H | 5'-AAGGGAGACTCGAAGTACTCTGA-3' | 54 |
| COX 3 | #7 | L | 5'-TATTACAATTTTACTGGGTCTCT-3' | 55 |
| COX 3 | #8 | H | 5'-ACTAGTTAATTGGAAGTTAACGGTA-3' | 56 |

Primers were chemically synthesized using a Cyclone Plus DNA synthesizer (Millipore Corporation, Marlborough, Mass.), a Gene Assembler DNA Syntheutilizing (Pharmacia) utilizing beta-cyanoethylphosphoramidite chemistry, or a 394 DNA/RNA Synthesizer (Applied Biosystems) using standard phosphoramidite chemistry. Newly synthesized primers were deprotected using ammonium hydroxide, lyophilized and purified by NAP-10 column chromatography (Pharmacia LKB Biotechnology Inc., Piscataway, N.J.). Tritylated oligonucleotides synthesized with the 394 DNA/RNA Synthesizer were purified by OPC Column chromatography (Perkin-Elmer). DNA concentration was determined by UV absorption at 260 nm.

Amplification was performed using 0.5–1.0 μg of template DNA in reaction volume of 50–100 ml of a solution containing 10 mM Tris-HCl, pH 8.3–9.5, 50 mM potassium chloride, 1–4 mM magnesium chloride, 200 μM each of dATP, dCTP, dGTP, and dTTP ("amplification cocktail"), 200 ng each of the appropriate COX forward and reverse primers and 5 units of AMPLITAG® Polymerase (Perkin-Elmer Corporation; catalog #N801-0060).

Amplification using the GENEAMP® PCR System 9600 (Perkin-Elmer Corporation) was allowed to proceed for one cycle at 95° C. for 10 seconds, 25 cycles at 95° C. for 1 minute, 60° C. for 1 minute, 72° C. for 1 minute, one cycle at 72° C. for 4 minutes, after which the samples were cooled to 4° C. Five separate amplification reactions were performed on each patient and each cytochrome c oxidase subunit. After the reactions were complete, the samples for each patient and subunit were combined and the amplified product was precipitated at −80° C. by the addition 1/10 volume of 5M sodium chloride or 3M sodium acetate and 2 volumes of 100% ethanol.

The PCR amplification product was pelleted by centrifugation, dried briefly, resuspended in 40 μl of TE buffer and purified by agarose gel electrophoresis (Sambrook et al., "Molecular Cloning: a Laboratory Manual," Cold Spring Harbor Laboratory, 1988). DNA was stained with ethidium bromide and visualized under long wavelength UV light. Bands of the expected lengths (approximately 1,700 bp/300–340 bp for COX 1, 900 bp/280–310 bp for COX 2 and 1,000 bp/300–350 bp for COX 3) were excised from the gel. The gel containing the DNA was minced into small pieces and placed into a microcentrifuge tube. 0.3 ml of 1M sodium chloride was added to the gel fragments and the sample was frozen at −80° C., then thawed and incubated at 40–50° C. for 15–20 minutes. Agarose was sedimented by centrifugation at 14,000×g for 5 minutes, the supernatant containing the DNA was transferred to a new vial and the DNA fragments were collected by ethanol precipitation.

The amplified DNA fragments were cloned into the plasmid PCRII (Invitrogen Corp., San Diego, Calif.) using the TA-Cloning Kit (Invitrogen Corp., San Diego, Calif.; catalog #K2000-01). Ligations were performed in a reaction volume of 11 μl containing 1–5 μl of PCR amplification product, 2 μl of plasmid (50 ng), 1 μl of 10×ligation buffer and 1 μl of T4 DNA Ligase 4 units. Ligation reactions were incubated at 10° C.–12° C. for 12–16 hours.

Vector-ligated PCR fragments were transformed into competent E. coli cells strain XL1-Blue MRF', XL2-Blue MRF' and Sure strain (Stratagene, San Diego, Calif.) using Epicurian Coli Competent Cells (catalog #'s 200230 and 200238, Stratagene, San Diego, Calif.). Transformed cells were spread onto LB-agar plates containing ampicillin (50 mg/ml), kanamycin (50 mg/ml), IPTG (isopropyl-B-D-thiogalactopyranoside, 20 mg/ml) and X-Gal (50 mg/ml). The blue/white color selection mechanism provided by the cloning vector in combination with the E.coli cells allowed for easy detection of recombinant clones, which were white.

Example II

Sequencing of Cytochrome c Oxidase (Cox) Genes

Plasmid DNA containing the COX gene inserts obtained as described in Example I was isolated using the Plasmid Quick Plasmid Purification Kit (Stratagene, San Diego, Calif.); or the Plasmid Kit and the QIAWELL® 96 Plasmid Kit (Qiagen, Chatsworth, Calif.). Plasmid DNA was purified from 5 to 50 ml bacterial cultures. For the Stratagene protocol "Procedure for Midi Columns", steps 10–12 of the kit protocol was replaced with a precipitation step using 2 volumes of 100% ethanol at −20° C., centrifugation at 6,000×g for 15 minutes, a wash step using 80% ethanol and resuspension of the DNA sample in 100 μl TE buffer. DNA concentration was determined by horizontal agarose gel electrophoresis.

Sequencing reactions using double-stranded plasmid DNA were performed using the SEQUENASE® Kit (United States Biochemical Corp., Cleveland, Ohio; the BaseStation T7 Kit (Millipore Corp.), the Vent Sequencing Kit (Millipore Corp.), the AmpliTag Cycle Sequencing Kit (Perkin Elmer Corp.); the Tag DNA Sequencing Kit (Boehringer Mannheim); and the PRISM Ready Reaction Dyes Deoxy Terminator Cycle Sequencing Kit (Perkin-Elmer). The DNA sequences were detected by fluorescence using the BaseStation Automated DNA Sequencer (Millipore Corp.) and the 373A DNA Sequencing System (Applied Biosystems). For gene walking experiments, fluorescent oligonucleotide primers were synthesized on the Cyclone Plus DNA Synthesizer (Millipore Corp.) or the GeneAssembler DNA Synthesizer (Pharmacia LKB Biotechnol-ogy, Inc.) utilizing betacyanoethylphosphora-midite chemistry. The following primer sequences were prepared from the published Cambridge sequences of the COX genes for subunits 1, 2, and 3, with fluorescein (F; FluoreDite fluorescein amidite, Millipore Corp.; or FlureoPrime fluorescein amidite, Pharmacia LKB Biotechnology, Inc.) being introduced in the last step of automated DNA synthesis: COX 1 primer 1 (5'-AGGCCTAACCCCTGTC-3') (SEQ. ID. NO. 57); COX 1 primer 2 (5'-GTCACAGCCCATG-3') (SEQ. ID. NO. 58); COX 1 primer 3 (5'-CCTGGAGCCTCCGTAG-3') (SEQ. ID. NO. 59); COX 1 primer 4 (5'-CTTCTTCGACCCCG-3') (SEQ. ID. NO. 60); COX 1 primer 5 (5'-CATATTTCACCTCCG-3') (SEQ. ID. NO. 61); COX 1 primer 6 (5'-CCTATCAATAGGAGC-3') (SEQ. ID. NO. 62); COX 1 primer 7 (5'-CATCCTATCATCTGTAGG-3') (SEQ. ID. NO. 63); COX 2 primer 1 (5'-AGGTATTAGAAAAACCA-3') (SEQ. ID. NO. 64); COX 2 primer 2 (5'-TAACTAATACTAACATCT-3') (SEQ. ID. NO. 65); COX 2 primer 3 (5'-TGCGACTCCTTGAC-3') (SEQ. ID. NO. 66); COX 3 primer 1 (5'-GCCTTAATCCAAGCC-3') (SEQ. ID. NO. 67); COX 3 primer 2 (5'-CAATGATGGCGCGATG-3') (SEQ. ID. NO. 68); COX 3 primer 3 (5'-CCGTATTACTCGCATCAGG-3') (SEQ. ID. NO. 69); COX 3 primer 4 (5'-CCGACGGCATCTACGGC-3') (SEQ. ID. NO. 70). Primers were deprotected and purified as described above. DNA concentration was determined by UV absorption at 260 nm.

For sequence analysis of COX 1, 2 and 3 fragments (280–350 bp), the following primers were used: M13 (−20) Forward (5'-GTAAAACGACGGCCA G-3') (SEQ. ID. NO. 71) and H13 Reverse (5'-CAGGAAACAGCTATGAC-3') (SEQ. ID. NO. 72).

Sequencing reactions were performed according to manufacturer's instructions except with the following modification: 1) the reactions were terminated and reduced in volume by heating the samples without capping to 94° C. for 5 minutes, after which 4 μl of stop dye (3 mg/ml dextran blue, 95%–99% formamide; as formulated by Millipore Corp.); 2) the temperature cycles performed for the AmpliTag Cycle Sequencing Kit reactions and the Vent Sequencing Kit reactions and the Tag Sequence Kit consisted of one cycle at 95° C. for 10 seconds, 30 cycles at 95° C. for 20 seconds, at 44° C. for 20 seconds and at 72° C. for 20 seconds followed by a reduction in volume by heating without capping to 94° C. for 5 minutes before adding 4 μl of stop dye.

Electrophoresis and gel analysis were performed using the BioImage and BaseStation Software provided by the manufacturer for the BaseStation Automated DNA Sequencer (Millipore Corp.), and the 373A DNA Sequencing System with the Sequence Navigator Software (Applied Biosystems). Sequencing gels were prepared according to the manufacturer's specifications. An average of ten different clones from each individual was sequenced. The resulting COX sequences were aligned and compared with published Cambridge sequences. Mutations in the derived sequence were noted and confirmed by resequencing the variant region.

Mutations in each COX gene for each individual were compiled. Tables 1 and 2 summarize the mutation data from full length clonal gene analyses for COX subunits 1 and 2. Table 6–9 summarize the mutation data of gene fragments by clonal analysis for COX subunits 1 and 2.

Example III

Detection of Cox Mutations by Hybridization Without Prior Amplification

This example illustrates taking test sample blood, blotting the DNA, and detecting mutations by oligonucleotide hybridization in a dot blot format. Two probes (mutant and wild type) were used to determine the presence of the abnormal mutations in AD-associated codons of the COX 1 and 2 genes. The Example utilizes a dot-blot format for hybridization, however, other known hybridization formats, such as Southern blots, slot blots, "reverse" dot blots, solution hybridization, solid support based sandwich hybridization, bead-based, silicon chip-based and microtiter well-based hybridization formats can also be used.

Sample Preparation Extracts and Blotting of DNA onto Membranes

Whole blood is taken from the patient. The blood is mixed with an equal volume of 0.5–1 N NaOH, and is incubated at ambient temperature for ten to twenty minutes to lyse cells, degrade proteins, and denature any DNA. The mixture is then blotted directly onto prewashed nylon membranes, in multiple aliquots. The membranes are rinsed in 10×SSC (1.5M NaCl, 0.15M Sodium Citrate, pH 7.0) for five minutes in 1×SSC. For storage, if any, membranes are air-dried and sealed. In preparation for hybridization, membranes are rinsed in 1×SSC, 1% SDS.

Alternatively, 1–10 mLs of whole blood is fractionated by standard methods such as passage through dextran or Histopaque® medium, and the white cell layer ("buffy coat") is separated. The white cells are lysed, digested, and the DNA extracted by conventional methods (organic extraction, non-organic extraction, or solid phase). The DNA is quantitated by UV absorption of fluorescent dye techniques. Standardized amounts of DNA (0.1–5 μg) are denatured in base, and blotted onto membranes. The membranes are then rinsed.

Alternative methods of preparing cellular or mitochondrial DNA, such as isolation of mitochondria by mild cellular lysis of the white cells in boiling water for about five to ten minutes and centrifugation, are preferably used (see Example I).

Hybridization and Detection

For examples of synthesis, labelling, use, and detection of oligonucleotide probes, see "Oligonucleotides and Analogues: A Practical Approach", F. Eckstein, ed., Oxford University Press (1992); and "Synthetic Chemistry of Oligonucleotides and Analogs", S. Agrawal, ed., Humana Press (1993), which are incorporated herein by reference.

For detection and quantitation of an abnormal AD-associated mutation, membranes containing duplicate samples of DNA are hybridized in parallel; one membrane is hybridized with the normal wildtype probe, the other with the mutant probe. Alternatively, the same membrane can be hybridized sequentially with both probes and the results compared.

For example, the membranes with immobilized DNA are hydrated briefly (10–60 minutes) in 1xSSC, 1% SDS, then prehybridized and blocked in 5xSSC, 1% SDS, 0.5% casein, for 10–60 minutes at hybridization temperature (35° C.–60° C.), depending on which probe is used). Fresh hybridization solution containing probe (0.1–10 nM, ideally 2–3 nM) is added to the membrane, followed by hybridization at appropriate temperature for 15–60 minutes. The membrane is washed in 1xSSC, 1% SDS, 1–3 times at 45° C.–60° C. for 5–10 minutes each (depending on probe used), then 1–2 times in 1xSSC at ambient temperature. The hybridized probe is then detected by appropriate means.

The average proportion of AD COX gene to normal gene in the same patient can be determined by the ratio of the signal of the AD probe to the normal probe. This is a semiquantitative measure of % heteroplasmy in the AD patient and can be correlated to the severity of the disease.

Example IV

Detection of Cox Mutations by Hybridization (Without Prior Amplification)

A. Slot-Blot Detection of RNA/DNA with $^{32}$P Probes

This example illustrates detection of COX mutations by slot-blot detection of DNA with $^{32}$P hybridization probes. The reagents are prepared as follows:

4xBP: 2% (w/v) Bovine serum albumin (BSA), 2% (w/v) polyvinylpyrrolidone (PVP, Mol. Wt.: 40,000) is dissolved in sterile H$_2$O and filtered through 0.22-μcellulose acetate membranes (Corning) and stored at –20° C. in 50-ml conical tubes.

DNA is denatured by adding TE to the sample for a final volume of 90 μl. 10 μl of 2N NaOH is then added and the sample vortexed, incubated at 65° C. for 30 minutes, and then put on ice. The sample is neutralized with 100 ml of 2M ammonium acetate.

A wet piece of nitrocellulose or nylon is cut to fit the slot-blot apparatus according to the manufacturer's directions, and the denatured samples are loaded. The nucleic acids are fixed to the filter by baking at 80° C. under vacuum for 1 hour or exposing to UV light (254 nm). The filter is prehybridized for 10–30 minutes in ~5 mls of 1xBP, 5xSSPE, 1% SDS at the temperature to be used for the hybridization incubation. For 15–30-base probes, the range of hybridization temperatures is between 35° C.–60° C. For shorter probes or probes with low G-C content, a lower temperature must be used. At least 2x10$^6$ cpm of detection oligonucleotide per ml of hybridization solution is added. The filter is double sealed in Scotchpak™ heat sealable pouches (Kapak Corporation) and incubated for 90 min. The filter-is washed 3 times at room temperature with 5-minute washes of 20xSSPE : 3M NaCl, 0.02M EDTA, 0.2 Sodium Phosphate, pH 7.4, 1% SDS on a platform shaker. For higher stringency, the filter can be washed once at the hybridization temperature in 1xSSPE, 1% SDS for 1 minute. Visualization is by autoradiography on Kodak XAR film at –70° C. with an intensifying screen. To estimate the amount of target, compare the amount of target detected by visual comparison with hybridization standards of known concentration.

B. Detection of RNA/DNA by Slot-Blot Analysis with Alkaline Phosphatase-oligonucleotide Conjugate Probes This example illustrates detection of COX mutations by slot-blot detection of DNA with alkaline phosphataseoligonucleotide conjugate probes, using either a color reagent or a chemiluminescent reagent. The reagents are prepared as follows:

Color reagent: For the color reagent, the following are mixed together, fresh 0.16 mg/ml 5-bromo-4-chloro-3-indolyl phosphate (BCIP), 0.17 mg/ml nitroblue tetrazolium (NBT) in 100 mM NaCl, 100 mM Tris.HCl, 5 mM MgCl$_2$ and 0.1 mM ZnCl$_2$, pH 9.5.

Chemiluminescent reagent: For the chemiluminescent reagent, the following are mixed together, 250 μM 3-adamantyl 4-methoxy 4-(2-phospho) phenyl dioxetane (AMPPD), (Tropix Inc., Bedford, Mass.) in 100 mM diethanolamine-HCl, 1 mM MgCl$_2$ pH 9.5, or preformulated dioxetane substrate lumiphos™530 (Lumigen, Inc., Southfield, Mich.).

DNA target (0.01–50 fmol) is immobilized on a nylon membrane as described above. The filter is prehybridized in hybridization solution (5xSSC, 0.5% BSA, 0.1% SDS) for 10 minutes at the hybridization temperature (37° C.–60° C.) in a sealable bag using 50–100 μl of hybridization solution per cm of membrane. The solution is removed and briefly washed in warm hybridization buffer. The conjugate probe is then added to give a final concentration of 2–5 nM in fresh hybridization solution and final volume of 50–100 μl/cm$^2$ membrane. After incubating for 30 minutes at the hybridization temperature with agitation, the membrane is transferred to a wash tray containing 1.5 mol of preheated wash-1 solution (1xSSC, 1% SDS)/cm$^2$ of membrane and agitated at the wash temperature (usually optimum hybridization temperature minus 10° C.) for 10 minutes. Wash-1 solution is removed and wash-2 solution (1xSSC) added and then agitated at the wash temperature for 10 minutes. Wash-2 solution is removed and immediate detection is done by either color or chemiluminescence.

Detection by color is done by immersing the membrane fully in color reagent, and incubating at 20° C.–37° C. until color development is adequate. When color development is adequate, the development is quenched by washing in water.

Detection by chemiluminescence is done by immersing the membrane in luminescent reagent, using 25–50 μl solution/cc$^2$ of membrane. Kodak XAR-5 film (or equivalent; emission maximum is at 477 nm) is exposed in a light-tight cassette for 1–24 hours, and the film developed.

Example V

Detection of Cox Mutations by Amplication and Hybridization

This example illustrates taking a test sample of blood, preparing DNA, amplifying a section of a specific COX gene by polymerase chain reaction (PCR), and detecting the mutation by oligonucleotide hybridization in a dot blot format.

Sample Preparation and Preparing of DNA

Whole blood is taken from the patient. The blood cells are lysed, and the DNA is prepared for PCR by using procedures described in Example I.

Amplification of Target COX genes by Polymerase Chain Reaction, and Blotting onto Membranes The treated DNA from the test sample is amplified by using procedures described in Example I. After amplification, the DNA is denatured, and blotted directly onto prewashed nylon membranes, in multiple aliquots. The membranes are rinsed in 10×SSC for five minutes to neutralize the membrane, then rinsed for five minutes in 1×SSC. For storage, if any, membranes are air-dried and sealed. In preparation for hybridization, membranes are rinsed in 1×SSC, 1% SDS.

Hybridization and Detection

Hybridization and detection of the amplified genes are accomplished as detailed in Example III.

Example VI

Sequence Analysis of Full Lenght Genes and Mutational Linkage Analysis

Figure 10A:
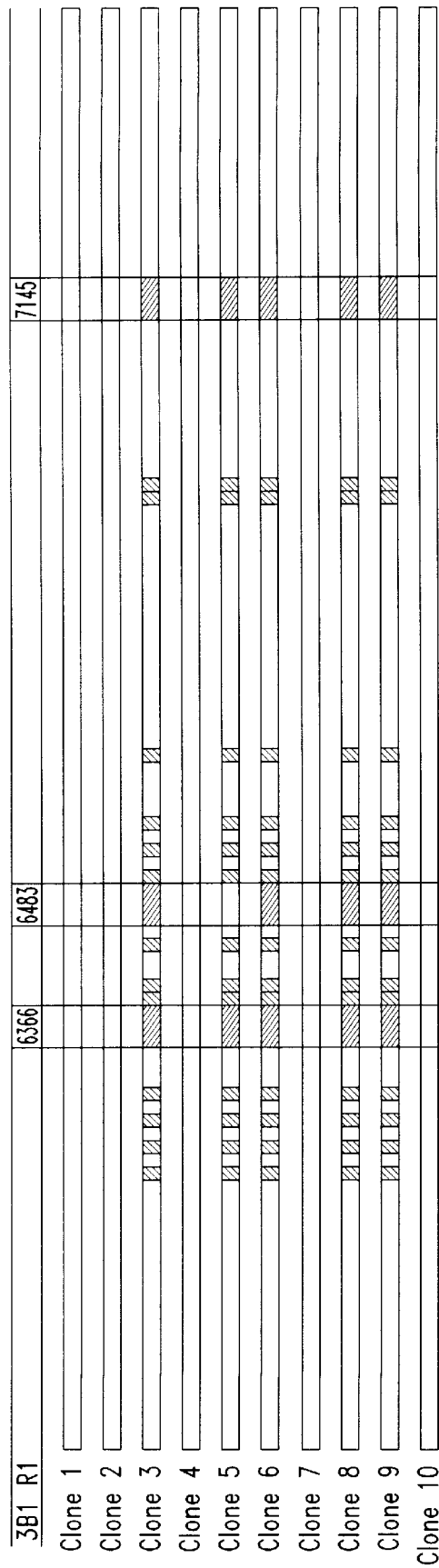
FIG. 10 is a chart showing the location of point mutations identified by the full gene length method (top) and by sequencing overlapping fragments (bottom) of the COX 1 gene.
Figure 10B:
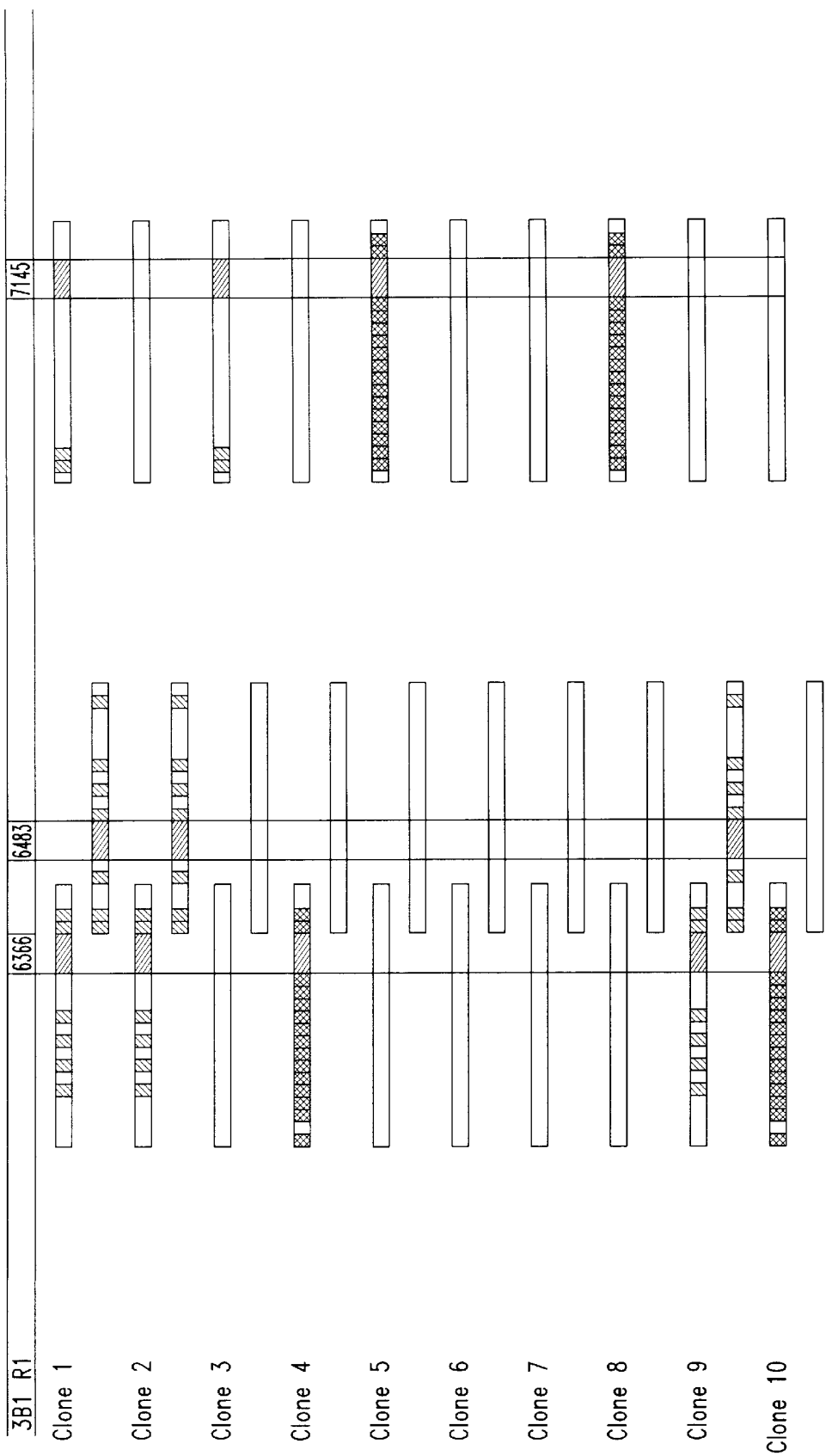

Two AD patients (3A6-KE and 3B1-RI) were selected for full gene length analysis of COX 1, 2 and 3. In both patients, two missense point mutations were identified in COX 1 at nucleotide 6366 and 7146, and fourteen silent point mutations at nucleotide 6221, 6242, 6266, 6299, 6383, 6410, 6452, 6483, 6512, 6542, 6569, 6641, 6935 and 6938 (FIG. 7). The mutations appear linked in the same DNA molecule (mtDNA genotype) in two of ten clones (Clone 7 and 10) for patient 3A6-KE and five of ten clones (Clone 3, 5, 6, 8 and 9) for 3B1-RI. All other clones show wildtype sequence with a few random mutations (not shown). Analysis of COX 2 revealed three missense point mutations at nucleotide 7650, 7868 and 8021 (FIG. 10) in both patients. These mutations appear linked in a distinct mtDNA genotype (Clone 5 for 3A6-KE, Clone 2 for 3B1-RI). The same missense mutations appear with four silent point mutations at nucleotide 7705, 7810, 7891 and 7912 (Clone 7 for 3A6-KE, Clone 3 and 4 for 3B1-RI), representing a different genotype. All other clones show wildtype sequence. COX 3 does not show any shared mutations except for a homoplasmic missense mutation at nucleotide 9599, previously described as error in the Cambridge sequence, a G→C substitution (Arg→Pro).

Evidently, mtDNA for the COX 1 and COX 2 genes exists as both the wildtype genotype and as two or more distinct mutant alleles carrying sets of point mutations. In order to investigate a possible linkage between the mutated COX 1 and COX 2 alleles, a mtDNA fragment was amplified spanning the third missense mutation at nucleotide 7145, two tRNA genes located on the mtDNA circle between COX 1 and COX 2, and two COX 2 missense mutations at nucleotide 7650 and 7868, plus four silent mutations at nucleotide 7705, 7810, 7891 and 7912. Sequence analysis of this linkage study, performed using clones for patient 2E4-KN, shows the COX 1 missense mutation at nucleotide 7146, as well as COX 2 missense mutations at nucleotide 7650 and 7868, and the four silent mutations as observed before (FIG. 9), all appearing linked in the same clone and mtDNA allele.

Example VII

Sequence Analysis of Gene Fragments

Twenty AD patients and six age-matched normal controls were selected for a sequencing study in which the three COX genes were amplified and cloned in approximately 280–350 bp fragments. Six fragments were amplified by PCR for COX 1 and three each for COX 2 and 3. The fragments span the entire coding region of each gene and provide sufficient overlap between fragments for complete sequence analysis. Ten clones for each fragment were prepared for each AD patient and control and analyzed by double-stranded DNA dye terminator cycle sequencing.

Figure 11:
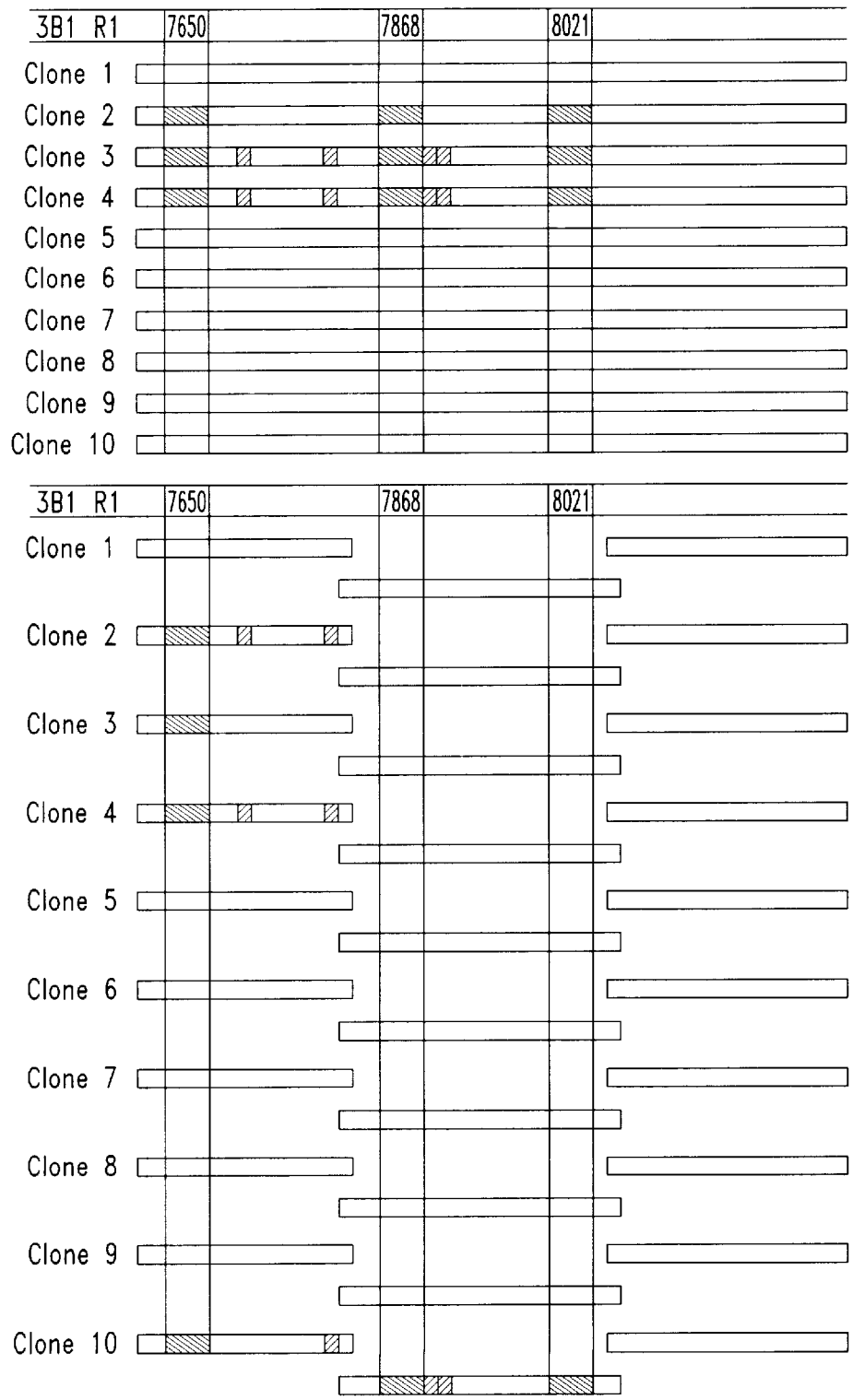
FIG. 11 is a chart showing the location of point mutations identified by the full gene length method (top) and by sequencing overlapping fragments (bottom) of the COX 2 gene.

The patient 3B1-RI, previously analyzed by the full gene length approach (Example VI) was included in this study. The sequence data show excellent agreement between both methods for COX 1 (FIG. 10) and COX 2 (FIG. 11), detecting the same missense and silent mutations in both genes. In addition, the fragment analysis procedure reveals at least one other mutated mtDNA genotype allele for COX 1 for fragment two and five (FIG. 10, clone 4 and 10, and clone 5 and 8, respectively).

Three COX 1 fragments carrying the common missense mutations were examined in great detail in the twenty AD patients and six controls. The second COX 1 fragment contains the missense mutation at nucleotide 6366, and six silent mutations as observed previously. The mutations appear, again linked in the same mtDNA alleles, in fifteen AD patients (75%) in up to three clones, and in two controls (33%) in one clone (Tables 6A and 6B). In addition, the second COX 1 fragment reveals a previously undetected, highly mutated DNA in thirteen AD patients (65%) in up to three clones, and in four controls (67%) in up to three clones. These clones possess the missense mutation at nucleotide 6366, five of the previously observed six silent mutations, and approximately twenty additional common silent point mutations (Tables 6C and 6D). This increases the number of AD patients carrying the 6366 missense mutation to nineteen (95%) and the number of controls to four (67%).

TABLE 6A

| | | | | | | | | | | UPPER HALF, LEFT SIDE | | | | | | | | |
|---|---|---|---|---|---|---|---|---|---|---|---|---|---|---|---|---|---|---|
| NUCLEOTIDE # | | | 6160 | 6182 | 6185 | 6216 | 6221 | 6224 | 6236 | 6242 | 6251 | 6260 | 6266 | 6269 | 6281 | 6299 | 6326 | 6335 | 6353 |
| AMINO ACID WT | | | Met | Ala | Phe | Leu | Pro | Pro | Leu | Leu | Ala | Glu | Gly | Ala | Trp | Phe | Ala | Asp | Phe |
| AMINO ACID MT | | | Lys | Ala | Phe | Leu | Pro | Pro | Leu | Leu | Ala | Glu | Gly | Ala | Trp | Phe | Ala | Asp | Phe |
| NUCLEOTIDE WT | | | T | G | T | T | T | C | C | C | T | G | A | A | A | A | C | C | A |
| NUCLEOTIDE MT | | | A | A | C | C | C | T | T | T | C | A | C | C | G | G | T | T | G |
| PATIENT | AG # | DIAGNOSIS | | | | | | | | | | | | | | | | | |
| 3C1_GU | 18 | AD | | | | | | | | | | | | | | | | | |
| FB331 | 331 | AD | | | | | 2 | | 2 | 2 | | | 2 | | | 2 | | | |
| 2C6_JB | 282 | AD | | | | | 2 | | 2 | 2 | | | 2 | | | 2 | | | |
| 2D5_JW | 286 | AD | | | | | | | | | | | | | | | | | |
| 2D6_JX | 287 | AD | | | | | 2 | | 2 | 2 | | | 2 | | | 2 | | | |
| 2D8_KC | 290 | AD | | | | | 1 | | 1 | 1 | | | 1 | | | 1 | | | |
| 2E4_KN | 295 | AD | | | | | 3 | | 3 | 3 | | | 3 | | | 3 | | | |
| 2E5_KG | 296 | AD | | | | | 1 | | 1 | 1 | | | 1 | | | 1 | | | |
| 2E6_KU | 297 | AD | | | | | 2 | | 2 | 2 | | | 2 | | | 2 | | | |
| 2B7_LF | 16 | AD | | | | | 2 | | 2 | 2 | | | 2 | | | 1 | | | |
| 2G8_LU | 298 | AD | | | | | | | | | | | | | | | | | |
| 2G8_LY | 302 | AD | | | | | 1 | | 1 | 1 | | | 1 | | | 1 | | | |
| 2H1_LZ | 302 | AD | | | | | 3 | | 3 | 3 | | | 3 | | | 3 | | | |
| 2K2_NX | 311 | AD | | | | | | | | | | | | | | | | | |
| 2K4_NZ | 38 | AD | | | | | 1 | | 1 | 1 | | | 1 | | | 1 | | | |
| 3B8_OB | 17 | AD | | | | | 3 | | 3 | 3 | | | 3 | | | 3 | | | |
| 3B4_PI | 13 | AD | | | | | 3 | | 3 | 3 | | | 3 | | | 3 | | | |
| 3B1_RI | 10 | AD | | | | | 3 | | 3 | 3 | | | 3 | | | 3 | | | |
| 3D1_RO | 26 | AD | | | | | 1 | | 1 | 1 | | | 1 | | | 1 | | | |
| 3B3_WO | 12 | AD | | | | | 1 | | 1 | 1 | | | 1 | | | 1 | | | |
| 3D2_GA | 27 | CONTROL | | | | | | | | | | | | | | | | | |
| 3E7_GM | 50 | CONTROL | | | | | 1 | | 1 | 1 | | | 1 | | | 1 | | | |
| 3C6_KA | 23 | CONTROL | | | | | | | | | | | | | | | | | |
| 2E3_KJ | 295 | CONTROL | | | | | | | | | | | | | | | | | |
| 2M3_PS | 314 | CONTROL | | | | | | | | | | | | | | | | | |
| 3C6_SH | 25 | CONTROL | | | | | | | | | | | | | | | | | |

TABLE 6B

| | | UPPER HALF, RIGHT SIDE | | | | | | | | | |
|---|---|---|---|---|---|---|---|---|---|---|---|
| NUCLEOTIDE # | | 6356 | 6365 | 6366 | 6378 | 6383 | 6389 | 6392 | 6398 | 6407 | 6410 |
| AMINO ACID WT | | His | Gly | Val | Leu | Gly | Ile | Asn | Ile | Ile | Ile |
| AMINO ACID MT | | His | Gly | Ile | Leu | Gly | Ile | Asn | Ile | Ile | Ile |
| NUCLEOTIDE WT | | C | T | G | T | G | C | T | C | T | C |
| NUCLEOTIDE MT | | T | C | A | C | A | T | C | T | C | T |
| PATIENT | AG # DIAGNOSIS | | | | | | | | | | |
| 3C1_GU | 18 AD | | | — | | — | | | | | — |
| FB331 | 331 AD | | | 2 | | 2 | | | | | 2 |
| 2C6_JB | 282 AD | | | — | | — | | | | | — |
| 2D5_JW | 286 AD | | | 2 | | 2 | | | | | 2 |
| 2D6_JX | 287 AD | | | — | | — | | | | | — |
| 2D8_KC | 290 AD | | | 2 | | 2 | | | | | 2 |
| 2E4_KN | 295 AD | | | 1 | | 1 | | | | | 1 |
| 2E5_KQ | 296 AD | | | 3 | | 3 | | | | | 1 |
| 2E6_KU | 297 AD | | | 1 | | 1 | | | | | 1 |
| 3B7_LF | 16 AD | | | 2 | | 2 | | | | | 2 |
| 2G6_LU | 298 AD | | | 2 | | 2 | | | | | 2 |
| 2G8_LY | 301 AD | | | — | | — | | | | | — |
| 2H1_LZ | 302 AD | | | 1 | | 1 | | | | | 1 |
| 2K2_NX | 311 AD | | | 3 | | 3 | | | | | 3 |
| 2K4_NZ | 38 AD | | | — | | — | | | | | — |
| 3B8_OB | 17 AD | | | 1 | | 1 | | | | | 1 |
| 3B4_PI | 13 AD | | | 3 | | 3 | | | | | 3 |
| 3B1_RI | 10 AD | | | 3 | | 3 | | | | | 3 |
| 3D1_RO | 26 AD | | | 3 | | 3 | | | | | 3 |
| 3B3_WO | 12 AD | | | 1 | | 1 | | | | | 1 |
| 3D2_GA | 27 CONTROL | | | 3 | | 1 | | | | | 1 |
| 3E7_GM | 50 CONTROL | | | — | | — | | | | | — |
| 3C6_KA | 23 CONTROL | | | 1 | | 1 | | | | | 1 |
| 2E3_KJ | 294 CONTROL | | | — | | — | | | | | — |
| 2M3_PS | 314 CONTROL | | | — | | — | | | | | — |
| 3C8_SH | 25 CONTROL | | | — | | — | | | | | — |

TABLE 6C

LOWER HALF, LEFT SIDE

| | | | 6160 | 6182 | 6185 | 6216 | 6221 | 6224 | 6236 | 6242 | 6251 | 6260 | 6266 | 6269 | 6281 | 6299 | 6326 | 6335 | 6353 |
|---|---|---|---|---|---|---|---|---|---|---|---|---|---|---|---|---|---|---|---|
| NUCLEOTIDE # | | | | | | | | | | | | | | | | | | | |
| AMINO ACID WT | | | Met | Ala | Phe | Leu | Pro | Pro | Leu | Leu | Ala | Glu | Gly | Ala | Trp | Phe | Ala | Asp | Phe |
| AMINO ACID MT | | | Lys | Ala | Phe | Leu | Pro | Pro | Leu | Leu | Ala | Glu | Gly | Ala | Trp | Phe | Ala | Asp | Phe |
| NUCLEOTIDE WT | | | T | G | T | T | T | C | C | C | T | G | A | A | A | A | C | C | A |
| NUCLEOTIDE MT | | | A | A | C | C | C | T | T | T | C | A | C | C | G | G | T | T | G |
| PATIENT | AG # | DIAGNOSIS | | | | | | | | | | | | | | | | | |
| 3C1_GU | 18 | AD | 3 — | — | — | — | — | — | — | — | — | — | — | — | — | — | — | — | — |
| FB331 | 331 | AD | 3 1 | 3 1 | 2 1 | 3 1 | 3 1 | 3 1 | 3 1 | 3 1 | 3 1 | 3 1 | 3 1 | 3 1 | 3 1 | — | 3 1 | 3 1 | 3 2 |
| 2C5_JB | 282 | AD | 1 — | 1 1 | — | 1 1 | 1 2 | — | — | — | — | 1 1 | 1 1 | 1 1 | 1 1 | — | 1 1 | 1 1 | 1 1 |
| 2D5_JW | 286 | AD | — | 1 2 | 2 1 | 1 2 | — | 2 | 2 | — | 2 1 | 1 1 | 1 1 | 1 1 | 1 1 | — | 1 1 | 1 1 | 1 1 |
| 2D6_JX | 287 | AD | 2 — | — | — | — | — | — | — | — | — | — | — | — | — | — | — | — | — |
| 2D8_KC | 290 | AD | — | — | — | — | — | — | — | — | 2 | 1 1 | 1 1 | 1 1 | 1 1 | — | 1 1 | 1 1 | 1 1 |
| 2E4_KN | 295 | AD | — | 1 1 | — | 1 1 | 1 1 | 1 1 | 1 | — | 1 1 | 1 1 | 1 1 | 1 1 | 1 1 | — | 1 1 | 1 1 | 1 1 |
| 2E5_KQ | 296 | AD | — | 1 1 | 1 1 | 1 1 | 1 1 | 1 1 | — | — | 1 1 | 1 1 | 1 1 | 1 1 | 1 1 | — | 1 1 | 1 1 | 1 1 |
| 2E6_KU | 297 | AD | 1 — | 1 — | — | — | — | — | — | — | 2 | 2 | 2 | 2 | 2 | — | 2 | 2 | 2 |
| 3B7_LF | 16 | AD | 1 — | 1 1 | 1 1 | — | — | — | — | — | — | — | — | — | — | — | — | — | — |
| 2G6_LU | 298 | AD | — | — | — | — | — | — | — | — | — | — | — | — | — | — | — | — | — |
| 2G8_LY | 301 | AD | — | — | — | — | — | — | — | 1 | 2 | 2 | 2 | 2 | 2 | — | 2 | 2 | 2 |
| 2H1_LZ | 302 | AD | — | — | 1 1 | 1 1 | 1 1 | 1 1 | 1 1 | 1 1 | 1 1 | 1 1 | 1 1 | 1 1 | 1 1 | — | 1 1 | 1 1 | 1 1 |
| 2K2_NX | 311 | AD | — | — | — | — | — | — | — | — | — | — | — | — | — | — | — | — | — |
| 2K4_NZ | 38 | AD | 1 — | 1 2 | 2 3 | 1 2 | 1 2 | 1 2 | 2 3 | 1 2 | 2 3 | 2 3 | 2 3 | 2 3 | 2 3 | — | 2 3 | 2 3 | 2 3 |
| 3B8_OB | 17 | AD | 2 — | 2 — | 3 1 | 2 — | 2 — | 2 | 2 | — | 2 | 2 | 2 | 2 | 2 | — | 2 | 2 | 2 |
| 3B4_PI | 13 | AD | — | — | — | — | — | — | — | — | — | — | — | — | — | — | — | — | — |
| 3B1_RI | 10 | AD | — | — | — | — | — | — | — | — | — | — | — | — | — | — | — | — | — |
| 3D1_RO | 26 | AD | — | — | — | — | — | — | — | — | 2 1 | 2 1 | 2 1 | 2 1 | 2 1 | — | 2 1 | 2 1 | 2 1 |
| 3B3_WO | 12 | AD | — | — | — | — | — | — | 2 1 | — | 2 1 | 2 1 | 2 1 | 2 1 | 2 1 | — | 2 1 | 2 1 | 2 1 |
| 3D2_GA | 27 | CONTROL | — | — | — | — | — | — | — | — | 3 | 3 | 3 | 3 | 3 | — | 3 | 3 | 3 |
| 3E7_GM | 50 | CONTROL | — | — | — | — | — | — | — | — | — | — | — | — | — | — | — | — | — |
| 3C6_KA | 23 | CONTROL | — | — | — | — | — | — | 1 | — | — | — | — | — | — | — | — | — | — |
| 2E3_KJ | 294 | CONTROL | — | — | 3 | — | — | — | — | — | — | — | — | — | — | — | — | — | 3 |
| 2M3_PS | 314 | CONTROL | — | — | — | — | — | — | — | — | — | — | — | — | — | — | — | — | — |
| 3C8_SH | 25 | CONTROL | — | — | — | — | — | — | — | — | — | — | — | — | — | — | — | — | — |

TABLE 6D

LOWER HALF, RIGHT SIDE

| NUCLEOTIDE # | 6356 | 6365 | 6366 | 6378 | 6383 | 6389 | 6392 | 6398 | 6407 | 6410 |
|---|---|---|---|---|---|---|---|---|---|---|
| AMINO ACID WT | His | Gly | Val | Leu | Gly | Ile | Asn | Ile | Ile | Ile |
| AMINO ACID MT | His | Gly | Ile | Leu | Gly | Ile | Asn | Ile | Ile | Ile |
| NUCLEOTIDE WT | C | T | G | T | G | C | T | C | T | C |
| NUCLEOTIDE MT | T | C | A | C | A | T | C | T | C | T |

| PATIENT | AG # | DIAGNOSIS | | | | | | | | | |
|---|---|---|---|---|---|---|---|---|---|---|---|
| 3C1_GU | 18 | AD | — | — | — | — | — | — | — | — | — | — |
| FB331 | 331 | AD | 3 | 3 | 3 | 3 | 3 | 3 | 2 | 3 | 3 | 3 |
| 2C5_JB | 282 | AD | 2 | 2 | 2 | 2 | 2 | 1 | 2 | 2 | 1 | 1 |
| 2D5_JW | 288 | AD | — | — | — | — | — | — | — | — | — | — |
| 2D6_JX | 287 | AD | 1 | 1 | 1 | 1 | 1 | — | 1 | 1 | — | — |
| 2D8_KC | 290 | AD | 2 | 2 | 2 | 2 | 2 | 1 | 2 | 1 | 2 | 2 |
| 2E4_KN | 295 | AD | 1 | 1 | 1 | 1 | 1 | — | 1 | 1 | — | — |
| 2E5_KO | 298 | AD | 2 | 2 | 2 | 2 | 2 | — | 2 | 2 | — | — |
| 2E6_KU | 297 | AD | — | — | — | — | — | — | — | — | — | — |
| 3B7_LF | 16 | AD | — | 1 | 1 | 1 | 1 | 1 | 1 | 1 | 1 | 1 |
| 2G6_LU | 298 | AD | 1 | 1 | 1 | 1 | 1 | 1 | 1 | 1 | 1 | 1 |
| 2G8_LV | 301 | AD | 2 | 2 | 2 | 2 | 2 | — | 2 | 2 | — | — |
| 2H1_LZ | 302 | AD | — | — | — | — | — | — | — | — | — | — |
| 2K2_NX | 311 | AD | — | — | — | — | — | — | — | — | — | — |
| 2K4_NZ | 38 | AD | 1 | 1 | 1 | 1 | 1 | 1 | 1 | 1 | 1 | 1 |
| 3B8_OB | 17 | AD | 2 | 2 | 2 | 2 | 2 | 2 | 2 | 2 | 2 | 2 |
| 3D4_PE | 13 | AD | 3 | 3 | 3 | 3 | 3 | — | 3 | 3 | — | — |
| 3B1_RI | 10 | AD | 2 | 2 | 2 | 2 | 2 | — | 2 | 2 | — | — |
| 3D1_RO | 28 | AD | — | — | — | — | — | — | — | — | — | — |
| 3B3_WO | 12 | AD | — | — | — | — | — | — | — | — | — | — |
| 3D2_GA | 27 | CONTROL | 2 | 2 | 2 | 2 | 2 | — | 2 | 1 | — | — |
| 3E7_GM | 50 | CONTROL | 1 | 1 | 1 | 1 | 1 | 1 | 1 | 1 | 1 | 1 |
| 3C8_KA | 23 | CONTROL | 2 | 2 | 2 | — | 2 | — | 1 | 1 | — | — |
| 2E3_KJ | 294 | CONTROL | — | — | — | — | — | — | — | — | — | — |
| 2M3_PS | 314 | CONTROL | 3 | 3 | 3 | 3 | 2 | — | 3 | 3 | — | — |
| 3C8_SH | 25 | CONTROL | — | — | — | — | — | — | — | — | — | — |

The third COX 1 fragment contains the silent mutation at nucleotide 6483 and seven previously observed silent mutations (Table 7), two of which are also seen in the second COX 1 fragment and represent the sequence overlap between the two fragments. The mutations appear, again linked as separate mtDNA alleles, in eleven AD patients in up to seven clones, and in the six controls in up to five clones.

TABLE 7

| NUCLEDTIDE # | 6393 | 6410 | 6452 | 6483 | 6512 | 6542 | 6569 | 6641 |
|---|---|---|---|---|---|---|---|---|
| AMINO ACID WT | Gly | Ile | Leu | Leu | Ala | Arg | Pro | Leu |
| AMINO ACID MT | Gly | Ile | Leu | Leu | Ala | Arg | Pro | Leu |
| NUCLEOTIDE WT | G | C | C | C | T | C | C | T |
| NUCLEOTIDE MT | A | T | T | T | C | T | A | C |

| PATIENT | AG # | DIAGNOSIS | | | | | | | | |
|---|---|---|---|---|---|---|---|---|---|---|
| 3C1_GU | 18 | AD | — | — | — | — | — | — | — | — |
| FB331 | 331 | AD | 3 | 3 | 3 | 3 | 3 | 3 | 3 | 3 |
| 2C5_JB | 262 | AD | 1 | 1 | 1 | 1 | 1 | 1 | 1 | 1 |
| 2D5_JW | 286 | AD | 7 | 7 | 6 | 7 | 7 | 6 | 7 | 7 |
| 2G7_JX | 287 | AD | 5 | 5 | 5 | 5 | 5 | 5 | 5 | 5 |
| 2D8_KC | 290 | AD | 4 | 4 | 4 | 4 | 4 | 4 | 4 | 3 |
| 2E4_KN | 295 | AD | 2 | 2 | 4 | 4 | 4 | 4 | 4 | 4 |
| 2E5_KQ | 296 | AD | — | — | — | — | — | — | — | — |
| 2E6_KU | 297 | AD | — | 1 | 1 | 1 | 1 | 1 | 1 | 1 |
| 3B7_LF | 16 | AD | — | — | — | — | — | — | — | — |
| 2G6_LU | 298 | AD | 2 | 2 | 4 | 5 | 5 | 3 | 5 | 4 |
| 2G8_LY | 301 | AD | 1 | 1 | — | 1 | 1 | 1 | 1 | 1 |
| 2H1_LZ | 302 | AD | — | — | — | — | — | — | — | — |
| 2K2_NX | 311 | AD | — | — | — | — | — | — | — | — |
| 2K4_NZ | 38 | AD | 1 | 1 | 1 | 1 | 1 | — | 1 | 1 |
| 3B6_OB | 17 | AD | — | — | — | — | — | — | — | — |
| 3B4_PI | 13 | AD | 1 | 1 | 1 | 1 | 1 | 1 | 1 | 1 |
| 3B1_RI | 10 | AD | — | — | — | — | — | — | — | — |
| 3D1_RO | 26 | AD | — | — | — | — | — | — | — | — |
| 3B3_WO | 12 | AD | — | — | — | — | — | — | — | — |
| 3D2_GA | 27 | CONTROL | — | — | 1 | 1 | 1 | 1 | 1 | 1 |
| 3E7_GM | 50 | CONTROL | 1 | 1 | 1 | 1 | 1 | 1 | 1 | 1 |

TABLE 7-continued

| | | | | | | | | | | |
|---|---|---|---|---|---|---|---|---|---|---|
| 3C6_KA | 23 | CONTROL | 1 | 1 | 1 | 1 | 1 | 1 | 1 | 1 |
| 2E3_KJ | 294 | CONTROL | 5 | 5 | 5 | 5 | 5 | 5 | 5 | 5 |
| 2M3_PS | 314 | CONTROL | 1 | 3 | 4 | 4 | 4 | 4 | 4 | 4 |
| 3C8_SH | 25 | CONTROL | 4 | 4 | 4 | 4 | 4 | 4 | 4 | 4 |

The fifth COX 1 fragment contains the missense mutation at nucleotide 7146 and two silent mutations as observed before (Table 8A). Clones carrying these linked mutations appear in nine AD patients (45%) and one control (17%). A new genotype was detected in clones carrying the missense mutation at nucleotide 7146 and a set of silent and missense mutations. The allele(s) appears in eleven AD patients and five controls (Table 8B), increasing the number of AD patients carrying the 7146 mutation to fifteen of twenty (75%) and the number of controls to two of six (33%).

TABLE 8A

UPPER HALF, LEFT SIDE

| NUCLEOTIDE # | 6929 | 6932 | 6935 | 6938 | 6944 | 6950 | 6956 | 6962 | 6965 | 6975 | 6990 | 7013 | 7022 | 7028 | 7037 | 7040 |
|---|---|---|---|---|---|---|---|---|---|---|---|---|---|---|---|---|
| AMINO ACID WT | Leu | Gly | Phe | Ile | Leu | Thr | Gly | Leu | Thr | Phe | Leu | Thr | Val | Ala | His | Tyr |
| AMINO ACID MUT | Leu | Gly | Phe | ILe | Leu | Thr | Gly | Leu | Thr | Leu | Phe | Thr | Val | Ala | His | Tyr |
| NUCLEOTIDE WT | A | A | C | C | T | C | T | G | T | T | C | G | T | C | C | T |
| NUCLEOTIDE MT | G | G | T | T | C | A | C | A | G | C | T | A | C | T | T | C |

| PATIENT | AG # | DIAGNOSIS | | | | | | | | | | | | | | | |
|---|---|---|---|---|---|---|---|---|---|---|---|---|---|---|---|---|
| 3C1_GU | 18 | AD | — | — | | | | | | | | | | | | | |
| FB331.D | 331 | AD | 1 | 1 | | | | | | | | | | | | | |
| 2C5_JB | 262 | AD | 1 | 1 | | | | | | | | | | | | | |
| 2D5_JW | 286 | AD | 1 | 1 | | | | | | | | | | | | | |
| 2G7_JX | 267 | AD | — | — | | | | | | | | | | | | | |
| 2D8_KC | 290 | AD | 2 | 2 | | | | | | | | | | | | | |
| 2E4_KN | 295 | AD | — | — | | | | | | | | | | | | | |
| 2E5_KG | 296 | AD | 1 | 1 | | | | | | | | | | | | | |
| 2E6_KU | 297 | AD | 1 | 1 | | | | | | | | | | | | | |
| 3B7_LF | 16 | AD | — | — | | | | | | | | | | | | | |
| 2G6_LU | 298 | AD | 2 | 2 | | | | | | | | | | | | | |
| 2H1_LZ | 301 | AD | — | — | | | | | | | | | | | | | |
| 2K2_NX | 311 | AD | — | — | | | | | | | | | | | | | |
| 2K4_NZ | 38 | AD | — | — | | | | | | | | | | | | | |
| 3B8_OB | 17 | AD | — | — | | | | | | | | | | | | | |
| 3B4_PI | 13 | AD | — | — | | | | | | | | | | | | | |
| 3B1_RI | 10 | AD | 2 | 2 | | | | | | | | | | | | | |
| 3D1_RO | 26 | AD | — | — | | | | | | | | | | | | | |
| 3B3_WO | 12 | AD | 1 | 1 | | | | | | | | | | | | | |
| 3D2_GA | 27 | CONTROL | — | — | | | | | | | | | | | | | |
| 3E7_GM | 50 | CONTROL | — | — | | | | | | | | | | | | | |
| 3C6_KA | 23 | CONTROL | — | — | | | | | | | | | | | | | |
| 2E3_KJ | 294 | CONTROL | — | — | | | | | | | | | | | | | |
| 2M3_PS | 314 | CONTROL | — | — | | | | | | | | | | | | | |
| 3C8_SH | 25 | CONTROL | 1 | 1 | | | | | | | | | | | | | |

TABLE 8B

UPPER HALF, RIGHT SIDE

| NUCLEOTIDE # | 7064 | 7072 | 7076 | 7079 | 7100 | 7112 | 7133 | 7145 | 7146 | 7160 | 7169 | 7175 |
|---|---|---|---|---|---|---|---|---|---|---|---|---|
| AMINO ACID WT | Phe | Met | Gly | Gly | Leu | Tyr | Ala | Phe | Thr | Ile | Asn | Thr |
| AMINO ACID MUT | Phe | Thr | Gly | Gly | Leu | Tyr | Ala | Phe | Ala | Ile | Asn | Thr |
| NUCLEOTIDE WT | T | T | A | C | A | C | C | C | A | C | T | T |
| NUCLEOTIDE MT | C | C | G | T | G | T | T | T | G | A | C | C |

PATIENT   AG # DIAGNOSIS

TABLE 8B-continued

UPPER HALF, RIGHT SIDE

| | | | |
|---|---|---|---|
| 3C1_GU | 18 | AD | — |
| FB331.D | 331 | AD | 1 |
| 2C5_JB | 282 | AD | 1 |
| 2D5_JW | 286 | AD | 1 |
| 2G7_JX | 287 | AD | — |
| 2D8_KC | 290 | AD | 2 |
| 2E4_KN | 295 | AD | — |
| 2E5_KG | 296 | AD | 1 |
| 2E6_KU | 297 | AD | 1 |
| 3B7_LF | 16 | AD | — |
| 2G6_LU | 298 | AD | 2 |
| 2G8_LY | 301 | AD | — |
| 2H1_LZ | 302 | AD | — |
| 2K2_NX | 311 | AD | — |
| 2K4_NZ | 38 | AD | — |
| 3B8_OB | 17 | AD | — |
| 3B4_PI | 13 | AD | — |
| 3B1_RI | 10 | AD | 2 |
| 3D1_RO | 26 | AD | — |
| 3B3_WO | 12 | AD | 2 |
| 3D2_GA | 27 | CONTROL | — |
| 3E7_GM | 50 | CONTROL | — |
| 3C6_KA | 23 | CONTROL | — |
| 2E3_KJ | 294 | CONTROL | — |
| 2M3_PS | 314 | CONTROL | — |
| 3C8_SH | 25 | CONTROL | 1 |

TABLE 8C

LOWER HALF, LEFT SIDE

| NUCLEOTIDE # | | 6929 | 6932 | 6935 | 6938 | 6944 | 6950 | 6956 | 6962 | 6965 | 6975 | 6990 | 7013 | 7022 | 7028 | 7037 | 7040 |
|---|---|---|---|---|---|---|---|---|---|---|---|---|---|---|---|---|---|
| AMINO ACID WT | | Leu | Gly | Phe | Ile | Leu | Thr | Gly | Leu | Thr | Phe | Leu | Thr | Val | Ala | His | Tyr |
| AMINO ACID MUT | | Leu | Gly | Phe | Ile | Leu | Thr | Gly | Leu | Thr | Phe | Leu | Thr | Val | Ala | His | Tyr |
| NUCLEOTIDE WT | | A | A | C | C | T | C | T | G | T | T | C | G | T | C | C | T |
| NUCLEOTIDE MT | | G | G | T | T | C | A | C | A | G | C | T | A | C | T | T | C |
| PATIENT | AG # DIAGNOSIS | | | | | | | | | | | | | | | | |
| 3C1_GU | 18 AD | — | — | — | — | — | 2 | — | 2 | 2 | 2 | 1 | 2 | — | — | — | 2 |
| FB331.D | 331 AD | — | 2 | — | 2 | 2 | 2 | — | 2 | 2 | 2 | 2 | 2 | 2 | 2 | 2 | 2 |
| 2C5_JB | 282 AD | — | — | — | — | — | 2 | — | 2 | 2 | 2 | 2 | 2 | — | — | — | 2 |
| 2D5_JW | 286 AD | — | — | — | — | — | — | — | — | — | — | — | — | — | — | — | — |
| 2G7_JX | 287 AD | — | 1 | — | 1 | 1 | 1 | — | 1 | 1 | 1 | 1 | 1 | 1 | 1 | 1 | — |
| 2D8_KC | 290 AD | — | — | — | — | — | — | — | — | — | — | — | — | — | — | — | — |
| 2E4_KN | 295 AD | 2 | — | — | 2 | 2 | 2 | 2 | 2 | — | — | — | 2 | 2 | — | — | 2 |
| 2E5_KQ | 296 AD | — | — | — | — | — | — | — | — | — | — | — | — | — | — | — | — |
| 2E6_KU | 297 AD | — | — | — | — | — | — | — | — | — | — | — | — | — | — | — | — |
| 3B7_LF | 16 AD | — | — | — | — | — | 1 | — | 1 | 1 | 1 | 1 | 1 | — | — | — | 1 |
| 2G6_LU | 298 AD | — | — | — | — | — | — | — | — | — | — | — | — | — | — | — | — |
| 2G8_LY | 301 AD | — | 2 | — | 2 | 2 | 2 | — | 2 | 2 | 2 | 2 | 2 | 2 | 2 | 2 | 2 |
| 2H1_LZ | 302 AD | 1 | — | — | 1 | 1 | 1 | 1 | — | — | — | — | 1 | 1 | — | — | 1 |
| 2K2_NX | 311 AD | — | — | — | — | — | — | — | — | — | — | — | — | — | — | — | — |
| 2K4_NZ | 38 AD | 1 | — | — | 1 | 1 | 1 | 1 | 1 | — | — | — | 1 | 1 | — | — | 1 |
| 3B8_OB | 17 AD | — | — | — | — | — | — | — | — | — | — | — | — | — | — | — | — |
| 3B4_PI | 13 AD | — | — | — | — | — | — | — | — | — | — | — | — | — | — | — | — |
| 3B1_RI | 10 AD | — | — | — | — | — | 2 | — | 2 | 2 | 2 | 2 | 2 | — | — | — | 2 |
| 3D1_RO | 26 AD | — | — | — | 1 | 1 | 1 | 1 | 1 | — | — | — | 1 | 1 | — | — | 1 |
| 3B3_WO | 12 AD | — | — | — | — | — | — | — | — | — | — | — | — | — | — | — | — |
| 3D2_GA | 27 CONTROL | — | — | — | — | — | 4 | — | 4 | 4 | 4 | 4 | 4 | — | — | — | 4 |
| 3E7_GM | 50 CONTROL | — | — | — | — | — | — | — | — | — | — | — | — | — | — | — | — |
| 3C6_KA | 23 CONTROL | — | — | — | — | — | 1 | — | 1 | 1 | 1 | 1 | 1 | — | — | — | 1 |
| 2E3_KJ | 294 CONTROL | — | 1 | — | 1 | 1 | 1 | — | 1 | 1 | 1 | 1 | 1 | 1 | 1 | 1 | 1 |
| 2M3_PS | 314 CONTROL | 1 | — | — | 1 | 1 | 1 | 1 | 1 | — | — | — | 1 | 1 | — | — | 1 |
| 3C8_SH | 25 CONTROL | — | 1 | — | 1 | 1 | 1 | — | 1 | 1 | 1 | 1 | 1 | 1 | 1 | 1 | 1 |

TABLE 8D

LOWER HALF, RIGHT SIDE

| NUCLEOTIDE # | 7064 | 7072 | 7076 | 7079 | 7100 | 7112 | 7133 | 7145 | 7146 | 7160 | 7169 | 7175 | |
| --- | --- | --- | --- | --- | --- | --- | --- | --- | --- | --- | --- | --- | --- |
| AMINO ACID WT | Phe | Met | Gly | Gly | Leu | Tyr | Ala | Phe | Thr | Ile | Asn | Thr | |
| AMINO ACID MUT | Phe | Thr | Gly | Gly | Leu | Tyr | Ala | Phe | Ala | Ile | Asn | Thr | |
| NUCLEOTIDE WT | T | T | A | C | A | C | C | C | A | C | T | T | |
| NUCLEOTIDE MT | C | C | G | T | G | T | T | T | G | A | C | C | |

| PATIENT | AG # | DIAGNOSIS | | | | | | | | | | | | | |
| --- | --- | --- | --- | --- | --- | --- | --- | --- | --- | --- | --- | --- | --- | --- |
| 3C1_GU | 18 | AD | 2 | — | 2 | — | — | — | — | 2 | 2 | 2 | — | 2 | ** |
| FB331.D | 331 | AD | 2 | 2 | — | 2 | 2 | 2 | — | 2 | 2 | 2 | 2 | 2 | |
| 2C5_JB | 282 | AD | 2 | — | 2 | — | — | — | — | 2 | 2 | 2 | — | 2 | ** |
| 2D5_JW | 286 | AD | — | — | — | — | — | — | — | — | — | — | — | — | |
| 2G7_JX | 287 | AD | 1 | 1 | — | 1 | 1 | 1 | — | 1 | 1 | 1 | 1 | 1 | |
| 2D8_KC | 290 | AD | — | — | — | — | — | — | — | — | — | — | — | — | |
| 2E4_KN | 295 | AD | 2 | — | 2 | — | — | — | 2 | 2 | 2 | — | 2 | — | |
| 2E5_KQ | 296 | AD | — | — | — | — | — | — | — | — | — | — | — | — | |
| 2E6_KU | 297 | AD | — | — | — | — | — | — | — | — | — | — | — | — | |
| 3B7_LF | 16 | AD | 1 | — | 1 | — | — | — | — | 1 | 1 | 1 | — | 1 | ** |
| 2G6_LU | 298 | AD | — | — | — | — | — | — | — | — | — | — | — | — | |
| 2G8_LY | 301 | AD | 2 | 2 | — | 2 | 2 | 2 | — | 2 | 2 | 2 | 2 | 2 | |
| 2H1_LZ | 302 | AD | 1 | — | 1 | — | — | — | 1 | — | 1 | — | 1 | — | |
| 2K2_NX | 311 | AD | — | — | — | — | — | — | — | — | — | — | — | — | |
| 2K4_NZ | 38 | AD | 1 | — | 1 | — | — | — | 1 | — | 1 | — | 1 | — | |
| 3B8_OB | 17 | AD | — | — | — | — | — | — | — | — | — | — | — | — | |
| 3B4_PI | 13 | AD | — | — | — | — | — | — | — | — | — | — | — | — | |
| 3B1_RI | 10 | AD | 2 | — | 2 | — | — | — | — | 2 | 2 | 2 | — | 2 | ** |
| 3D1_RO | 26 | AD | 1 | — | 1 | — | — | — | 1 | 1 | 1 | — | 1 | — | |
| 3B3_WO | 12 | AD | — | — | — | — | — | — | — | — | — | — | — | — | |
| 3D2_GA | 27 | CONTROL | 4 | — | 4 | — | — | — | — | 4 | 4 | 4 | — | 4 | ** |
| 3E7_GM | 50 | CONTROL | — | — | — | — | — | — | — | — | — | — | — | — | |
| 3C6_KA | 23 | CONTROL | 1 | — | 1 | — | — | — | — | 1 | 1 | 1 | — | 1 | ** |
| 2E3_KJ | 294 | CONTROL | 1 | 1 | — | 1 | 1 | 1 | — | — | 1 | 1 | 1 | 1 | |
| 2M3_PS | 314 | CONTROL | 1 | — | 1 | — | — | — | 1 | — | 1 | — | 1 | — | |
| 3C8_SH | 25 | CONTROL | 1 | 1 | — | 1 | 1 | 1 | — | 1 | 1 | 1 | 1 | 1 | |

Sequence analysis of the first COX 2 fragment confirmed the presence of the missense mutations at nucleotide 7650, and two silent mutations at nucleotide 7705 and 7810, again linked in the same mtDNA allele. The second COX 2 fragment revealed the two missense mutations at nucleotide 7868 and 8021, and two silent mutations at nucleotide 7891 and 7912 (Table 9). A few clones possessing additional common silent mutations, possibly representing a separate allele, were detected. No highly mutated DNA was found for COX 2.

The fragment sequence analysis for COX 3 revealed wildtype sequence only in AD patients and controls except for nucleotide 9559 (see above).

TABLE 9

| NUCLEOTIDE # | 7650 | 7663 | 7705 | 7757 | 7810 | 7861 | 7868 | 7891 | 7900 | 7912 | 7927 | 8011 | 8021 | 8038 |
| --- | --- | --- | --- | --- | --- | --- | --- | --- | --- | --- | --- | --- | --- | --- |
| AMINO ACID WT | Thr | His | Tyr | Ala | Leu | Asp | Leu | His | Tyr | Glu | Gly | Val | Ile | Arg |
| AMINO ACID MT | Ile | His | Tyr | Thr | Leu | Asp | Phe | His | Tyr | Glu | Gly | Val | Val | Arg |
| NUCLEOTIDE WT | C | C | C | G | C | T | C | C | C | G | C | A | A | T |
| NUCLEOTIDE MT | T | T | C | A | T | C | T | T | T | A | T | G | G | C |

| PATIENT | AG # | DIAGNOSIS | | | | | | | | | | | | | |
| --- | --- | --- | --- | --- | --- | --- | --- | --- | --- | --- | --- | --- | --- | --- |
| 3C1_GU | 18 | AD | — | — | — | — | — | — | — | — | — | — | — | — | — |
| FB331.D | 331 | AD | 3 | — | 2 | — | 2 | — | 1 | 1 | — | 1 | — | — | 1 | — |
| 2C5_JB | 282 | AD | 2 | — | 1 | — | — | 1 | 1 | 1 | 1 | 1 | 1 | 1 | 1 | 1 |
| 2D5_JW | 286 | AD | 2 | 1 | 2 | — | 2 | — | 1 | 1 | — | 1 | — | — | 1 | — |
| 2D6_JX | 287 | AD | 2 | — | 2 | — | 2 | — | 1 | 1 | — | 1 | — | — | 1 | — |
| 2D8_KC | 290 | AD | 2 | — | 2 | — | 2 | 1 | 5 | 5 | 1 | 5 | 1 | 1 | 5 | — |
| 2E4_KN | 295 | AD | 3 | — | 3 | — | 3 | — | 3 | 3 | — | 3 | — | — | 3 | — |
| 2E5_KQ | 296 | AD | 1 | — | 1 | — | — | 1 | 2 | 2 | — | 2 | — | — | 2 | — |
| 2E6_KU | 297 | AD | 2 | — | 2 | 2 | 2 | — | 4 | 4 | — | 3 | — | — | 4 | — |
| 3B7_LF | 16 | AD | 1 | — | 1 | — | 1 | — | 1 | 1 | — | 1 | — | — | 1 | — |
| 2G6_LU | 298 | AD | 1 | 1 | 1 | — | 1 | — | 2 | 2 | — | 2 | — | — | 2 | — |
| 2G8_LY | 301 | AD | 3 | — | 3 | — | 3 | — | 2 | 2 | — | 2 | — | — | 2 | — |
| 2H1_LZ | 302 | AD | 1 | — | — | — | 1 | — | 2 | 2 | — | 2 | — | — | 2 | — |
| 2K2_NX | 311 | AD | 2 | — | 2 | — | 2 | 1 | 1 | 1 | 1 | 1 | 1 | 1 | 1 | 1 |
| 2K4_NZ | 38 | AD | — | — | — | — | — | — | — | — | — | — | — | — | — | — |
| 3B8_OB | 17 | AD | 2 | — | 2 | 2 | 2 | — | — | — | — | — | — | — | — | — |
| 3B4_PI | 13 | AD | 1 | — | 1 | — | 1 | — | — | — | — | — | — | — | — | — |
| 3B1_RI | 10 | AD | 4 | — | 3 | — | 4 | — | 1 | 1 | — | 1 | — | — | 1 | — |

TABLE 9-continued

| | | | | | | | | | | | | | | | | | |
|---|---|---|---|---|---|---|---|---|---|---|---|---|---|---|---|---|---|
| 3D1_RO | 26 | AD | — | — | — | — | — | — | — | — | — | — | — | — | — | — |
| 3B3_WO | 12 | AD | 2 | — | 1 | — | 1 | — | — | — | — | — | — | — | — | — |
| 3D2_GA | 27 | CONTROL | 3 | — | 2 | — | 3 | — | 1 | 1 | — | 1 | — | — | 1 | — |
| 3E7_GM | 50 | CONTROL | — | — | — | — | — | — | 1 | 1 | — | 1 | — | — | 1 | — |
| 3C6_KA | 23 | CONTROL | 3 | — | 3 | — | 3 | — | 1 | 1 | — | 2 | — | — | 2 | — |
| 2E3_KJ | 294 | CONTROL | 2 | — | 2 | — | 2 | 1 | 1 | 1 | 1 | 1 | 1 | 1 | 1 | 1 |
| 2M3_PS | 314 | CONTROL | 2 | — | 2 | — | 2 | — | 1 | 1 | — | 1 | — | — | 1 | — |
| 3C8_SH | 25 | CONTROL | 1 | — | 1 | — | 1 | — | 1 | 1 | — | 1 | — | — | 1 | — |

Example VIII

Detection of Cox Mutations by Amplification and Oligonucleotide Ligation Assay

While clonal sequencing analysis is informative, the technique is not practical for accurate quantitation of mitochondrial mutational burden in population studies since it requires analyzing a large number of clones. To overcome this difficulty, an oligonucleotide ligation assay (OLA) was utilized to specifically quantify the relative abundance of mitochondrial point mutations. OLA is illustrated in FIGS. 4A and 4B.

This example illustrates taking a test sample of blood, preparing DNA therefrom, amplifying a section of the COX 1 and COX 2 genes by PCR and simultaneously detecting mutations at up to six sites by oligonucleotide ligation assay. The AD-associated nucleotide sites monitored by the assay are at MtDNA positions 6366, 6483, 7146, 7650, 7868 and 8021.

Sample Preparation and Preparation of DNA

Whole blood is taken from a patient, and the platelet-rich white blood cell fraction is prepared by the Accuspin®/Histopaque® procedure. The cells are lysed by boiling as described in Example 1 to prepare the DNA for amplification by PCR.

Oligonucleotide Synthesis

Oligonucleotides having 5' oligomeric pentaethyleneoxide (PEO) tails were synthesized on an Applied Biosystems 394 DNA/RNA synthesizer (Perkin Elmer) using standard phosphoramidite chemistry. Following cleavage from resin and deprotection with ammonium hydroxide, the $(PEO)_n$-oligonucleotides were purified by reverse phase HPLC using an acetonitrile gradient in 0.1M triethylammonium acetate, pH 7.0 running buffer. The samples were then desalted on a Pharmacia PD-10 column. Oligonucleotides having 3'-FAM or TET dyes (Perkin Elmer) and 5'-phosphates were synthesized by the method of Grossman, et al.

PCR

PCR amplification of cellular DNA was carried out in a total volume of 50 µL using COX 1 and COX 2 specific primer pairs (Table 3). The three PCR fragments, ranging in size from 200 to 502 base pairs, span the six AD-associated nucleotide positions which were monitored by OLA, below. Typically, PCR reactions contained about 1 µg of cellular DNA, 2.5 U of AmpliTaq® DNA polymerase (Perkin Elmer), 20 pMol each of the light strand primer and the heavy strand primer and 10 nMol of each DNTP in PCR buffer (10 mM Tris-HCl, pH 8.3, 50 mM KCl, 2 mM $MgCl_2$). After initial denaturation at 95° C. for 10 seconds in a Gene Amp PCR System 9600 thermal cycler (Perkin Elmer), the samples were amplified for 30 cycles under the following conditions: 95° C. for 1 minute, 60° C. for 1 minute, 72° C. for 1 minute and final extension at 72° C. for 4 minutes. After amplification, the PCR products were analyzed by electrophoresis on a 0.8% agarose gel. Aliquots of the PCR were used directly in the OLA reactions described below.

Preliminary Experiment to Determine The Sensitivity of OLA

Figure 12:
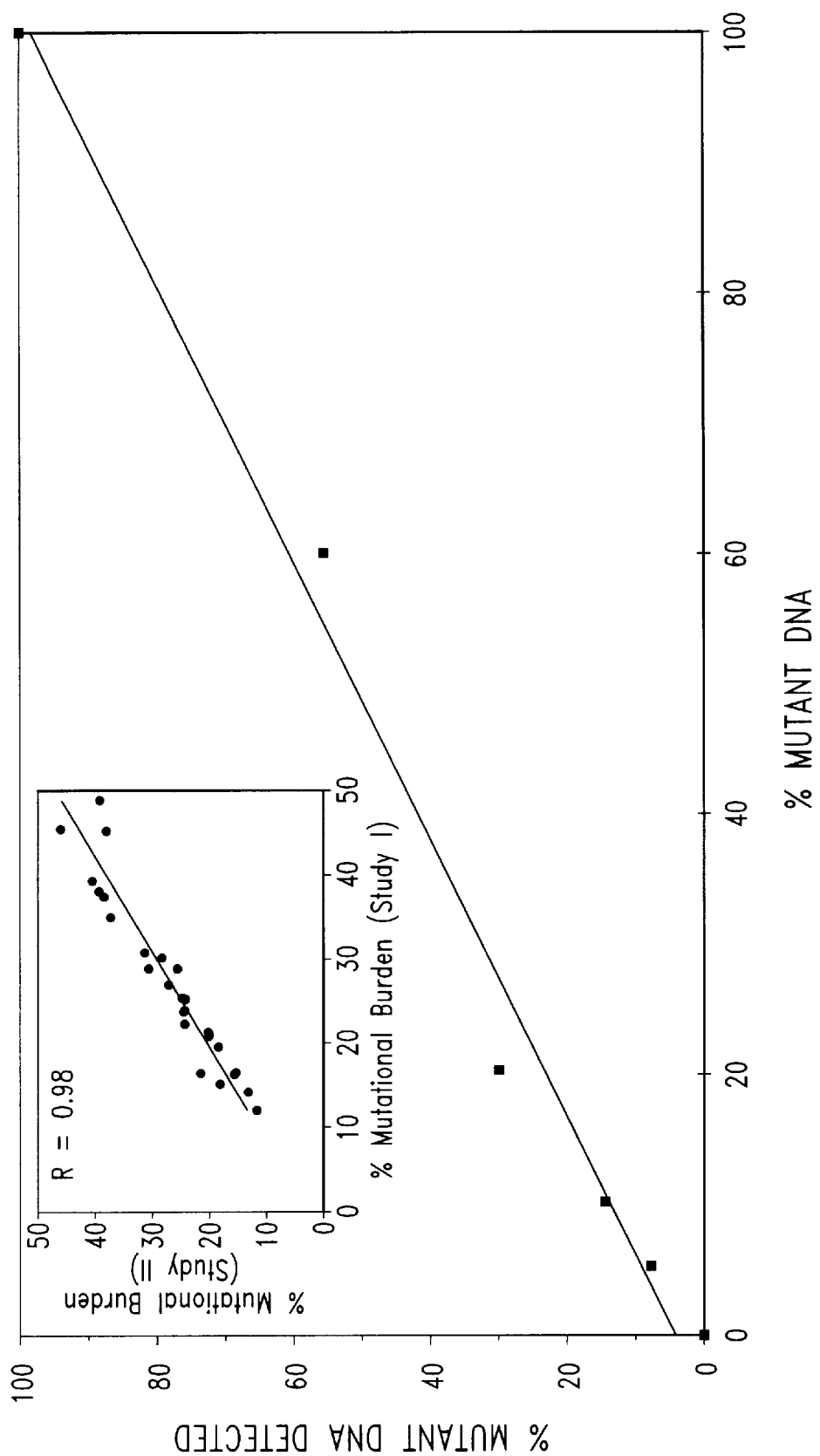
FIG. 12 is a standard curve obtained with OLA, which depicts the quantitative detection of the 7146 mutant mtDNA allele.

Plasmids containing wild-type and mutant COX 1 and COX 2 gene inserts were mixed in various ratios (0%, 5%, 10%, 20%, 60% and 100%). One fMol ($10^{-15}$ mole) amounts of these mixtures were amplified by PCR, as described above. Aliquots of the PCR products were analyzed by the OLA assay. FIG. 12 exemplifies the standard curves obtained with OLA and depicts the quantitative detection of the 7146 mutant mtDNA allele.

As can be seen in FIG. 12, there was a linear relationship (coefficient of correlation [R]=0.99) between the percentage of mutant DNA in the assay and the amount that was detected by OLA. These results indicate that OLA can easily detect 5% allele frequencies in a heteroplasmic DNA mixture. Similar results were obtained for the other five AD-associated nucleotide sites.

The ligase used in these experiments was remarkably accurate. No trace of mutant ligation product was detected when wild-type DNA was used as template, and the same result was observed in the converse case. In addition, the assay was highly reproducible as demonstrated by the close agreement of two independent OLA analyses of a heteroplasmic 6483 mtDNA mixture (FIG. 12, inset).

Multiplex OLA

OLA reactions for the six AD-associated mutations were multiplexed and the ligated products were electrophoretically distinguished by size and spectral characteristics of the fluorophor labels. Table 3 shows the oligonucleotide probe combinations used for the analysis of PCR-generated gene fragments of the COX 1 and COX 2 genes (see Table 4). Each nucleotide position was interrogated with a combination of three oligonucleotide probes: two oligonucleotides having 51'-PEO tails of differing length immediately upstream of the monitored site, and a common, downstream 5'-phosphorylated and 3'-fluorophor labelled reporter probe. The reactions were performed in 20 µL volumes containing 96 mM KCl, 34.3 mM Tris-HCl, pH 7.2, 10.9 mM $MgCl_2$, 1 mM $NAD^+$, 1.67 nM of each oligonucleotide probe, PCR reaction aliquots (1.5–4 µL) and 20 U of thermostable *Thermus aquaticus* DNA ligase. The OLA was optimized for PCR aliquot volumes to obtain comparable fluorescence signals for the six sets of ligation reactions, since PCR provides different amounts of total product for the three amplification reactions and OLA efficiencies are different for the six loci. The assay was performed with the following volumes of PCR product: 4 µL of 246 base pair fragment, 3 µL of the 200 base pair fragment and 1.5 µL of the 502 base pair fragment. The reaction conditions comprised 20 cycles of 95° C. for 30 seconds and 45° C. for 5 minutes followed by one cycle at 99° C. for 10 minutes and indefinite hold at 4° C. when the cycles were completed.

Two µL of the above described OLA reaction samples were combined with 3 µL of loading dye (0.5% blue dextran in 83% formamide/8.3 mM EDTA, pH 8.0) and 0.5 μL of TAMRA standards mix (Perkin Elmer). The samples were then separated by electrophoresis on an ABI 373 Sequencer using an 8% denaturing polyacrylamide gel and Tris borate/EDTA as running buffer. Quantitative heteroplasmy analysis was carried out by estimating the fluorescence band intensities associated with the wild-type and mutant DNA-derived ligated products using GENESCAN™ 672 software (Perkin Elmer).

FIG. 5 shows the average mutational burden at each AD-associated nucleotide locus for the two cohorts. Analysis of mutant allele frequencies revealed statistically significant differences between AD patients (n=32) and the age-matched control group (n=39) for nucleotide sites 6366, 6483, 7146, 7868 and 8021 ($p \leq 0.002$). The data are presented as mean±standard error of mean (S.E.M.). A significant difference in mutant allele frequencies between the two groups was also noted for nucleotide site 7650 ($p \leq 0.01$). However, the average mutational burden at this locus was about 50% lower than the other sites. As discussed above, sequencing studies reveal that the six mutations are linked in the same mitochondrial genome. OLA analysis shows the same pattern in FIG. 12 for five of the six interrogated nucleotide sites. The difference seen with nucleotide 7650 is probably due to less efficient ligation at the site, which can be rectified by optimization of the OLA reaction conditions or probe redesign.

Fisher Multivariant Discriminant Analysis

The mutant allele frequency data for AD patients (n=32) and age-matched controls (n=39) were further analyzed by the Fisher multivariant discriminant analysis technique (Johnson, et al. In Applied Multivariant Statistical Analysis, Prentice Hall, pp 461–471, Englewood Cliffs, N.J.). The cumulative percent of cases for each group was calculated over 20 unit intervals for the Fisher score range. Cumulative percent values are plotted in FIG. 6 as a function of the midpoint of each Fisher score interval. (Age-matched controls (closed squares); AD patients (closed circles)). As seen in FIG. 6 (inset), the average Fisher score for the two groups are quite distinct. The separation between the two groups is clearly seen in the cumulative percent versus Fisher score curve in FIG. 6. Cumulative percent refers to the percent of total study population in each group whose Fisher scores are equal to or below a particular value. The AD patients as a group are characterized by high Fisher scores while controls are distinguished by their low Fisher scores. Thus, 27 out of 32 AD patients (84%) have a Fisher score above 10, while only 5 out of 39 age-matched controls (13%) have scores higher than this value. The percentage of individual having elevated Fisher scores decreases as the threshold value increases. For example, 18 out of 32 AD patients (56%) are above a Fisher score of 30. In contrast, only 3 out of 39 controls (8%) have a score higher than 30. Finally, all controls have Fisher scores below 100, while 5 out of 32 AD patients were found to have higher scores. High Fisher scores, therefore, represent a strong positive risk factor for AD. Finally, it is rare for AD cases to have low Fisher scores. Approximately 52% of controls have Fisher scores below 20, while only 9% of AD cases have Fisher scores below this value. Low Fisher scores, and hence low mutational burdens, therefore, represent a negative risk factor for AD.

Example IX

Detection of Cox Mutations by Amplification and Multiplexed Primer Extention

Figure 13:
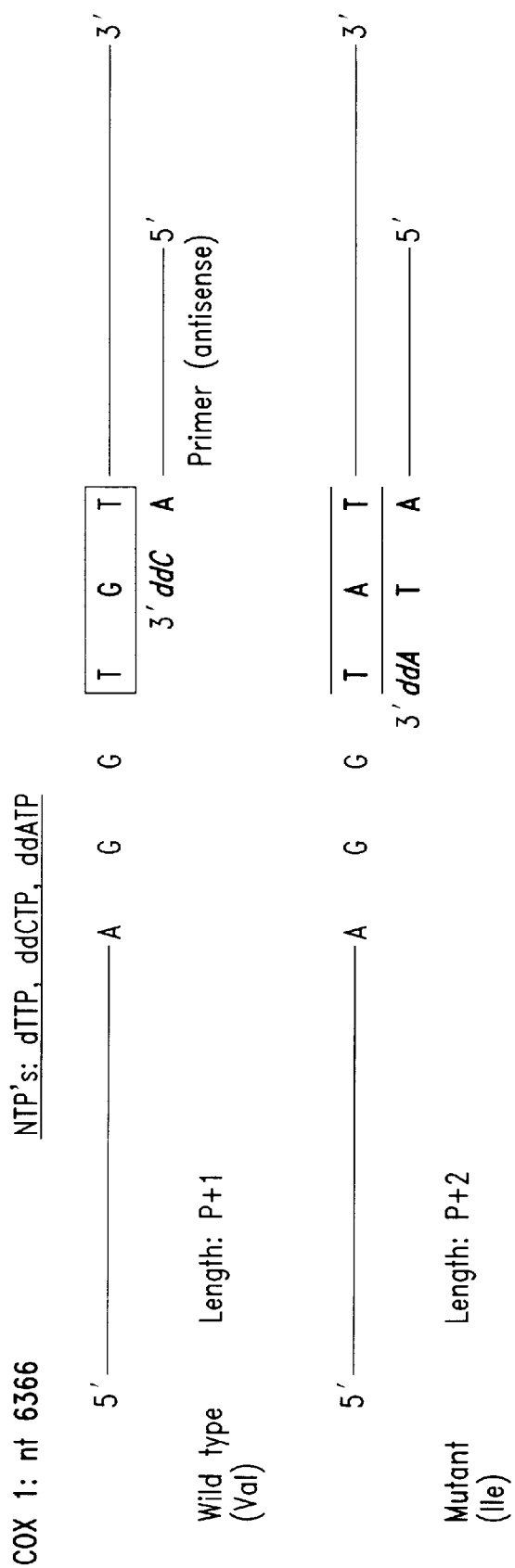
FIG. 13 is a cartoon illustration of a mutiplexed primer extension assay for interrogating the G→A point mutation at nucleotide 6366 in the mitochondrial COX 1 gene.

In addition to the results described above, quantitation of heteroplasmic mutations in the COX genes may be carried out using a multiplexed primer extension method. Simultaneous detection of mutant and wild-type DNA is accomplished using a thermostable DNA polymerase with a fluorophor-labeled primer and a selected mixture of deoxynucleotides (dNTPs) and dideoxynucleotides (ddNTPs). FIG. 13 illustrates the approach taken for interrogating the G→A point mutation at nucleotide 6366 in the mitochondrial COX 1 gene, one of several allelic variations associated with late onset Alzheimer's disease. The mutant and wild-type DNA compete as templates in the primer extension reaction, and are distinguished by differential extension of the primer. Thus, with a nucleotide combination of dTTP, ddATP, and ddCTP, the extended primer is one nucleotide longer when the template is the mutant rather than the wild-type DNA. Typically, the reactions are performed with multiple thermal cycles to ensure quantitative conversion of primers to extension products. The degree of heteroplasmy at the monitored site is estimated by comparing the ratio of fluoresence intensities of the gel-separated extension products with a standard curve generated from known wild-type/mutant template mixtures.

A high fidelity polymerase is used in order to ensure accuracy of the resulting extension products. ULTma™ DNA polymerase and THERMO SEQUENASE®, high fidelity enzymes which have 3'–5' proofreading activity are particularly suitable for the assay.

A key advantage to this diagnostic approach is that both the wild-type and mutant DNA are probed in the same reaction. This minimizes the possibility of tube-to-tube variability inherent in methods that detect mutant and wild-type DNA in separate reactions. Such methods include solid-phase minisequencing which relies on single nucleotide primer extension and traditional hybridization techniques. Misincorporation of nucleotides during primer extension is a potential drawback that can compromise quantitative mutation analysis. This problem is often encountered in single nucleotide primer extension assays that use thermostable polymerases lacking proofreading activity. Another contributing factor is the poor selectivity exhibited by certain polymerases exemplified by Taq™ polymerase for modified deoxy- or dideoxynucleotides in assays that use fluorophor labeled nucleotides as substrates. In the assay described above, the choice of high fidelity polymerase and a competitive reaction format significantly reduces erroneous nucleotide incorporation.

Templates for the primer extension reaction are generated by PCR amplification of cellular DNA. A two-step protocol is utilized for template purification since residual PCR nucleotides transferred into the primer extension reaction compromise the accuracy of the assay. Purification entails alkaline phosphatase treatment of the PCR product mixture followed through QIAquicke® columns (Qiagen, Chatsworth, Calif.). Several thermostable polymerases have been studied in PCR amplification of heteroplasmic target DNA and were found to provide product mixtures of very similar compositions. These enzymes include AmpliTaq™ DNA polymerase, ULTma™ DNA polymerase, and Tth™ DNA polymerase.

Figure 14:
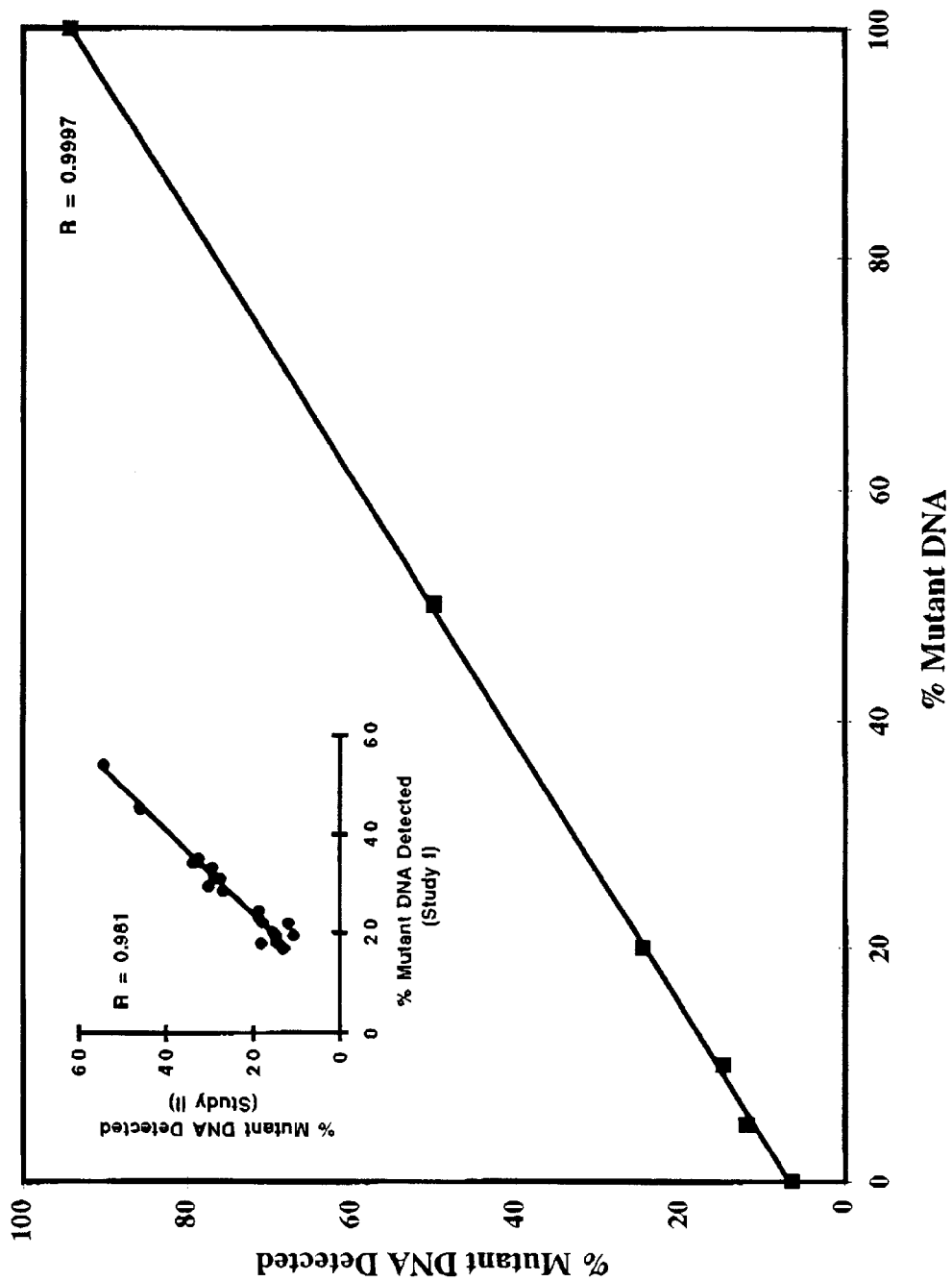
FIG. 14 is a representative standard curve derived from ULTma™ DNA polymerase-catalyzed primer extension assays.

FIG. 14 shows a representative standard curve derived from ULTma™ DNA polymerase-catalysed primer extension assays. These assays used templates containing known mixtures of wild-type and mutant DNA. There is a direct linear relationship between percent of mutant DNA in the assay and the amount that is detected. The assay reliably detects mutant alleles present at relative ratios between 1–3%. The variability in the assay is typically 5% or less. The reproducibility is illustrated by the high positive correlation between two independent assays of heteroplasmic mtDNA samples (FIG. 14 inset).

Primer extension assays are easy to design and readily configured for detecting mutations at multiple sites. This may be accomplished by using primers of different sizes and multiple fluorphor labels. There are two variations for multiplexed analysis with primers of differing length and nucleotide variations: (a) primer extension reactions using matched primer/nucleotide combinations may be carried out in the same reaction tube and (b) promer extension with incompatible nucleotide combinations may be performed separately and the products pooled prior to gel analysis. Thus, by judicious grouping of mutations and selection of primer lengths and dyes, it is possible to detect a number of mutations in a conventional automated DNA sequencer. Increased throughput is also obtained by batch loading of samples from different primer extension reactions in the same gel. Typically, gel electrophoresis may be performed with four to five sample loadings at timed intervals and a fluorescent eletrophoretogram is obtained with clearly resolved product bands.

Preparation of Primer Extension Reaction Templates

PCR amplification of cellular DNA was carried out as described in Example VIII. Residual nucleotides that persisted after completion of PCR were dephosphorylated by adding one unit of calf intestine phosphatase (CAP) in 5 µL of 10X CAP buffer (100 mM Tris.HCL,pH 8.3, 10 mM MgCl$_2$, 10 mM ZnCl$_2$) to the PCR reaction and incubating for 30 minutes at 37° C. in a thermal cycler. Then 1.1 µL of 0.25M EDTA, pH 8.0 was added and the alkaline phosphatase was denatured at 75° C. for ten minutes.

Double-stranded PCR products were separated from primers, nucleosides and enzymes using QIAquick™ columns (Qiagen, Chatsworth, Calif.) and the buffers provided by the manufacturer. Thus, 250 µL of buffer PB were added to the PCR reaction mixture and mixed therein. A Qiaquick™ spin column was placed in a 2 mL collection tube and the sample was loaded onto the column. The sample was centrifuged for about 30 to 60 seconds at 14000 g and the flowthrough was discarded. The absorbed PCR product was washed with 750 µL of buffer PE and eluted with 50 µL of 10 mM Tris.HCl, pH 8.5. The purified product solution was dried in a Savant SpeedVac Concentrator and then reconstituted in 20 µL of water.

Primer/Nucleotide Combinations for Primer Extension Assay

The fluorescein-labeledcombinationd nucleotide combinations for analysis of AD-associated mutations at nucleotide sites 6366, 6483, 7146, 7650, 7868 and 8021 are shown in Table 10. Stock solutions of each DNTP and ddNTP were prepared by mixing equimolar amounts of the nucleotides with MgCl$_2$ and diluting the mixture to the desired concentration with TE. The fluorescein-labeled primers were diluted in TE to provide final stock concentrations of 40 fmol/µL. One µL of the purified PCR-amplified DNA fragment was used as template for each assay.

Multiplexed Primer Extension Assay

Primer extension reactions were performed in a total volume of 8 µL. The ULTma™ DNA polymerase-catalyzed reactions contained template, 20 fmol fluorscein-labeled primer, 400 µM ddNTPs/25 µM dNTPs of the appropriate nucleotide combination and 0.6 unit of enzyme in buffer containing 10 mM Tris.HCl, pH 8.8, 10 mM KCl, 0.002% TWEEN® 20 and 2 mM MgCl$_2$. Thermo Sequenase™ polymerase catalyzed reactions were performed with 20 fmol fluorescein-labeled primer, 25 µM each of the appropriate ddNTP/dNTP combination and 0.64 unit of enzyme in buffer containing 10 mM Tris.HCl, pH 9.5, 5 mM KCl, 0.002% TWEEN® 20 and 2 mM MgCl$_2$. Each set of primer extension assays included controlled template preparations that had been amplified from homoplastic wild-type and mutant DNA controls. After an initial denaturation step at 95° C. for two minutes, the reaction conditions comprised twenty cycles of 95° C. for 20 seconds and 55° C. for 40 seconds. The samples were concentrated to about 1 µL by heating open reaction tubes at 94° C. for seven minutes. After the concentration step, 8 µL of loading dye (0.5% blue dextran in 83% formamide/8.3 mM EDTA, pH 8.0) was added.

The products of the primer extension reaction were analyzed on an ABI373 Sequencer using a 12% denaturing polyacrylamide gel and Tris borate/EDTA as running buffer. Prior to electrophoresis, the samples in loading dye were denatured for three minutes at 85° C. Three µL aliquots of the standards (primer with no added template, reaction products from homoplasmic wild-type and mutant DNA templates) and each unknown reaction mixture were then loaded onto the gel and separated by electrophoresis according to the manufacturers's instructions. Fluorescent band intensities associated with wild-type and mutant DNA derived extension products were estimated by GENESCAN™ 672 software program (Perkin-Elmer, Applied Biosystems Division). Quantitative analysis of heteroplasmy was carried out by correlating the fluorescent band intensities of wild-type and mutant DNA derived extension products from unknown samples with those from homoplasmic wild-type and mutant control templates.

TABLE 10

| GENE | BASE | SUBSTITUTION | SEQUENCE (5'→3') | SEQ ID NO | 5'-Label | LENGTH | PRODUCT SIZE | dNTP | ddNTP |
|---|---|---|---|---|---|---|---|---|---|
| COX1 | 6366 | G→A(Val/Ile) | TGATGAAATTGATGGCCCCTAAGATAGAGGAGA | 75 | FAM | 33 | WT34, M35 | T | A,C |
| COX1 | 6483 | C→T(silent) | AGGACTGGGAGAGATAGGAGAAGTA | 76 | FAM | 25 | WT28, M26 | G | A |
| COX1 | 7146 | A→G(Thr/Ala) | ACCTACGCCAAAATCCATTTC | 77 | FAM | 21 | WT22, M23 | G | A,C |
| COX2 | 7650 | C→T(Thr/Ile) | TATGAGGGCGTGATCATGAAAG | 78 | FAM | 22 | WT23, M25 | A,T | G |
| COX2 | 7650 | C→T(Thr/Ile) | TCCCCTATCATAGAAGAGCTTATCA | 79 | FAM | 25 | WT28, M26 | C | T |
| COX2 | 7868 | C→T(Leu/Phe) | GGCCAATTGATTTGATGGTAA | 80 | FAM | 21 | WT22, M23 | A | G,T |
| COX2 | 8021 | A→G(Ile/Val) | TTATTATACGAATGGGGCTTCAA | 81 | FAM | 24 | WT25, M27 | C | G,T |

TABLE 10-continued

| GENE | BASE | SUBSTITUTION SEQUENCE (5'→3') | SEQ ID NO | 5'-Label | LENGTH | PRODUCT SIZE | dNTP | ddNTP |
|---|---|---|---|---|---|---|---|---|

WT: WILD TYPE
M: MUTANT

What is claimed is:

1. A method for diagnosing the risk of having Alzheimer's disease in a patient comprising:
 a) obtaining a biological sample containing mitochondria from the patient;
 b) obtaining nucleic acids from said sample;
 c) determining the presence and frequency of at least one missense mutation in the sequence of a mitochondrial cytochrome c oxidase gene in said nucleic acids wherein the presence of at least one mutation correlates with risk of having Alzheimer's disease;
 d) quantitating the degree of heteroplasmy at the site of said at least one mutation in the nucleic acid; and
 e) correlating the presence of the at least one mutation and the degree of heteroplasmy with the risk of having Alzheimer's disease.

2. A method according to claim 1 wherein the presence of at least one mutation in the sequence of the mitochondrial cytochrome c oxidase gene is determined by application of an oligonucleotide ligation assay.

3. A method according to claim 1 wherein the presence of at least one mutation in the sequence of the mitochondrial cytochrome c oxidase gene is determined by nucleic acid hybridization.

4. A method according to claim 2 wherein the sequences of mutant and wild type mitochondnal cytochrome c oxidase gene are simultaneously analyzed by a ligase-catalysed reaction wherein labelled probe having a sequence common to, or complementary to, both wild type and mutant mitochondrial cytochrome c oxidase genes is ligated to the wild type and mutant genes; and at least two different allele specific probes having non-nucleotide mobility modifier tails attached thereto are reacted with the seuences of mutant and wild type mitochondrial cytochrome c oxidase genes, wherein said allele specific probes each contain a sequence specific to an allele of either mutant or wild type mitochondrial cytochrome c oxidase gene.

5. A method according to claim 4 wherein each allele specific probe is labelled at the 5' terminus thereof with a pentaethyleneoxide tail of unique length.

6. A method according to claim 4 wherein said labelled probe is labelled with a fluorescent dye.

7. A method according to claim 4 wherein said labelled probe and said at least two allele specific probes have a calculated melting temperature of from about 40° to abou 60° C.

8. A method according to claim 4 wherein said labelled probe and said at least two allele specific probes have a calculated meeting temperature of from about 45° C. to about 55° C.

9. A method according to claim 4 wherein the presence and frequency of at least one mutation in the mitochondrial cytochrome c oxidase gene is determined on the basis of size and fluorescence intensities of reaction products of the ligase catalyzed reaction.

10. A method according to claim 1 wherein the presence and frequency of at least one mutation in the mitochondrial cytochrome c oxidase gene are determined using a primer extension reaction assay using a detectably labeled primer and a mixture of deoxynucleotides and dideoxynucleotides, wherein the primer and mixture are selected so as to enable differential extension of the primer in the presence of wild-type and mutant DNA template.

11. A method according to claim 10 wherein the at least one mutation is located at a nucleotide selected from the group consisting of nucleotide 6366 of the COX 1 gene, nucleotide 6483 of the COX 1 gene, nucleotide 7146 of the COX 1 gene, nucleotide 7650 of the COX 2 gene, nucleotide 7868 of the COX 2 gene, nucleotide 8021 of the COX 2 gene, and combinations thereof.

12. A method according to claim 11 wherein the primer extension assay is carried out using SEQ ID NO:75 as the primer and a mixture of dTTP, ddATP and ddCTP.

13. A method according to claim 11 wherein the primer extension assay is carried out using SEQ ID NO:76 as the primer and a mixture of dGTP and ddATP.

14. A method according to claim 11 wherein the primer extension assay is carried out using SEQ ID NO:77 as the primer and a mixture of dGTP, ddATP and ddCTP.

15. A method according to claim 11 wherein the primer extension assay is carried out using SEQ ID NO:78 as the primer and a mixture of dATP, dTTP and ddGTP, or SEQ ID NO:80 as the primer and a mixture of dCTP and ddTTP.

16. A method according to claim 11 wherein the primer extension assay is carried out using SEQ ID NO:80 as the primer and a mixture of DATP, ddGTP and ddTTP.

17. A method according to claim 11 wherein the primer extension assay is carried out using SEQ ID NO:81 as the primer and a mixture of dCTP, ddGTP and ddTTP.

18. A method according to claim 1 wherein the presence and frequency of at least one mutation in the sequence of the mitochondrial c oxidase gene are determined by application of a multiplex oligonucleotide ligation assay wherein a set of primers which each have a sequence common to, or complementary to, both wild type and mutant mitochondrial cytochrome c oxidase genes are ligated to the wild type and mutant genes and reulting ligated nucleic acids are extended in the presence of a selected mixture of deoxyribonucleotides and dideoxyribonucleotides, which in ligation products that are distinguishable from one another on the basis of size or fluorescent label attached to said primers.

19. A method according to claim 2 wherein the sequence of the mitochondrial cytochrome c oxidase gene is simultaneously determined at a plurality of Alzheimer's disease-associated nucleotide sites in a single ligation reaction.

20. A method according to claim 2 further comprising the step of PCR amplification of the mitochondrial cytochrome c oxidase gene or a portion of the gene suspected of containing the at least one mutation said amplification providing PCR products, prior to application of the oligonucleotide ligation assay of the resulting PCR products.

21. A method according to claim 20 wherein the PCR products have a size of from about 200 to about 900 base pairs.

22. A method according to claim 2 wherein the mitochondral cytochrome c oxidase gene is analyzed at nucleotide positions 6386, 6483, 7146, 7650, 7868, 8021, or combinations thereof.

23. A method according to claim 4 wherein the presence of a mutation at nucleotide site 6366 of the COX 1 gene is determined using a combination of three different oligonucleotide probes wherein two probes are labelled at the 5' terminus with a pentaethyleneoxide tail of differing length and one probe is labelled with a fluorescent dye and wherein at least one probe encodes a sequence having the mutation or nucleotide complementary to the mutation at nucleotide site 6366 of the COX 1 gene.

24. A method according to claim 4 wherein the presence and frequency of a mutation at nucleotide site 6366 of the COX 1 gene is determined using a combination of three different probes wherein the probes encode the sequence of SEQ ID NO:3, SEQ ID NO:4 or SEQ ID NO:5, wherein each of the probes encoding the sequence of SEQ ID NO:3or SEQ ID NO:4 is labelled at the 5' terminus with a pentaethyleneoxide tail of differing length and the probe encoding the sequence of SEQ ID NO:5 is labelled with a fluorescein dye.

25. A method according to claim 4 wherein the presence and frequency of a mutation at nucleotide 6483 of the COX 1 gene is determined using a combination of three different probes wherein the probes encode the sequence of SEQ ID NO. 6, SEQ ID NO. 7 or SEQ ID NO. 8 and wherein the probes encoding the segence of SEQ ID NO. 6 or SEQ ID NO. 7 are labelled at the 5' terminus with a pentaethyleneoxide tail of differing length and the probe encoding the sequence of SEQ ID NO. 8 is labelled with a fluorescein dye.

26. A method according to claim 4 wherein the presence and frequency of a mutation at nucleotide 7146 of the COX 1 gene is determined using a combination of probes three diffrent probes wherein the probes encode the sequence of SEQ ID NO. 9, SEQ ID NO. 10 or SEQ ID NO. 11 and wherein the probes encoding the sequence of SEQ ID NO. 9 or SEQ ID NO. 10 are labelled at the 5' terminus with a pentaethyleneoxide tail of differing length and the probe encoding the sequence of SEQ ID NO. 11 is labelled with a fluorescein dye.

27. A method according to claim 4 wherein the presence and frequency of a mutation at nucleotide 7650 of the COX 2 gene is determined using a combination of three diffrent probes wherein the probes encode the sequence of SEO ID NO. 12, SEQ ID NO. 13 or SEQ ID NO. 14 and wherein the probes encoding the sequence of SEQ ID NO. 12 or SEQ ID NO. 13 are labelled at the 5' terminus with a pentaethyleneoxide tail of differing length and the probe encoding the sequence of SEQ ID NO. 14 is labelled with a fluorescein dye.

28. A method according to claim 4 wherein the presence and frequency of a mutation at nucleotide 7868 of the COX 2 gene is determined using a combination of three different probes wherein the probes encode the sequence of SEQ ID NO. 15, SEQ ID NO. 16 or SEQ ID NO. 17 and wherein the probes encoding the sequence of SEQ ID NO. 15 and 16 are labelled at the 5' terminus with a pentaethyleneoxide tail of differing length and SEQ ID NO. 17 is labelled with a fluorescein dye.

29. A method according to claim 4 wherein the presence and frequency of a mutation at nucleotide 8021 of the COX 2 gene is determined using a combination of probes comprising SEQ ID NO. 18, SEQ ID NO. 19 and SEQ ID NO. 20 wherein each of SEQ ID NO. 18 and 19 is labelled at the 5' terminue with a pentaethyleneoxide tail of differing length and the probe encoding the sequence of SEQ ID NO. 20 is labelled with a fluorescein dye.

30. A method according to claim 1 wherein the nucleic acid is DNA obtained by lysing cells of plateletrich white blood cell fraction of the biological sample by boiling said cell fraction in water and isolating the mitochondrial DNA therefrom.

31. A method according to claim 30 wherein in (c) the mitochondrial cytochrome c oxidase gene is amplified in full length or as a gene fragment.

32. A method for diagnosing the risk of having Alzheimer's disease in a patient comnrising:

a) obtaining a biological sample containing mitochondria from the patient;

b) obtaining nucleic acids from said sample;

c) determining the presence and frequency of at least one silent mutation in the sequence of a mitochondrial cytochrome c oxidase gene in said nucleic acids wherein the presence of at least one mutation correlates with risk of having Alzheimer's disease;

d) quantitating the degree of heteroplasmv at the site of said at least one mutation in the nucleic acid; and e) correlating the presence of the at least one mutation and the degree of heteroplasmy with the risk of having Alzheimer's disease.

33. A method according to claim 32 wherein the at least one mutation is selected from the group consisting of silent mutations at nucleotide sites 6221, 6242, 6266, 6299, 6383, 6410, 6452, 6483, 6512, 6542, 6569, 6641, 6935, 6938 of the COX 1 gene, nucleotide sites 7705, 7810, 7891, 7912 of the COX 2 gene, and combinations thereof.

34. The method of claim 1 wherein the step of determining the presence of at least one mutation further comprises detecting the presence of a silent mutation linked to said missense mutation, said silent mutation selected from the group consisting of silent mutations at nucleotide sites 6221, 6242, 6266, 6299, 6383, 6410, 6452, 6483, 6512, 6542, 6569, 6641, 6935, 6938 of the COX 1 gene, nucleotide sites 7705, 7810, 7891, 7912 of the COX 2 gene, and combinations thereof.

* * * * *

UNITED STATES PATENT AND TRADEMARK OFFICE
CERTIFICATE OF CORRECTION

PATENT NO. : 5,976,798  
DATED : November 2, 1999  
INVENTOR(S) : William Davis Parker et al.

Page 1 of 1

It is certified that error appears in the above-identified patent and that said Letters Patent is hereby corrected as shown below:

Claim 22, column 96,
Line 34, "positions 6386," should read -- positions 6366, --.

Signed and Sealed this

Sixteenth Day of October, 2001

Attest:

NICHOLAS P. GODICI  
Attesting Officer    Acting Director of the United States Patent and Trademark Office

SEQUENCE LISTING (1) GENERAL INFORMATION:

(iii) NUMBER OF SEQUENCES: 82

(2) INFORMATION FOR SEQ ID NO:1:

(i) SEQUENCE CHARACTERISTICS:
         (A) LENGTH: 1613 base pairs
         (B) TYPE: nucleic acid
         (C) STRANDEDNESS: double
         (D) TOPOLOGY: linear (ii) MOLECULE TYPE: genomic DNA (iii) HYPOTHETICAL: No (iv) ANTI-SENSE: No (xi) SEQUENCE DESCRIPTION: SEQ ID NO:1:

```
AGAGGCCTAA CCCCTGTCTT TAGATTTTAC AGTCCAATGC TTCACTCAGC CATTTTACCT      60
CACCCCCACT GATGTTCGCC GACCGTTGAC TATTCTCTAC AAACCACAAA GACATTGGAA     120
CACTATACCT ATTATTCGGC GCATGAGCTG GAGTCCTAGG CACAGCTCTA AGCCTCCTTA     180
TTCGAGCCGA GCTGGGCCAG CCAGGCAACC TTCTAGGTAA CGACCACATC TACAACGTTA     240
TCGTCACAGC CCATGCATTT GTAATAATCT TCTTCATAGT AATACCCATC ATAATCGGAG     300
GCTTTGGCAA CTGACTAGTT CCCCTAATAA TCGGTGCCCC CGATATGGCG TTTCCCCGCA     360
TAAACAACAT AAGCTTCTGA CTCTTACCTC CCTCTCTCCT ACTCCTGCTC GCATCTGCTA     420
TAGTGGAGGC CGGAGCAGGA ACAGGTTGAA CAGTCTACCC TCCCTTAGCA GGGAACTACT     480
CCCACCCTGG AGCCTCCGTA GACCTAACCA TCTTCTCCTT ACACCTAGCA GGTGTCTCCT     540
CTATCTTAGG GGCCATCAAT TTCATCACAA CAATTATCAA TATAAAACCC CCTGCCATAA     600
CCCAATACCA AACGCCCCTC TTCGTCTGAT CCGTCCTAAT CACAGCAGTC CTACTTCTCC     660
TATCTCTCCC AGTCCTAGCT GCTGGCATCA CTATACTACT AACAGACCGC AACCTCAACA     720
CCACCTTCTT CGACCCCGCC GGAGGAGGAG ACCCCATTCT ATACCAACAC CTATTCTGAT     780
TTTTCGGTCA CCCTGAAGTT TATATTCTTA TCCTACCAGG CTTCGGAATA ATCTCCCATA     840
TTGTAACTTA CTACTCCGGA AAAAAGAAC CATTTGGATA CATAGGTATG GTCTGAGCTA      900
TGATATCAAT TGGATTCCTA GGGTTTATCG TGTGAGCACA CCATATATTT ACAGTAGGAA     960
TAGACGTAGA CACACGAGCA TATTTCACCT CCGCTACCAT AATCATCGCT ATCCCCACCG    1020
GCGTCAAAGT ATTTAGCTGA CTCGCCACAC TCCACGGAAG CAATATGAAA TGATCTGCTG    1080
CAGTGCTCTG AGCCCTAGGA TTCATCTTTC TTTTCACCGT AGGTGGCCTG ACTGGCATTG    1140
TATTAGCAAA CTCATCACTA GACATCGTAC TACACGACAC GTACTACGTT GTAGCCCACT    1200
TCCACTATGT CCTATCAATA GGAGCTGTAT TTGCCATCAT AGGAGGCTTC ATTCACTGAT    1260
TTCCCCTATT CTCAGGCTAC ACCCTAGACC AAACCTACGC CAAAATCCAT TTCACTATCA    1320
TATTCATCGG CGTAAATCTA ACTTTCTTCC CACAACACTT TCTCGGCCTA TCCGGAATGC    1380
CCCGACGTTA CTCGGACTAC CCCGATGCAT ACACCACATG AAACATCCTA TCATCTGTAG    1440
GCTCATTCAT TTCTCTAACA GCAGTAATAT TAATAATTTT CATGATTTGA GAAGCCTTCG    1500
CTTCGAAGCG AAAAGTCCTA ATAGTAGAAG AACCCTCCAT AAACCTGGAG TGACTATATG    1560
GATGCCCCCC ACCCTACCAC ACATTCGAAG AACCCGTATA CATAAAATCT AGA           1613
```

(2) INFORMATION FOR SEQ ID NO:2:

(i) SEQUENCE CHARACTERISTICS:
    (A) LENGTH: 694 base pairs
    (B) TYPE: nucleic acid
    (C) STRANDEDNESS: double
    (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:2:

```
AGGTATTAGA AAAACCATTT CATAACTTTG TCGTCAAAGT TAAATTATAG GCTAAATCCT    60
ATATATCTTA ATGGCACATG CAGCGCAAGT AGGTCTACAA GACGCTACTT CCCCTATCAT   120
AGAAGAGCTT ATCACCTTTC ATGATCACGC CCTCATAATC ATTTTCCTTA TCTGCTTCCT   180
AGTCCTGTAT GCCCTTTTCC TAACACTCAC AACAAAACTA ACTAATACTA ACATCTCAGA   240
CGCTCAGGAA ATAGAAACCG TCTGAACTAT CCTGCCCGCC ATCATCCTAG TCCTCATCGC   300
CCTCCATCCC TACGCATCCT TTACATAACA GACGAGGTCA ACGATCCCTC CCCTTACCAT   360
CAAATCAATT GGCCACCAAT GGTACTGAAC CTACGAGTAC ACCGACTACG GCGGACTAAT   420
CTTCAACTCC TACATACTTC CCCCATTATT CCTAGAACCA GGCGACCTGC GACTCCTTGA   480
CGTTGACAAT CGAGTAGTAC TCCCGATTGA AGCCCCCATT CGTATAATAA TTACATCACA   540
ACGTCTAAAC CAAACCACTT TCACCGCTAC ACGACCGGGG GTATACTACG GTCAATGCTC   600
TGAAATCTGT GGAGCAAACC ACAGTTTCAT GCCCATCGTC CTAGAATTAA TTCCCCTAAA   660
AATCTTTGAA ATAGGGCCCG TATTTACCCT ATAG                               694
```

(2) INFORMATION FOR SEQ ID NO:3:

(i) SEQUENCE CHARACTERISTICS:
    (A) LENGTH: 18 base pairs
    (B) TYPE: nucleic acid
    (C) STRANDEDNESS: double
    (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:3:

```
CCTTACACCT AGCAGGTG                                                  18
```

(2) INFORMATION FOR SEQ ID NO:4:

(i) SEQUENCE CHARACTERISTICS:
    (A) LENGTH: 19 base pairs
    (B) TYPE: nucleic acid
    (C) STRANDEDNESS: double
    (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:4:

```
TCCTTACACC TAGCAGGTA                                                 19
```

(2) INFORMATION FOR SEQ ID NO:5:

```
    (i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:5:

TCTCCTCTAT CTTAGGGGC                                                19

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:6:

CCTAATCACA GCAGTCC                                                  17

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:7:

TCCTAATCAC AGCAGTCT                                                 18

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:8:

TACTTCTCCT ATCTCTCCC                                                19

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: double
```

(D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:9:

CCAAAATCCA TTTCA                                                        15

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:10:

CCAAAATCCA TTTCG                                                        15

(2) INFORMATION FOR SEQ ID NO:11:

(i) SEQUENCE CHARACTERISTICS:
            (A) LENGTH: 17 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:11:

CTATCATATT CATCGGC                                                      17

(2) INFORMATION FOR SEQ ID NO:12:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:12:

ATCATAGAAG AGCTTATCAC                                                   20

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: other nucleic acid

```
        (iii) HYPOTHETICAL: No (iv) ANTI-SENSE: No (xi) SEQUENCE DESCRIPTION: SEQ ID NO:13:

ATCATAGAAG AGCTTATCAT                                                   20

(2) INFORMATION FOR SEQ ID NO:14:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:14:

CTTTCATGAT CACGC                                                        15

(2) INFORMATION FOR SEQ ID NO:15:

(i) SEQUENCE CHARACTERISTICS:
            (A) LENGTH: 14 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:15:

CAACGATCCC TCCC                                                         14

(2) INFORMATION FOR SEQ ID NO:16:

(i) SEQUENCE CHARACTERISTICS:
            (A) LENGTH: 15 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:16:

TCAACGATCC CTCCT                                                        15

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No
```

(xi) SEQUENCE DESCRIPTION: SEQ ID NO:17:

TTACCATCAA ATCAATTG                                                          18

(2) INFORMATION FOR SEQ ID NO:18:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:18:

AATCGAGTAC TCCCGA                                                            16

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:19:

ATCGAGTAGT ACTCCCGG                                                          18

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:20:

TTGAAGCCCC CATTC                                                             15

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:21:

GAGCCTCCGT AGACCTAACC ATCT                                                   24

(2) INFORMATION FOR SEQ ID NO:22:

(i) SEQUENCE CHARACTERISTICS:
      (A) LENGTH: 22 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:22:

GGTCGAAGAA GGTGGTGTTG AG                                          22

(2) INFORMATION FOR SEQ ID NO:23:

(i) SEQUENCE CHARACTERISTICS:
      (A) LENGTH: 25 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:23:

CCATCATAGG AGGCTTCATT CACTG                                       25

(2) INFORMATION FOR SEQ ID NO:24:

(i) SEQUENCE CHARACTERISTICS:
      (A) LENGTH: 27 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:24:

TGATAGGATG TTTCATGTGG TGTATGC                                     27

(2) INFORMATION FOR SEQ ID NO:25:

(i) SEQUENCE CHARACTERISTICS:
      (A) LENGTH: 27 base pairs
      (B) TYPE: nucleic acid
      (C) STRANDEDNESS: double
      (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:25:

CATGCAGCGC AAGTAGGTCT ACAAGAC                                     27

(2) INFORMATION FOR SEQ ID NO:26:

(i) SEQUENCE CHARACTERISTICS:

```
            (A) LENGTH: 24 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:26:

AGCCTAATGT GGGGACAGCT CATG                                              24

(2) INFORMATION FOR SEQ ID NO:27:

(i) SEQUENCE CHARACTERISTICS:
            (A) LENGTH: 23 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:27:

CAATATGAAA ATCACCTCGG AGC                                               23

(2) INFORMATION FOR SEQ ID NO:28:

(i) SEQUENCE CHARACTERISTICS:
            (A) LENGTH: 23 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:28:

TTAGCCTATA ATTTAACTTT GAC                                               23

(2) INFORMATION FOR SEQ ID NO:29:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:29:

CAAGCCAACC CCATGGCCTC C                                                 21

(2) INFORMATION FOR SEQ ID NO:30:

(i) SEQUENCE CHARACTERISTICS:
            (A) LENGTH: 23 base pairs
            (B) TYPE: nucleic acid
            (C) STRANDEDNESS: double
            (D) TOPOLOGY: linear
```

(ii) MOLECULE TYPE: other nucleic acid (iii) HYPOTHETICAL: No (iv) ANTI-SENSE: No (xi) SEQUENCE DESCRIPTION: SEQ ID NO:30:

AGTATTTAGT TGGGGCATTT CAC     23

(2) INFORMATION FOR SEQ ID NO:31:

(i) SEQUENCE CHARACTERISTICS:
 (A) LENGTH: 25 base pairs
 (B) TYPE: nucleic acid
 (C) STRANDEDNESS: double
 (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:31:

ACAATTCTAA TTCTACTGAC TATCC     25

(2) INFORMATION FOR SEQ ID NO:32:

(i) SEQUENCE CHARACTERISTICS:
 (A) LENGTH: 23 base pairs
 (B) TYPE: nucleic acid
 (C) STRANDEDNESS: double
 (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:32:

TTAGTAGTAA GGCTAGGAGG GTG     23

(2) INFORMATION FOR SEQ ID NO:33:

(i) SEQUENCE CHARACTERISTICS:
 (A) LENGTH: 21 base pairs
 (B) TYPE: nucleic acid
 (C) STRANDEDNESS: double
 (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:33:

TTACAGTCCA ATGCTTCACT C     21

(2) INFORMATION FOR SEQ ID NO:34:

(i) SEQUENCE CHARACTERISTICS:
 (A) LENGTH: 19 base pairs
 (B) TYPE: nucleic acid
 (C) STRANDEDNESS: double
 (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:34:

TGTTTATGCG GGGAAACGC                                                    19

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:35:

AATCGGAGGC TTTGGCAACT G                                                 21

(2) INFORMATION FOR SEQ ID NO:36:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:36:

TGGTATTGGG TTATGGCAGG G                                                 21

(2) INFORMATION FOR SEQ ID NO:37:

(i) SEQUENCE CHARACTERISTICS:
            (A) LENGTH: 22 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:37:

TAGCAGGTGT CTCCTCTATC TT                                                22

(2) INFORMATION FOR SEQ ID NO:38:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:38:

```
CCATACCTAT GTATCCAAAT GGTTC                                              25
```

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:39:

```
GGAATAATCT CCCATATTGT AACTT                                              25
```

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:40:

```
GTCAGGCCAC CTACGGTG                                                      18
```

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:41:

```
ATGATCTGCT GCAGTGCTCT                                                    20
```

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:42:

```
ATTCCGGATA GGCCGAGA                                                      18
```

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:43:

TCGGCGTAAA TCTAAGTTTC TT                                    22

(2) INFORMATION FOR SEQ ID NO:44:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:44:

TTGGCTTGAA ACCAGCTTT                                       19

(2) INFORMATION FOR SEQ ID NO:45:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:45:

GTCAAAGTTA AATTATAGGC TAA                                  23

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:46:

TGACCTCGTC TGTTATGTAA AGG                                  23

(2) INFORMATION FOR SEQ ID NO:47:

(i) SEQUENCE CHARACTERISTICS:
        (A) LENGTH: 20 base pairs

```
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:47:

CGCCATCATC CTAGTCCTCA                                              20

(2) INFORMATION FOR SEQ ID NO:48:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:48:

ATGAGTGCAA GACGTCTTGT GAT                                          23

(2) INFORMATION FOR SEQ ID NO:49:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:49:

GAGTAGTACT CCCGATTGAA GCC                                          23

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:50:

AGTTAGCTTT ACAGTGGGCT CTAG                                         24

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: double
        (D) TOPOLOGY: linear
```

(ii) MOLECULE TYPE: other nucleic acid (iii) HYPOTHETICAL: No (iv) ANTI-SENSE: No (xi) SEQUENCE DESCRIPTION: SEQ ID NO:51:

TTCTAGTAAG CCTCTACCTG CACG                                      24

(2) INFORMATION FOR SEQ ID NO:52:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:52:

AATAAATAGG ATTATCCCGT ATCGA                                     25

(2) INFORMATION FOR SEQ ID NO:53:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:53:

ACCACACACC ACCTGTCCA                                            19

(2) INFORMATION FOR SEQ ID NO:54:

(i) SEQUENCE CHARACTERISTICS:
            (A) LENGTH: 23 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:54:

AAGGGAGACT CGAAGTACTC TGA                                       23

(2) INFORMATION FOR SEQ ID NO:55:

(i) SEQUENCE CHARACTERISTICS:
            (A) LENGTH: 23 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:55:

TATTACAATT TTACTGGGTC TCT                                            23

(2) INFORMATION FOR SEQ ID NO:56:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:56:

ACTAGTTAAT TGGAAGTTAA CGGTA                                          25

(2) INFORMATION FOR SEQ ID NO:57:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:57:

AGGCCTAACC CCTGTC                                                    16

(2) INFORMATION FOR SEQ ID NO:58:

(i) SEQUENCE CHARACTERISTICS:
            (A) LENGTH: 13 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:58:

GTCACAGCCC ATG                                                       13

(2) INFORMATION FOR SEQ ID NO:59:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:59:

-continued

```
CCTGGAGCCT CCGTAG                                                      16

(2) INFORMATION FOR SEQ ID NO:60:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:60:

CTTCTTCGAC CCCG                                                        14

(2) INFORMATION FOR SEQ ID NO:61:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:61:

CATATTTCAC CTCCG                                                       15

(2) INFORMATION FOR SEQ ID NO:62:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:62:

CCTATCAATA GGAGC                                                       15

(2) INFORMATION FOR SEQ ID NO:63:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:63:

CATCCTATCA TCTGTAGG                                                    18

(2) INFORMATION FOR SEQ ID NO:64:
```

(i) SEQUENCE CHARACTERISTICS:
    (A) LENGTH: 17 base pairs
    (B) TYPE: nucleic acid
    (C) STRANDEDNESS: double
    (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:64:

AGGTATTAGA AAAACCA                                                17

(2) INFORMATION FOR SEQ ID NO:65:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:65:

TAACTAATAC TAACATCT                                               18

(2) INFORMATION FOR SEQ ID NO:66:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:66:

TGCGACTCCT TGAC                                                   14

(2) INFORMATION FOR SEQ ID NO:67:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:67:

GCCTTAATCC AAGCC                                                  15

(2) INFORMATION FOR SEQ ID NO:68:

(i) SEQUENCE CHARACTERISTICS:
        (A) LENGTH: 16 base pairs
        (B) TYPE: nucleic acid (C) STRANDEDNESS: double
          (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:68:

CAATGATGGC GCGATG                                                16

(2) INFORMATION FOR SEQ ID NO:69:

(i) SEQUENCE CHARACTERISTICS:
          (A) LENGTH: 19 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:69:

CCGTATTACT CGCATCAGG                                             19

(2) INFORMATION FOR SEQ ID NO:70:

(i) SEQUENCE CHARACTERISTICS:
          (A) LENGTH: 17 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:70:

CCGACGGCAT CTACGGC                                               17

(2) INFORMATION FOR SEQ ID NO:71:

(i) SEQUENCE CHARACTERISTICS:
          (A) LENGTH: 15 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:71:

GTAAAACGAC GGCCA                                                 15

(2) INFORMATION FOR SEQ ID NO:72:

(i) SEQUENCE CHARACTERISTICS:
          (A) LENGTH: 17 base pairs
          (B) TYPE: nucleic acid
          (C) STRANDEDNESS: double
          (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:72:

CAGGAAACAG CTATGAC                                                      17

(2) INFORMATION FOR SEQ ID NO:73:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:73:

AGGGCGTGAT CATGAAAGGT GATA                                              24

(2) INFORMATION FOR SEQ ID NO:74:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:74:

GGCCAATTGA TTTGATGGTA                                                   20

(2) INFORMATION FOR SEQ ID NO:75:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:75:

TGATGAAATT GATGGCCCCT AAGATAGAGG AGA                                    33

(2) INFORMATION FOR SEQ ID NO:76:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:76:

AGGACTGGGA GAGATAGGA GAAGTA                                          25

(2) INFORMATION FOR SEQ ID NO:77:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:77:

ACCTACGCCA AAATCCATTT C                                              21

(2) INFORMATION FOR SEQ ID NO:78:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:78:

TATGAGGGCG TGATCATGGA AG                                             22

(2) INFORMATION FOR SEQ ID NO:79:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:79:

TCCCCTATCA TAGAAGAGCT TATCA                                          25

(2) INFORMATION FOR SEQ ID NO:80:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:80:

GGCCAATTGA TTTGATGGTA A                                              21

(2) INFORMATION FOR SEQ ID NO:81:

(i) SEQUENCE CHARACTERISTICS:
  (A) LENGTH: 24 base pairs
  (B) TYPE: nucleic acid
  (C) STRANDEDNESS: double
  (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:81:

```
TTATTATACG AATGGGGGCT TCAA                                          24
```

(2) INFORMATION FOR SEQ ID NO:82:

(i) SEQUENCE CHARACTERISTICS:
  (A) LENGTH: 926 base pairs
  (B) TYPE: nucleic acid
  (C) STRANDEDNESS: double
  (D) TOPOLOGY: linear (ii) MOLECULE TYPE: other nucleic acid (iii) HYPOTHETICAL: No (iv) ANTI-SENSE: No (xi) SEQUENCE DESCRIPTION: SEQ ID NO:82:

```
TCGCTGTCGC CTTAATCCAA GCCTACGTTT TCACACTTCT AGTAAGCCTC TACCTGCACG     60

ACAACACATA ATGACCCACC AATCACATGC CTATCATATA GTAAAACCCA GCCCATGACC    120

CCTAACAGGG GCCCTCTCAG CCCTCCTAAT GACCTCCGGC CTAGCCATGT GATTTCACTT    180

CCACTCCATA ACGCTCCTCA TACTAGGCCT ACTAACCAAC ACACTAACCA TATACCAATG    240

ATGGCGCGAT GTAACACGAG AAAGCACATA CCAAGGCCAC CACACACCAC CTGTCCAAAA    300

AGGCCTTCGA TACGGGATAA TCCTATTTAT TACCTCAGAA GTTTTTTTCT TCGCAGGATT    360

TTTCTGAGCC TTTTACCACT CCAGCCTAGC CCCTACCCCC CAATTAGGAG GGCACTGGCC    420

CCGAACAGGC ATCACCCCGC TAAATCCCCT AGAAGTCCCA CTCCTAAACA CATCCGTATT    480

ACTCGCATCA GGAGTATCAA TCACCTGAGC TCACCATAGT CTAATAGAAA ACAACCGAAA    540

CCAAATAATT CAAGCACTGC TTATTACAAT TTTACTGGGT CTCTATTTTA CCCTCCTACA    600

AGCCTCAGAG TACTTCGAGT CTCCCTTCAC CATTTCCGAC GGCATCTACG GCTCAACATT    660

TTTTGTAGCC ACAGGCTTCC ACGGACTTCA CGTCATTATT GGCTCAACTT TCCTCACTAT    720

CTGCTTCATC CGCCAACTAA TATTTCACTT TACATCCAAA CATCACTTTG GCTTCGAAGC    780

CGCCGCCTGA TACTGGCATT TTGTAGATGT GGTTTGACTA TTTCTGTATG TCTCCATCTA    840

TTGATGAGGG TCTTACTCTT TTAGTATAAA TAGTACCGTT AACTTCCAAT TAACTAGTTT    900

TGACAACATT CAAAAAAGAG TAATAA                                        926
```